US005700940A

United States Patent [19]
Van Heertum et al.

[11] Patent Number: 5,700,940
[45] Date of Patent: Dec. 23, 1997

[54] N-ARYL[1,2,4]TRIAZOLO[1,5-A]PYRIDINE-2-SULFONAMIDE HERBICIDES

[75] Inventors: John C. Van Heertum; William A. Kleschick; Kim E. Arndt; Mark J. Costales; Robert J. Ehr; Kimberly Brubaker Bradley, all of Indianapolis, Ind.; Walter Reifschneider, Walnut Creek, Calif.; Zoltan Benkö, Indianapolis, Ind.; Mary Lynne Ash; John J. Jachetta, both of Zionsville, Ind.

[73] Assignee: DowElanco, Indianapolis, Ind.

[21] Appl. No.: 714,838

[22] Filed: Sep. 6, 1996

Related U.S. Application Data

[60] Division of Ser. No. 466,510, Jun. 6, 1995, Pat. No. 5,571,775, which is a continuation-in-part of Ser. No. 273,519, Jul. 11, 1994, abandoned.

[51] Int. Cl.$^6$ .................... C07D 471/04; A01N 43/90
[52] U.S. Cl. .............................. 546/119; 504/246
[58] Field of Search .......................... 546/119; 504/246

[56] References Cited

U.S. PATENT DOCUMENTS

| | | |
|---|---|---|
| 4,605,433 | 8/1986 | Pearson et al. ............ 71/93 |
| 4,818,273 | 4/1989 | Kleschick et al. .......... 71/90 |
| 4,822,404 | 4/1989 | Kleschick et al. .......... 71/92 |
| 5,013,351 | 5/1991 | Jelich et al. ................ 71/92 |
| 5,163,995 | 11/1992 | Van Heertum et al. ...... 71/92 |

FOREIGN PATENT DOCUMENTS

| | | |
|---|---|---|
| 244948 | 11/1987 | European Pat. Off. |
| 2054630 | 2/1981 | United Kingdom. |

OTHER PUBLICATIONS

Houston, et al., *Journal of Medicinal Chemistry*, 28, 467–471 (1985).

Bouteau, et al., *J. Heterocyclic Chem.*, 27, 1649 (1990).

Vercek, et al., *Monatshefte für Chemie*, 114, 789–798 (1983).

Potts, et al., *Journal of Organic Chemistry*, 31 265–273 (1966).

Medwid, et al., *J. Med. Chem.* (33) 1230–1241 (1990).

*Primary Examiner*—C. Warren Ivy
*Assistant Examiner*—Evelyn Huang
*Attorney, Agent, or Firm*—D. Wendell Osborne

[57] ABSTRACT

Substituted N-aryl[1,2,4]triazolo[1,5-a]pyridine-2-sulfonamide compounds, such as N-(2,6-difluorophenyl)-5-methoxy-7-methyl[1,2,4]triazolo[1,5-a]pyridine-2-sulfonamide, N-(4-bromo-1-methyl-3-pyrazolyl)-8-chloro-5-methoxy[1,2,4]triazolo[1,5-a]pyridine-2-sulfonamide, and N-(2-fluoro-4-methyl-3-pyridinyl)-8-ethoxy-6-chloro[1,2,4]triazolo[1,5-a]pyridine-2-sulfonamide, were prepared by condensation of a 2-chlorosulfonyl[1,2,4]triazolo[1,5-a]pyridine compound with an aryl amine. The compounds prepared were found to possess excellent herbicidal activity on a broad spectrum of vegetation at low application rates.

15 Claims, No Drawings

N-ARYL[1,2,4]TRIAZOLO[1,5-A]PYRIDINE-2-SULFONAMIDE HERBICIDES

This is a divisional of application Ser. No. 08/466,510 filed Jun. 6, 1995 U.S. Pat. No. 5,571,775 which is a continuation-in-part of application Ser. No. 08/273,519 filed on Jul. 11, 1994, abandoned.

BACKGROUND OF THE INVENTION

The present invention relates to substituted sulfonamide compounds, to herbicidal compositions containing the compounds, and to the utility of the compounds for the control of unwanted vegetation.

The control of unwanted vegetation by means of chemical agents, i.e., herbicides, is an important aspect of modern agriculture and land management. While many chemicals that are useful for the control of unwanted vegetation are known, new compounds that are more effective generally, are more effective for specific plant species, are less damaging to desirable vegetation, are safer to man or the environment, are less expensive to use, or have other advantageous attributes are desirable.

A number of sulfonamide compounds, including certain substituted [1,2,4]triazolo[1,5-a]pyrimidine-2-sulfonamide compounds (U.S. Pat. No. 4,954,163), and [1,2,4]triazolo[1,5-c]pyrimidine-2-sulfonamide compounds (U.S. Pat. No. 5,010,195 and European Application 244,948) are known and are known to possess herbicidal activity, especially on broadleaf weeds.

SUMMARY OF THE INVENTION

It has now been found that certain N-aryl[1,2,4]triazolo[1,5-a]pyridine-2-sulfonamide compounds are potent herbicides for the control of unwanted vegetation, have desirable crop selectivity, and have favorable toxicological and environmental attributes.

The invention includes N-aryl[1,2,4]triazolo[1,5-a]pyridine-2-sulfonamide compounds of Formula I:

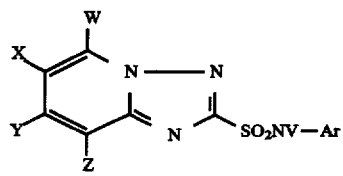

wherein

W, X, Y, and Z each independently represents H, $CH_3$, $CH_2CH_3$, $CH_2OCH_3$, $CF_3$, F, Cl, Br, I, $OCH_2CF_3$, $S(C_1-C_3)$alkyl, or $O(C_1-C_3)$alkyl optionally monosubstituted with F, Cl, or $OCH_3$, with the proviso that at least one of W, X, Y, and Z represents H;

V represents H, COR', $CO_2R''$, or $CONR'''_2$;

Ar represents an aromatic moiety one of the formulas:

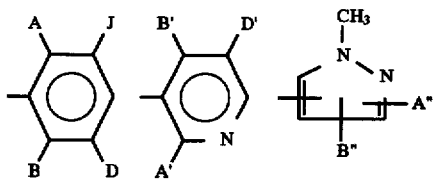

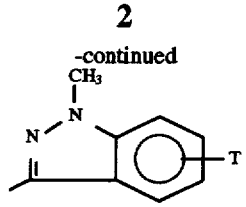

A represents F, Cl, Br, $CO_2R''$, $CONR'''_2$, $(C_1-C_2)$ haloalkyl, $NO_2$, CN, SOR', or $SO_2R'$;

B represents H, $CH_3$, $C_2H_5$, F, Cl, Br, CN, OR', SR', $NR'''_2$, phenyl, or phenoxy, each phenyl and phenoxy optionally possessing 1 to 3 substituents selected from the group consisting of F, Cl, Br, CN, $CF_3$, $NO_2$, and $CH_3$;

D and J each independently represents H or $CH_3$ with the proviso that at least one of D and J represents H;

A' and B' each independently represents H, R', OR', $OCH_2CH_2Cl$, $OCH_2CH_2OCH_3$, $S(O)_nR'$, F, Cl, Br, I, CN, $NO_2$, $C_6H_5$, $CO_2R''$, or $CONR'''_2$ with the proviso that not more than one of A' and B' represents H;

D' represents H, F, Cl, Br, I, $CF_3$, or $CH_3$;

A" represents F, Cl, Br, I, $CF_3$, $SCF_3$, CN, $CO_2R''$, or $CONR'''_2$ and is located in the 4-position when the point of attachment is the 3- or 5-position and represents F, Cl, Br, I, $CF_3$, or $CH_3$ and is located in the 3- or 5-position when the point of attachment is the 4-position;

B" represents H when the point of attachment is the 3- or 5-position and represents H, Cl, Br, F, $CH_3$, or $OCH_3$ and is located the 3- or 5-position not occupied by A" when the point of attachment is the 4-position;

T represents H or F;

n represents 0, 1, or 2;

R' represents $(C_1-C_4)$alkyl optionally singly to completely substituted with fluorine;

R" represents $(C_1-C_4)$alkyl, $(C_3-C_4)$alkenyl, or $(C_3-C_4)$alkynyl;

R''' represents H or $(C_1-C_4)$alkyl; and when V represents H, the agriculturally acceptable salts thereof.

The compounds of the invention, usually in the form of an herbicidal composition containing one or more of them in admixture with an agriculturally acceptable adjuvant or carrier, exhibit strong herbicidal properties when applied either directly to the unwanted vegetation or to the locus thereof and when applied either preemergence or postemergence.

The invention includes certain intermediates that are useful in the preparation of the herbicidal compounds of the invention.

DETAILED DESCRIPTION OF THE INVENTION

The herbicidal compounds of the invention are N-aryl[1,2,4]triazolo[1,5-a]pyridine-2-sulfonamide compounds of Formula I:

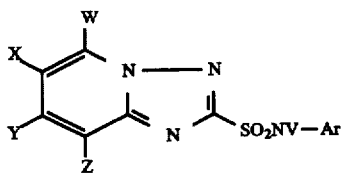

These compounds can be described as amides derived from substituted [1,2,4]triazolo[1,5-a]pyridine-2-sulfonic acid compounds and substituted aromatic amine compounds, such as anilines, aminopyridines, aminopyrazoles, and aminoindazoles.

The Chemical Abstracts nomenclature numbering system for [1,2,4]triazolo[1,5-a]pyridine ring compounds is as follows:

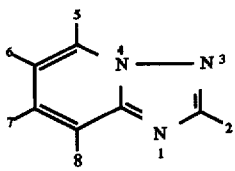

Thus, the compounds of the invention are 2-sulfonamide compounds and the W substituents are in the 5-position, the X substituents are in the 6-position, the Y substituents are in the 7-position, and the Z substituents are in the 8-position.

The compounds of the invention include those of Formula I wherein up to three of W, X, Y, and Z independently represent $CH_3$, $CH_2CH_3$, $CH_2OCH_3$, $CF_3$, F, Cl, Br, I, $OCH_2CF_3$, $S(C_1-C_3)$alkyl, or $O(C_1-C_3)$alkyl optionally monosubstituted with F, Cl, or $OCH_3$ and the remaining one to four of W, X, Y, and z represent hydrogen. Compounds wherein two of W, X, Y, and Z represent hydrogen are usually preferred. Compounds wherein one or both of W and Z represents methoxy or wherein one of W and Z represents ethoxy or isopropoxy are, further, typically preferred. Those wherein W represents methoxy or ethoxy are typically more preferred. Compounds of Formula I wherein W represents methoxy, ethoxy, or isopropoxy, X and Z each represent hydrogen, and Y represents methyl or a halogen; or wherein W represents methoxy or ethoxy, X and Y each represent hydrogen, and Z represents methyl, methoxy, or a halogen; or wherein Z represents methoxy or ethoxy, W and Y each represent hydrogen, and X represents methyl, trifluoromethyl, or a halogen are often of special interest.

V represents hydrogen or an acyl derivative, such as $CO(C_1-C_4)$alkyl optionally singly to completely substituted with fluorine, $CO_2(C_1-C_4)$alkyl, $CO_2(C_3-C_4)$alkenyl, $CO_2(C_3-C_4)$alkynyl, $CON((C_1-C_4)$alkyl$)_2$, $CONH(C_1-C_4)$alkyl, or $CONH_2$. Hydrogen is generally preferred. When V represents hydrogen, the invention includes the agriculturally acceptable salts obtained by neutralizing the resulting acid with a base.

The term Ar in Formula I represents an aromatic moiety, especially an aromatic moiety of one the following formulas:

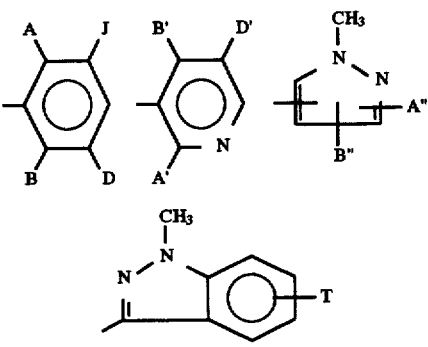

which includes phenyl moieties, 3-pyridinyl moieties, 1-methyl-(3-, 4-, or 5-)pyrazolyl moieties, and 1-methyl-3-indazolyl moieties.

When Ar represents a phenyl moiety, the moiety is substituted in at Least one ortho position with an electron withdrawing group. Compounds of Formula I wherein Ar represents a substituted phenyl moiety include those wherein A represents F, Cl, Br, $CO_2R'''$, $CONR'''_2$, $(C_1-C_2)$haloalkyl, $NO_2$, CN, SOR', or $SO_2R'$; B represents H, $CH_3$, $C_2H_5$, F, Cl, Br, CN, OR', SR', $NR'''_2$, phenyl, or phenoxy, each phenyl and phenoxy optionally possessing 1 to 3 substituents selected from the group consisting of F, Cl, Br, CN, $CF_3$, $NO_2$, and $CH_3$; and D and J each independently represents H or $CH_3$ with the proviso that at least one of D and J represents H. Compounds wherein A represents F, Cl, Br, $CF_3$, $NO_2$, or $CO_2CH_3$; B represents F, Cl, Br, $CCH_3$, or $CH_3$; J represents H; and D represents H or $CH_3$ are often preferred. Compounds wherein A and B both represent F or Cl and D and J both represent H, wherein A and B both represent F or Cl, D represents $CH_3$, and D represents H, wherein A represents $CO_2CH_3$, B represents Cl or F, and D and J both represent H, and wherein A represents $CF_3$, B represents $OCH_3$, and D and J both represent H are often more preferred.

When Ar represents a 3-pyridinyl moiety, the moiety is substituted in at least one of the 2- and 4-positions. Compounds that are substituted in both of these positions are often preferred. Compounds of Formula I wherein Ar represents a substituted 3-pyridinyl moiety include those wherein A' and B' are selected from H, F, C, Br, I, CN, $NO_2$, $C_6H_5$, $CO_2R''$, $CONR'''_2$, 2-chloroethoxy or 2-methoxyethoxy, or $(C_1-C_4)$alkyl, $(C_1-C_4)$alkoxy, $(C_1-C_4)$alkylthio, $(C_1-C_4)$alkylsulfinyl, or $(C_1-C_4)$alkylsulfonyl each optionally singly to completely substituted with fluorine, and D' represents H, F, Cl, Br, I, $CF_3$, or $CH_3$. Compounds wherein A' represents $CH_3$, $O(C_1-C_3)$alkyl, F, Cl, Br, or I; B' represents F, Cl, Br, I, $CH_3$, $C_2H_5$, $CF_3$, $O(C_1-C_3)$alkyl, $OCH(CH_3)CF_3$, $OCH_2CH_2F$, $OCH_2CHF_2$ or $CO_2(C_1-C_3)$alkyl; and D' represents H are often preferred. Such compounds wherein A' represents Br, Cl, F, or $OCH_3$, B' represents $CH_3$, $OCH_3$, $OC_2H_5$, $OC_3H_7(n)$, $OC_3H_7(i)$, $OCH(CH_3)CF_3$, or $OCH_2CH_2F$, and D' represents H; or wherein A' represents $OCH_3$ or $OC_2H_5$, B' represents $CO_2(C_1-C_2)$alkyl, Br, Cl, or F, and D' represents H are typically more preferred. 3-Pyridinyl moieties wherein A' represents F, Cl, Br, or $OCH_3$, B' represents $CH_3$, $OCH_3$, $OC_2H_5$, $OC_3H_7(n)$, $OC_3H_7(i)$, $OCH(CH_3)CF_3$, or $OCH_2CH_2F$, and D' represents H are sometimes especially preferred. 3-Pyridinyl moieties are often preferred Ar moieties.

When Ar represents a pyrazolyl moiety, the moiety is attached to the sulfonamide nitrogen atom at a 3-, 4-, or 5-position and has a methyl group in the 1-position. When the point of attachment is the 3- or 5-position, the moiety is substituted in the 4-position with an electron withdrawing group. The 3- or 5-position attachment compounds wherein the 4-position substituent A" represents F, Cl, Br, I, CF₃, SCF₃, CN, CO₂R‴, and CONR‴₂ (B" represents H) are specifically identified. Those wherein A" represents Cl, Br, I, or CF₃ are usually more preferred. When the point of attachment is the 4-position, the moiety is substituted in one or both of the 3- and 5-positions. Such compounds wherein the 3- or 5-position substituent A" represents F, Cl, Br, I, CF₃, and CH₃ and the other 3- or 5-position substituent B" represents H, Cl, Br, F, CH₃, or OCH₃ are specifically identified. Pyrazolyl moieties wherein A" represents Cl, Br, I, or CF₃ and B" represents H are often preferred.

When Ar represents an indazolyl moiety, the moiety is attached to the sulfonamide nitrogen atom at the 3-position, has a methyl group in the 1-position, and is optionally mono-substituted with fluorine. Such compounds having a fluoro substituent in the 4-position are often preferred.

The term alkyl as used herein includes straight chain, branched chain, and cyclic moieties. Thus, typical alkyl groups are methyl, ethyl, 1-methylethyl, propyl, cyclopropyl and the like. Methyl and ethyl are often preferred. Typical alkyl groups singly to completely substituted with fluorine include trifluoromethyl, monofluoromethyl, 2,2,2-trifluoroethyl, 2,3-difluoropropyl, and the like; trifluoromethyl is often preferred. The term haloalkyl is used herein to denote alkyl singly to completely substituted with fluorine or chlorine and includes trifluoromethyl, dichloromethyl, 2,2-difluoro-2-chloroethyl, and the like; trifluoromethyl is often preferred. The term halogen includes fluorine, chlorine, bromine, and iodine.

The term "agriculturally acceptable salts" is employed herein to denote compounds wherein the acidic sulfonamide proton of the compound of Formula I is replaced by a cation which itself is neither herbicidal to crop plants being treated nor significantly deleterious to the applicator, the environment, or the ultimate user of any crop being treated. Suitable cations include, for example, those derived from alkali or alkaline earth metals and those derived from ammonia and amines. Preferred cations include sodium, potassium, magnesium, and aminium cations of the formula:

wherein R⁶, R⁷, and R⁸ each, independently represents hydrogen or (C₁–C₁₂)alkyl, (C₃–C₁₂)cycloalkyl, or (C₃–C₁₂)alkenyl, each of which is optionally substituted by one or more hydroxy, (C₁–C₈)alkoxy, (C₁–C₈)alkylthio or phenyl groups; provided that R⁶, R⁷, and R⁸ are sterically compatible. Additionally, any two of R⁶, R⁷, and R⁸ together may represent an aliphatic difunctional moiety containing 1 to 12 carbon atoms and up to two oxygen or sulfur atoms. Salts of the compounds of Formula I can be prepared by treatment of compounds of Formula I wherein V represents hydrogen with a metal hydroxide, such as sodium hydroxide, potassium hydroxide, or magnesium hydroxide, or an amine, such as ammonia, trimethylamine, hydroxyethylamine, bisallylamine, 2-butoxyethylamine, morpholine, cyclododecylamine, or benzylamine.

While each of the N-aryl[1,2,4]triazolo[1,5-a]pyridine-2-sulfonamide compounds encompassed by Formula I is within the scope of the invention, the degree of herbicidal activity and the spectrum of weed control obtained varies depending upon the substituents present and, consequently, certain of the compounds are preferred. The compounds that are preferred in any specific situation further depends on the identity of the undesirable vegetation to be controlled, climatic factors, whether total or selective vegetation control is desired, and other factors.

A listing of some typical compounds of the invention is given in Table 1. Some of the specifically preferred compounds of the invention include: N-(2,6-dichloro-3-methylphenyl)-5-methoxy-7-methyl[1,2,4]triazolo[1,5-a]pyridine-2-sulfonamide, N-(2,3-dimethyl-6-nitrophenyl)-5-methoxy-7-methyl[1,2,4]triazolo[1,5-a]pyridine-2-sulfonamide, N-(2-fluoro-4-methyl-3-pyridinyl)-5-methoxy-7-methyl[1,2,4]triazolo[1,5-a]pyridine-2-sulfonamide, N-(2-chloro-4-ethoxy-3-pyridinyl)-5-methoxy-7-methyl[1,2,4]triazolo[1,5-a]pyridine-2-sulfonamide, N-(2-chloro-4-methyl-3-pyridinyl)-5-methoxy-7-methyl[1,2,4]triazolo[1,5-a]pyridine-2-sulfonamide, N-(4-bromo-1-methyl-3-pyrazolyl)-5-methoxy-7-methyl[1,2,4]triazolo[1,5-a]pyridine-2-sulfonamide, N-(2-methyl-6-nitrophenyl)-5-ethoxy-7-methyl[1,2,4]triazolo[1,5-a]pyridine-2-sulfonamide, N-(2-methoxy-6-(trifluoromethyl)phenyl)-5-ethoxy-7-methyl[1,2,4]triazolo[1,5-a]pyridine-2-sulfonamide, N-(2,6-difluorophenyl)-8-chloro-5-methoxy[1,2,4]triazolo[1,5-a]pyridine-2-sulfonamide, N-(2-fluoro-4-methyl-3-pyridinyl)-8-chloro-5-methoxy[1,2,4]triazolo[1,5-a]pyridine-2-sulfonamide, N-(2-fluoro-4-methyl-3-pyridinyl)-7-chloro-5-methoxy[1,2,4]triazolo[1,5-a]pyridine-2-sulfonamide, N-(4-bromo-1-methyl-3-pyrazolyl)-7-chloro-5-methoxy[1,2,4]triazolo[1,5-a]pyridine-2-sulfonamide, N-(2-fluoro-4-methyl-3-pyridinyl)-7-chloro-5-ethoxy[1,2,4]triazolo[1,5-a]pyridine-2-sulfonamide, N-(4-bromo-1-methyl-3-pyrazolyl)-8-methoxy[1,2,4]triazolo[1,5-a]pyridine-2-sulfonamide, N-(4-bromo-1-methyl-3-pyrazolyl)-6-chloro-8-methoxy[1,2,4]triazolo[1,5-a]pyridine-2-sulfonamide, N-(2,6-dichlorophenyl)-6-bromo-8-methoxy[1,2,4]triazolo[1,5-a]pyridine-2-sulfonamide, N-(2-fluoro-4-methyl-3-pyridinyl)-6-bromo-8-methoxy[1,2,4]triazolol[5-a]pyridine-2-sulfonamide, N-(2-methyl-6-nitrophenyl)-7-methyl-5-(2,2,2-trifluoroethoxy)[1,2,4]triazolo[1,5-a]pyridine-2-sulfonamide, N-(2-methyl-6-nitrophenyl)-5-chloro-7-methyl-[1,2,4]triazolo[1,5-a]pyridine-2-sulfonamide, and N-(2-chloro-4-methoxy-3-pyridinyl)-5,7-dimethoxy[1,2,4]triazolo[1,5-a]pyridine-2-sulfonamide.

TABLE 1

N-ARYL[1,2,4]TRIAZOLO[1,5-A]PYRIDINE-2-SULFONAMIDE COMPOUNDS

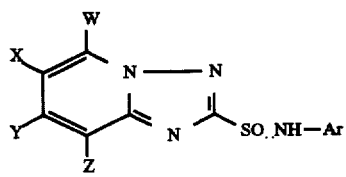

| Cpd. No. | W | X | Y | Z | Ar | Form | Melting point, °C. | %C calc. found | %H calc. found | %N calc. found |
|---|---|---|---|---|---|---|---|---|---|---|
| 1 | H | H | H | H | 2,6-dichlorophenyl | white powder | 269–270 | 42.0 41.9 | 2.35 2.22 | 16.3 16.3 |
| 2 | H | H | H | H | 2,6-difluorophenyl | white powder | 222–223 | 45.6 45.6 | 2.60 2.56 | 18.1 18.2 |
| 3 | H | H | H | H | 1-methyl-4-bromo-3-pyrazolyl | tan solid | 229–231 | 33.6 34.0 | 2.54 2.55 | 23.5 23.2 |
| 4 | H | H | $CH_3$ | H | 2,6-dichlorophenyl | tan powder | 232–234 | 43.7 44.0 | 2.82 2.87 | 15.7 15.5 |
| 5 | H | H | $CH_3$ | H | 2,6-difluorophenyl | white powder | 231–232 | 48.1 48.1 | 3.11 2.97 | 17.3 17.4 |
| 6 | H | H | $CH_3$ | H | 1-methyl-4-bromo-3-pyrazolyl | white solid | 238–240 | 35.7 35.8 | 2.72 3.00 | 22.7 22.6 |
| 7 | Cl | H | $CH_3$ | H | 2-fluoro-4-methyl-3-pyridinyl | yellow powder | 253–255 (d) | 44.0 44.2 | 2.84 3.09 | 19.7 19.7 |
| 8 | $OCH_3$ | H | $CH_3$ | H | 2-fluoro-4-methyl-3-pyridinyl | white powder | 202–204 (d) | 47.9 48.0 | 4.02 4.06 | 19.9 19.6 |
| 9 | $OCH_2CF_3$ | H | $CH_3$ | H | 2-fluoro-4-methyl-3-pyridinyl | white powder | 249–250 (d) | 43.0 43.2 | 3.12 3.21 | 16.7 16.6 |
| 10 | Cl | H | $CH_3$ | H | 1-methyl-4-bromo-3-pyrazolyl | tan solid | 262–264 | 32.6 30.7 | 2.48 2.59 | 20.7 20.7 |
| 11 | Cl | H | $CH_3$ | H | 2,6-dibromophenyl | white powder | 256–259 | 32.5 32.8 | 1.89 2.06 | 11.7 11.7 |
| 12 | Cl | H | $CH_3$ | H | 2-methyl-6-methoxy-carbonylphenyl | white solid | 198–202 | 48.7 48.6 | 3.83 4.20 | 14.2 14.0 |
| 13 | $OCH_2CH_3$ | H | $CH_3$ | H | 2-fluoro-4-methyl-3-pyridinyl | white powder | 206–208.5 | 49.3 49.7 | 4.41 4.44 | 19.2 19.1 |
| 14 | Cl | H | $CH_3$ | H | 2-fluoro-6-methoxy-carbonylphenyl | mauve powder | 216–219 | 45.2 45.0 | 3.03 3.40 | 14.1 14.0 |
| 15 | Cl | H | $CH_3$ | H | 1-methyl-3-indazolyl | tan solid | 267–269 | 46.7 46.5 | 3.66 3.52 | 21.8 21.8 |
| 16 | $CH_3$ | H | $CH_3$ | H | 1-methyl-4-bromo-3-pyrazolyl | tan powder | 229–232 (d) | 37.4 38.1 | 3.40 3.62 | 21.8 21.6 |
| 17 | $CH_3$ | H | $CH_3$ | H | 2,6-dichlorophenyl | white powder | 250–252 | 45.3 44.9 | 3.26 3.49 | 15.1 14.8 |
| 18 | $CH_3$ | H | $CH_3$ | H | 2,6-difluorophenyl | lt. tan powder | 207–209 | 49.7 49.4 | 3.58 3.80 | 16.6 16.4 |
| 19 | $OCH_3$ | H | $CH_3$ | H | 1-methyl-4-bromo-3-pyrazolyl | white solid | 251 (d) | 35.9 36.0 | 3.27 3.05 | 20.9 20.9 |
| 20 | $OCH_3$ | H | $CH_3$ | H | 2-bromo-6-chloro-phenyl | white solid | >265 | 39.0 37.9 | 2.80 2.75 | 13.0 12.5 |
| 21 | $OCH_2CH_3$ | H | $CH_3$ | H | 2-bromo-6-chloro-phenyl | white solid | 279 | 40.4 40.4 | 3.17 3.08 | 12.6 12.6 |
| 22 | Cl | H | $CH_3$ | H | 2-bromo-6-fluoro-phenyl | tan solid | 226 | 37.2 37.1 | 2.16 1.86 | 13.4 13.3 |
| 23 | $OCH_3$ | H | $CH_3$ | H | 2-bromo-6-flouro-phenyl | white solid | 253 (d) | 40.5 40.3 | 2.91 3.13 | 13.5 13.7 |
| 24 | $OCH_2CH_3$ | H | $CH_3$ | H | 2-bromo-6-fluoro-phenyl | white solid | 259 (d) | 42.0 41.9 | 3.29 3.44 | 13.1 13.0 |
| 25 | Cl | H | $CH_3$ | H | 2-methoxy-6-(tri-fluoromethyl)phenyl | white solid | 231–232.5 | 42.8 42.9 | 2.87 3.00 | 13.3 13.5 |
| 26 | Cl | H | $CH_3$ | H | 2,6-dichloro-3-methylphenyl | white solid | 269–271 | 41.5 41.5 | 2.73 2.92 | 13.8 14.0 |
| 27 | Cl | H | $CH_3$ | H | 2,6-difluoro-3-methylphenyl | white solid | 224–226 | 45.1 45.1 | 2.97 2.62 | 15.0 15.2 |
| 28 | $OCH_3$ | H | $CH_3$ | H | 2-methoxy-6-(tri-fluoromethyl)phenyl | white solid | 243–245 | 46.2 46.1 | 3.63 3.58 | 13.5 13.4 |
| 29 | $OCH_3$ | H | $CH_3$ | H | 1-methyl-3-indazolyl | tan solid | 247–248 | 51.7 51.9 | 4.07 3.87 | 22.6 22.4 |
| 30 | $OCH_3$ | H | $CH_3$ | H | 2-chloro-6-methoxy-phenyl | white solid | 145–146 | 47.1 47.0 | 3.95 3.97 | 14.6 14.6 |
| 31 | $OCH_3$ | H | $CH_3$ | H | 2,6-dichloro-3-methylphenyl | grey powder | 150–151 | 44.9 45.2 | 3.52 3.58 | 14.0 14.0 |
| 32 | $OCH_3$ | H | $CH_3$ | H | 2,6-difluoro-3- | white | 144–145 | 48.9 | 3.83 | 15.2 |

TABLE 1-continued

N-ARYL[1,2,4]TRIAZOLO[1,5-A]PYRIDINE-2-SULFONAMIDE COMPOUNDS

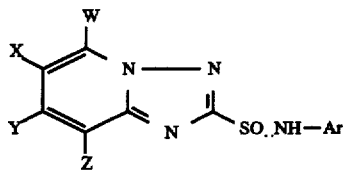

| Cpd. No. | W | X | Y | Z | Ar | Form | Melting point, °C. | % C calc. found | % H calc. found | % N calc. found |
|---|---|---|---|---|---|---|---|---|---|---|
| 33 | OCH₂CH₃ | H | CH₃ | H | 2-chloro-6-methoxy-phenyl | methylphenyl powder grey powder | 232–235 | 48.9 48.3 48.3 | 3.78 4.32 4.71 | 15.3 14.1 14.0 |
| 34 | OCH₂CH₃ | H | CH₃ | H | 2-methoxy-6-(tri-fluoromethyl)phenyl | white powder | 246–247 | 47.4 47.4 | 3.98 4.03 | 13.0 13.0 |
| 35 | OCH₂CH₃ | H | CH₃ | H | 2,6-dichloro-3-methylphenyl | white powder | 260–262 | 46.3 46.2 | 3.88 3.69 | 13.5 13.4 |
| 36 | OCH₂CH₃ | H | CH₃ | H | 2,6-difluoro-3-methylphenyl | white powder | 240–243 | 50.3 50.2 | 4.22 4.38 | 14.7 14.6 |
| 37 | OCH₂CH₃ | H | CH₃ | H | 2-methyl-6-nitro-phenyl | white solid | 256 (d) | 49.1 49.1 | 4.38 4.42 | 17.9 18.1 |
| 38 | OCH₂CH₃ | H | CH₃ | H | 2,3-dimethyl-6-nitro-phenyl | yellow solid | 255–256 (d) | 50.4 50.4 | 4.72 4.88 | 17.3 17.2 |
| 39 | OCH₂CH₃ | H | CH₃ | H | 2-fluoro-5-methyl-phenyl | white crystals | 238–239 (d) | 52.7 52.5 | 4.70 4.62 | 15.4 15.5 |
| 40 | OCH₂CH₃ | H | CH₃ | H | 2-chloro-6-methyl-phenyl | white solid | 253–255 (d) | 50.5 50.5 | 4.50 4.58 | 14.7 14.9 |
| 41 | OCH₂CH₃ | H | CH₃ | H | 2-(trifluoromethyl)-phenyl | white solid | 203–204.5 | 48.0 47.9 | 3.78 3.96 | 13.8 13.9 |
| 42 | OCH₃ | H | CH₃ | H | 2-methyl-6-nitro-phenyl | yellow powder | 231–233 | 47.7 48.1 | 4.01 4.29 | 18.6 18.6 |
| 43 | OCH₃ | H | CH₃ | H | 2,3-dimethyl-6-nitro-phenyl | yellow powder | 258–260 | 49.1 49.2 | 4.38 4.60 | 17.9 18.0 |
| 44 | OCH₃ | H | CH₃ | H | 2-flouro-5-methyl-phenyl | white solid | 229–230 | 51.4 51.7 | 4.32 4.56 | 16.0 16.2 |
| 45 | OCH₃ | H | CH₃ | H | 2-(trifluoromethyl)-phenyl | white powder | 230–231 | 46.6 46.4 | 3.39 3.52 | 14.5 14.6 |
| 46 | Cl | H | CH₃ | H | 2-fluoro-5-methyl-phenyl | white solid | 213–214 | 47.4 47.5 | 3.41 3.44 | 15.8 15.8 |
| 47 | OCH₃ | H | CH₃ | H | 2-chloro-6-methyl-phenyl | white solid | 253–255 | 49.1 49.3 | 4.12 4.24 | 15.3 15.3 |
| 48 | OCH₂CF₃ | H | CH₃ | H | 2-methyl-6-nitro-phenyl | white solid | 245–247 (d) | 43.2 43.3 | 3.17 3.44 | 15.7 15.7 |
| 49 | OCH₂CF₃ | H | CH₃ | H | 2,3-dimethyl-6-nitro-phenyl | yellow | 242–243 (d) | 44.5 44.4 | 3.51 3.72 | 15.2 15.1 |
| 50 | OCH₂CF₃ | H | CH₃ | H | 2-chloro-6-methyl-phenyl | white solid | 215–217 | 44.2 44.0 | 3.25 3.49 | 12.9 12.8 |
| 51 | OCH₃ | H | CH₃ | H | 2-chloro-4-methyl-3-pyridinyl | tan powder | 209–210 (d) | 45.7 46.0 | 3.84 4.07 | 19.0 18.7 |
| 52 | Cl | H | CH₃ | H | 2-chloro-4-methoxy-3-pyridinyl | yellow powder | 219–221 (d) | 40.2 40.6 | 2.86 3.08 | 18.0 18.0 |
| 53 | OCH₃ | H | CH₃ | H | 2-chloro-4-methoxy-3-pyridinyl | white powder | 216–217 (d) | 43.8 43.8 | 3.68 3.55 | 18.3 17.9 |
| 54 | Cl | H | CH₃ | H | 2-chloro-4-methyl-3-pyridinyl | white powder | 255–257 (d) | 42.0 42.3 | 2.98 2.92 | 18.8 19.0 |
| 55 | OCH₂CF₃ | H | CH₃ | H | 2-chloro-6-iodophenyl | white powder | 248 | 33.0 32.9 | 2.03 1.94 | 10.3 10.1 |
| 56 | OCH₂CF₃ | H | CH₃ | H | 2-fluoro-6-methoxy-carbonylphenyl | tan solid | 182 | 44.2 44.1 | 3.06 2.88 | 12.1 12.0 |
| 57 | OCH₂CH₃ | H | CH₃ | H | 2-fluoro-6-ethoxy-carbonylphenyl | tan solid | 212 | 50.0 51.0 | 4.20 4.46 | 13.7 13.3 |
| 58 | OCH₂CH₃ | H | CH₃ | H | 2,6-dichlorophenyl | off-white solid | >275 | 44.9 42.6 | 3.52 3.55 | 14.0 13.3 |
| 59 | OCH₂CF₃ | H | CH₃ | H | 2,6-dibromophenyl | white powder | 262 | 33.1 33.0 | 2.04 1.89 | 10.3 10.2 |
| 60 | OCH₂CF₃ | H | CH₃ | H | 2,6-dichlorophenyl | white powder | | 39.6 39.8 | 2.44 2.34 | 12.3 12.3 |
| 61 | OCH₂CH₃ | H | CH₃ | H | 2,6-difluorophenyl | tan powder | 254–256 | 48.9 48.7 | 3.83 4.03 | 15.2 15.2 |
| 62 | OCH₂CF₃ | H | CH₃ | H | 2,6-fluorophenyl | white powder | 267–269 | 42.7 39.5 | 2.63 2.57 | 13.3 12.3 |
| 63 | OCH₂CF₃ | H | CH₃ | H | 2-methoxy-6-(tri-fluoromethyl)phenyl | off-white powder | 235–237 (d) | 42.2 42.2 | 2.91 2.80 | 11.5 11.6 |

TABLE 1-continued

N-ARYL[1,2,4]TRIAZOLO[1,5-A]PYRIDINE-2-SULFONAMIDE COMPOUNDS

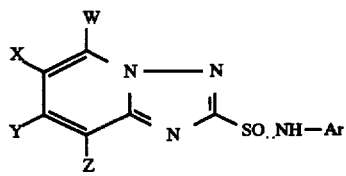

| Cpd. No. | W | X | Y | Z | Ar | Form | Melting point, °C. | % C calc. found | % H calc. found | % N calc. found |
|---|---|---|---|---|---|---|---|---|---|---|
| 64 | OCH$_2$CF$_3$ | H | CH$_3$ | H | 4-bromo-1-methyl-5-pyrazolyl | tan solid | 193–197 | 33.3 33.7 | 2.58 2.54 | 17.9 18.1 |
| 65 | Cl | H | Cl | H | 2,6-dichlorophenyl | lt. tan powder | 246–248 | 35.0 34.8 | 1.47 1.25 | 13.6 13.5 |
| 66 | OCH$_3$ | H | Cl | H | 2,6,-dichlorophenyl | lt. tan powder | 232–243 (d) | 38.3 38.3 | 2.22 2.12 | 13.7 13.7 |
| 67 | OCH$_2$CH$_3$ | H | CH$_3$ | H | 2-chloro-6-fluoro-phenyl | white solid | >265 | 46.8 47.0 | 3.67 3.79 | 14.6 14.5 |
| 68 | Cl | H | CH$_3$ | H | 2-bromo-6-chloro-phenyl | white solid | 185–186 | 35.8 35.7 | 2.08 2.05 | 12.9 12.7 |
| 69 | OCH$_3$ | H | CH$_3$ | H | 2-chloro-6-fluoro-phenyl | off-white solid | 245 | 45.4 45.5 | 3.26 3.42 | 15.1 14.9 |
| 70 | OCH$_2$CF$_3$ | H | CH$_3$ | H | 2-bromo-6-fluoro-phenyl | white powder | >300 | 37.3 37.4 | 2.29 2.15 | 6.64 6.75 |
| 71 | OCH$_2$CF$_3$ | H | CH$_3$ | H | 2-chloro-6-fluoro-phenyl | white solid | 248 | 41.1 41.0 | 2.53 2.46 | 12.8 12.8 |
| 72 | OCH$_2$CH$_3$ | H | CH$_3$ | H | 2-chloro-6-iodophenyl | white powder | >263 | 36.6 36.7 | 2.86 2.58 | 11.4 11.4 |
| 73 | OCH$_3$ | H | CH$_3$ | H | 2-chloro-6-iodophenyl | white powder | >247 | 35.1 35.4 | 2.53 2.23 | 11.7 11.5 |
| 74 | Cl | H | CH$_3$ | H | 2-methyl-6-nitro-phenyl | yellow powder | 256–258 | 44.0 44.1 | 3.17 3.23 | 18.3 18.6 |
| 75 | Cl | H | CH$_3$ | H | 2,3-dimethyl-6-nitro-phenyl | yellow solid | 281–283 | 45.5 45.7 | 3.57 3.73 | 17.7 17.7 |
| 76 | Cl | H | CH$_3$ | H | 2-chloro-6-methyl-phenyl | white solid | 258–260 | 45.3 45.2 | 3.26 3.21 | 15.1 15.1 |
| 77 | Cl | H | CH$_3$ | H | 2-(trifluoromethyl)-phenyl | white solid | 196–198 | 43.0 42.9 | 2.58 2.72 | 14.3 14.5 |
| 78 | Cl | H | CH$_3$ | H | 2,6-dichlorophenyl | white powder | 257–258 (d) | 39.9 39.8 | 2.32 2.35 | 14.3 14.3 |
| 79 | Cl | H | CH$_3$ | H | 2,6-difluorophenyl | yellow powder | 213–214 | 43.5 43.5 | 2.53 2.51 | 15.6 15.7 |
| 80 | OCH$_3$ | H | CH$_3$ | H | 2,6-dichlorophenyl | white powder | 269–270 (d) | 43.4 43.3 | 3.13 3.13 | 14.5 14.4 |
| 81 | OCH$_3$ | H | CH$_3$ | H | 2,6-difluorophenyl | tan powder | 248–249 (d) | 47.5 47.4 | 3.41 3.48 | 15.8 15.8 |
| 82 | OCH$_3$ | H | CH$_3$ | H | 2-fluoro-6-methoxy-carbonylphenyl | mauve solid | 220–221 (d) | 48.7 48.9 | 3.83 3.82 | 14.2 14.2 |
| 83 | OCH$_3$ | H | CH$_3$ | H | 2,6-dibromophenyl | white solid | 270 (d) | 35.3 35.5 | 2.54 2.72 | 11.8 11.8 |
| 84 | OCH$_2$CH$_3$ | H | CH$_3$ | H | 2,6-dibromophenyl | white powder | 271 (d) | 36.8 37.8 | 2.88 3.17 | 11.4 11.5 |
| 85 | OCH$_3$ | H | CH$_3$ | H | 2-methyl-6-methoxy-carbonylphenyl | off-white solid | 212–214 | 52.3 52.4 | 4.65 4.82 | 14.4 14.2 |
| 86 | OCH$_3$ | H | CH$_3$ | H | 4-bromo-1-methyl-3-pyrazolyl | tan solid | 263–264 | 35.9 36.0 | 3.27 3.59 | 21.0 20.8 |
| 87 | Cl | H | CH$_3$ | H | 2-chloro-6-methoxy-phenyl | cream solid | 240–243 | 43.4 43.6 | 3.12 3.38 | 14.5 14.7 |
| 88 | OCH$_3$ | H | OCH$_3$ | H | 2,6-dichlorophenyl | yellow powder | 252–253 (d) | 41.7 41.8 | 3.00 2.67 | 13.9 13.6 |
| 89 | H | CH$_3$ | H | Br | 2,6-dichlorophenyl | off-white solid | 240–242 (d) | 35.8 35.5 | 2.08 1.88 | 12.9 13.2 |
| 90 | H | CH$_3$ | H | OCH$_3$ | 2,6-dichlorophenyl | tan solid | 232 | 43.4 42.3 | 3.12 3.51 | 14.5 14.0 |
| 91 | OCH$_3$ | H | CH$_3$ | H | 2-bromo-6-methoxy-carbonylphenyl | off-white solid | 225 | 42.2 42.0 | 3.32 3.05 | 12.3 12.5 |
| 92 | H | CH$_3$ | H | Br | 2-fluoro-6-methoxy-carbonylphenyl | pink solid | 198 (d) | 40.6 40.4 | 2.73 2.53 | 12.6 12.6 |
| 93 | Cl | H | CH$_3$ | H | 2-fluoro-5-methyl-3-pyridinyl | white powder | 208–209 | 43.9 43.9 | 3.12 3.41 | 19.7 19.7 |
| 94 | OCH$_3$ | H | CH$_3$ | H | 2-fluoro-5-methyl-3-pyridinyl | white powder | 237–238 (d) | 47.9 47.6 | 4.02 3.84 | 19.9 19.9 |
| 95 | H | Br | H | Br | 2,6-dichlorophenyl | brown | | | | |

TABLE 1-continued

N-ARYL[1,2,4]TRIAZOLO[1,5-A]PYRIDINE-2-SULFONAMIDE COMPOUNDS

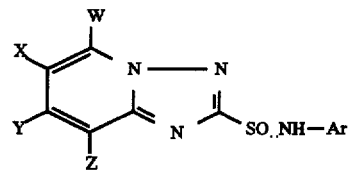

| Cpd. No. | W | X | Y | Z | Ar | Form | Melting point, °C. | % C calc. found | % H calc. found | % N calc. found |
|---|---|---|---|---|---|---|---|---|---|---|
| 96 | H | Br | H | OCH₃ | 2,6-dichlorophenyl | tan powder | >300 | 34.5 35.5 | 2.01 2.14 | 12.4 12.0 |
| 97 | H | H | H | OCH₃ | 2,6-dichlorophenyl | white powder | 119–121 | 41.8 41.5 | 2.70 2.42 | 15.0 13.9 |
| 98 | OCH₃ | H | Cl | H | 2-fluoro-6-methoxy-carbonylphenyl | white powder | 221–222 | 43.5 43.1 | 2.92 2.90 | 13.5 13.5 |
| 99 | Cl | H | CH₃ | H | 4-iodo-1-methyl-3-pyrazolyl | tan solid | 249–251 | 29.2 29.0 | 2.23 2.16 | 18.6 18.4 |
| 100 | Cl | H | Cl | H | 2-fluoro-6-methoxy-carbonylphenyl | lt. tan powder | 182–183 | 40.1 39.9 | 2.16 2.05 | 13.4 13.1 |
| 101 | OCH₃ | H | CH₃ | H | 4-iodo-1-methyl-3-pyrazolyl | white solid | 199 (d) | 30.5 30.9 | 2.72 3.24 | 17.7 18.0 |
| 102 | Cl | H | Cl | H | 2-fluoro-4-methyl-3-pyridinyl | lt. tan powder | 221–223 | 38.3 38.4 | 2.14 2.29 | 18.6 18.6 |
| 103 | OCH₃ | H | Cl | H | 2-fluoro-4-methyl-3-pyridinyl | lt. tan powder | 213–214 (d) | 42.0 42.3 | 2.98 2.70 | 18.8 18.7 |
| 104 | OCH₂CH₃ | H | Cl | H | 2-fluoro-4-methyl-3-pyridinyl | lt. tan powder | 184–185 (d) | 43.6 44.0 | 3.40 3.57 | 18.2 17.8 |
| 105 | Cl | H | Cl | H | 4-bromo-1-methyl-3-pyrazolyl | lt. tan powder | 266–267 (d) | 28.2 28.0 | 1.66 1.35 | 19.7 19.5 |
| 106 | OCH₃ | H | Cl | H | 4-bromo-1-methyl-3-pyrazolyl | white powder | 257–258 (d) | 31.3 31.3 | 2.39 2.06 | 19.9 19.9 |
| 107 | Cl | H | Cl | H | 2,6-difluorophenyl | white powder | 214–215 | 38.1 38.2 | 1.59 1.56 | 14.8 14.9 |
| 108 | OCH₃ | H | Cl | H | 2,6-difluorophenyl | white powder | 240–241 (d) | 41.7 41.4 | 2.42 2.35 | 15.0 14.8 |
| 109 | Cl | Br | H | OCH₃ | 2,6-difluorophenyl | pale pink powder | 262 | 34.4 34.7 | 1.78 1.64 | 12.4 12.1 |
| 110 | H | Br | H | OCH₃ | 4-bromo-1-methyl-3-pyrazolyl | brown powder | >300 | 28.3 32.9 | 2.16 2.15 | 18.0 15.5 |
| 111 | H | Br | H | OCH₃ | 2-fluoro-4-methyl-3-pyridinyl | pink powder | 198–200 | 37.5 37.4 | 2.66 2.36 | 16.8 15.3 |
| 112 | H | H | Cl | H | 2,6-difluorophenyl | white powder | 276–278 (d) | 41.8 41.7 | 2.05 2.30 | 16.3 16.3 |
| 113 | H | H | Cl | H | 2-fluoro-6-methoxy-carbonylphenyl | white powder | 205–207 | 43.8 43.7 | 2.62 2.74 | 14.6 14.7 |
| 114 | H | H | OCH₃ | H | 2,6-difluorophenyl | white powder | 231–232 | 45.9 45.6 | 2.96 2.97 | 16.4 16.4 |
| 115 | H | Cl | H | OCH₃ | 2,6-difluorophenyl | tan solid | 223–225 (d) | 41.7 41.9 | 2.42 2.36 | 15.0 14.7 |
| 116 | H | Cl | H | OCH₃ | 2-fluoro-4-methyl-3-pyridinyl | cream solid | 212 | 42.0 41.4 | 2.98 2.74 | 18.8 27.8 |
| 117 | H | Cl | H | OCH₃ | 4-bromo-1-methyl-3-pyrazolyl | rust solid | 225 | 31.3 31.4 | 2.39 2.07 | 19.9 17.5 |
| 118 | OCH₃ | Br | H | OCH₃ | 2,6-difluorophenyl | purple solid | 222–223 | 37.4 38.9 | 2.37 1.83 | 12.5 12.8 |
| 119 | Cl | H | CH₃ | H | 5-chloro-2-fluoro-3-pyridinyl | grey powder | 225–226 (d) | 38.3 38.8 | 2.14 1.94 | 18.6 18.3 |
| 120 | OCH₃ | H | CH₃ | H | 5-chloro-2-fluoro-3-pyridinyl | white powder | 262–264 | 42.0 41.9 | 2.98 2.93 | 18.8 18.8 |
| 121 | OCH₃ | H | CH₃ | H | 1-methyl-4-(tri-fluoromethylthio)-3-pyrazolyl | white solid | 191–193 | 37.0 37.3 | 3.10 2.91 | 19.9 19.8 |
| 122 | Cl | H | CH₃ | H | 2-methoxy-6-methoxy-carbonylphenyl | purple powder | 213–216 | 46.8 47.0 | 3.68 3.92 | 13.6 13.7 |
| 123 | OCH₃ | H | CH₃ | H | 2-methoxy-6-methoxy-carbonylphenyl | tan powder | 219–221 | 50.2 50.0 | 4.46 4.67 | 13.8 13.7 |
| 124 | Cl | H | CH₃ | H | 4-methyl-3-pyridinyl | white powder | 223–224 (d) | 46.2 46.1 | 3.58 3.89 | 20.7 20.6 |
| 125 | OCH₃ | H | CH₃ | H | 4-methyl-3-pyridinyl | lt. grey powder | 209–210 (d) | 50.4 49.3 | 4.54 4.95 | 21.0 19.8 |
| 126 | H | CF₃ | H | OCH₃ | 2,6-difluorophenyl | off-white | 172–173 | 41.2 | 2.22 | 13.7 |

TABLE 1-continued

N-ARYL[1,2,4]TRIAZOLO[1,5-A]PYRIDINE-2-SULFONAMIDE COMPOUNDS

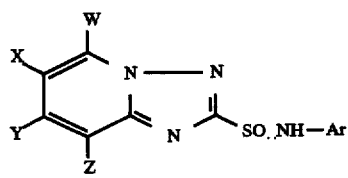

| Cpd. No. | W | X | Y | Z | Ar | Form | Melting point, °C. | % C calc. found | % H calc. found | % N calc. found |
|---|---|---|---|---|---|---|---|---|---|---|
| | | | | | | solid | (d) | 41.6 | 2.26 | 13.6 |
| 127 | H | CF₃ | H | OCH₃ | 2-fluoro-4-methyl-3-pyridinyl | off-white solid | 238 (d) | 41.5 41.6 | 2.74 2.67 | 17.3 17.1 |
| 128 | H | CF₃ | H | OCH₃ | 4-bromo-1-methyl-3-pyrazolyl | orange solid | 198 | 31.7 32.4 | 2.22 2.16 | 18.5 18.1 |
| 129 | OCH₃ | H | CH₃ | H | 4-iodo-1-methyl-3-pyrazolyl | tan solid | 201–203 | 36.2 36.0 | 2.92 2.74 | 18.8 19.0 |
| 130 | OCH₂CH₃ | H | CH₃ | H | 4-bromo-i-methyl-3-pyrazolyl | tan powder | 245–247 | 37.6 37.8 | 3.64 3.75 | 20.2 19.9 |
| 131 | Cl | H | H | H | 2,6-difluorophenyl | tan powder | 255–256 (d) | 41.8 41.8 | 2.05 2.00 | 16.3 16.4 |
| 132 | OCH₃ | H | H | H | 2,6-difluorophenyl | tan powder | 255–256 (d) | 45.9 46.1 | 2.96 2.92 | 16.5 16.6 |
| 133 | OCH₂CH₃ | H | H | H | 2,6-difluorophenyl | tan powder | 263–264 (d) | 47.5 47.6 | 3.42 3.04 | 15.8 16.0 |
| 134 | OCH₂—CH₂OCH₃ | H | CH₃ | H | 2,6-difluorophenyl | tan powder | 217–220 | 48.0 48.2 | 3.89 4.05 | 14.0 14.1 |
| 135 | OCH₂—CH₂F | H | CH₃ | H | 2,6-difluorophenyl | tan powder | 245–247 | 46.6 46.9 | 3.39 3.43 | 14.5 14.5 |
| 136 | OCH₂CH₃ | H | H | H | 2-fluoro-4-methyl-3-pyridinyl | lt. tan powder | 196–197 (d) | 47.9 48.0 | 4.02 4.27 | 15.8 16.0 |
| 137 | Br | H | H | H | 4-bromo-1-methyl-3-pyrazolyl | tan powder | 246–247 (d) | 27.5. 27.8 | 1.85 1.69 | 19.3 19.0 |
| 138 | OCH₃ | H | H | H | 4-bromo-1-methyl-3-pyrazolyl | tan powder | 233–234 (d) | 34.1 34.2 | 2.86 3.03 | 21.7 21.6 |
| 139 | OCH₂CH₃ | H | H | H | 4-bromo-1-methyl-3-pyrazolyl | tan powder | 230–231 (d) | 35.9 36.1 | 3.27 3.58 | 21.0 21.0 |
| 140 | OCH₃ | H | H | H | 2-fluoro-4-methyl-3-pyridinyl | lt. tan powder | 226–227 (d) | 46.3 46.2 | 3.59 3.90 | 20.8 20.7 |
| 141 | Br | H | H | H | 2-fluoro-4-methyl-3-pyridinyl | brown powder | 233–234 (d) | 37.3 37.3 | 2.35 2.66 | 18.1 18.4 |
| 142 | H | CF₃ | H | F | 4-bromo-1-methyl-3-pyrazolyl | orange solid | 224–227 (d) | 29.8 30.8 | 1.59 1.11 | 7.23 6.62 |
| 143 | H | CF₃ | H | F | 2,6-difluorophenyl | yellow solid | 136–137 | 39.4 39.5 | 1.53 1.20 | 14.1 13.9 |
| 144 | H | CF₃ | H | F | 4-methyl-3-pyridinyl | tan powder | 172–173 | 39.7 40.1 | 2.05 1.94 | 17.8 17.8 |
| 145 | H | Cl | H | OCH₃ | 2-bromo-6-methoxycarbonylphenyl | brown powder | 173–175 (d) | 37.9 38.0 | 2.54 2.35 | 11.8 11.8 |
| 146 | H | Cl | H | OCH₃ | 2-chloro-4-methyl-3-pyridinyl | brown powder | 175–176 (d) | 40.2 40.0 | 2.86 2.73 | 18.0 16.2 |
| 147 | H | Cl | H | OCH₃ | 2-chloro-4-methoxy-3-pyridinyl | brown powder | 175–178 (d) | 38.6 38.7 | 2.74 2.44 | 17.3 16.4 |
| 148 | OCH₃ | H | CH₃ | H | 4-methoxycarbonyl-3-pyridinyl | tan solid | 181–183 (d) | 47.7 47.8 | 4.0i 4.20 | 18.6 18.6 |
| 149 | Cl | H | CH₃ | H | 4-methoxycarbonyl-3-pyridinyl | tan solid | 168–170 | 44.0 43.8 | 3.17 3.28 | 18.3 18.3 |
| 150 | OCH₃ | H | CH₃ | H | 4-carboxy-3-pyridinyl | white solid | 254–256 (d) | 46.3 46.0 | 3.61 3.31 | 19.3 19.0 |
| 151 | OCH₃ | H | CH₃ | H | 4-fluoro-1-methyl-3-indazolyl | tan solid | 147–149 (d) | 49.2 49.1 | 3.87 4.12 | 21.5 21.4 |
| 152 | OCH₂—CH₂Cl | H | CH₃ | H | 2,6-difluorophenyl | tan powder | 135–145 | 46.9 44.4 | 3.67 3.00 | 14.6 13.7 |
| 153 | OC₃H₇(n) | H | CH₃ | H | 2,6-difluorophenyl | tan powder | 242–245 | 50.3 50.3 | 4.22 4.35 | 14.7 14.5 |
| 154 | H | Cl | H | OCH₃ | 4-iodo-1-methyl-3-pyrazolyl | brown powder | 195–200 (d) | 28.2 30.7 | 2.15 2.32 | 17.9 17.2 |
| 155 | H | Cl | H | OCH₂CH₃ | 4-bromo-1-methyl-3-pyrazolyl | orange powder | 192–195 (d) | 33.1 33.4 | 2.78 2.73 | 19.3 18.1 |
| 156 | OCH₃ | H | CH₃ | H | 1-methyl-3-(trifluoromethyl)-4-pyrazolyl | tan solid | 140–142 (d) | | | |
| 157 | H | Cl | H | OCH₂CH₃ | 2-fluoro-4-methyl-3- | brown | 153–155 | 43.6 | 3.40 | 18.2 |

TABLE 1-continued

N-ARYL[1,2,4]TRIAZOLO[1,5-A]PYRIDINE-2-SULFONAMIDE COMPOUNDS

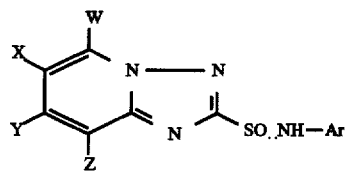

| Cpd. No. | W | X | Y | Z | Ar | Form | Melting point, °C. | % C calc. found | % H calc. found | % N calc. found |
|---|---|---|---|---|---|---|---|---|---|---|
| 158 | H | Cl | H | OCH₂CH₃ | 2,6-difluorophenyl | brown powder | 168–170 (d) | 43.5 41.8 41.9 | 3.28 2.25 2.51 | 17.0 13.9 14.1 |
| 159 | OCH₃ | H | Cl | H | 4-methoxycarbonyl-3-pyridinyl | brown powder | 167–172 | 42.3 42.3 | 3.04 3.14 | 17.6 16.5 |
| 160 | OCH₃ | H | CH₃ | H | 2-chloro-4-ethoxy-3-pyridinyl | white solid | 215–216 | 45.3 45.3 | 4.05 3.76 | 17.6 17.6 |
| 161 | OC₃H₇(i) | H | Cl | H | 2-chloro-4-ethoxy-3-pyridinyl | tan solid | 203–204 | 47.9 48.0 | 4.73 5.06 | 16.4 16.2 |
| 162 | H | H | H | Cl | 2,6-difluorophenyl | white powder | 263–265 | 41.8 41.6 | 2.05 2.14 | 16.3 16.2 |
| 163 | H | H | H | Cl | 4-bromo-1-methyl-3-pyrazolyl | white powder | 272–273 (d) | 30.7 30.4 | 2.06 2.06 | 21.5 21.1 |
| 164 | H | H | H | Cl | 2-fluoro-4-methyl-3-pyridinyl | yellow powder | 213–216 | 42.2 41.9 | 2.65 2.99 | 20.5 20.4 |
| 165 | H | H | H | OCH₃ | 2,6-difluorophenyl | white powder | 254–255 | 45.9 45.9 | 2.96 2.55 | 16.5 16.4 |
| 166 | H | H | H | OCH₃ | 4-bromo-1-methyl-3-pyrazolyl | off-white powder | 214–216 (d) | 34.1 34.0 | 2.86 3.04 | 21.7 21.5 |
| 167 | H | H | H | OCH₃ | 2-fluoro-4-methyl-3-pyridinyl | white powder | 204–206 | 46.3 43.8 | 3.59 3.17 | 20.8 19.1 |
| 168 | OCH₃ | H | Cl | H | 4-iodo-1-methyl-3-pyrazolyl | white powder | 222–226 (d) | 28.2 28.6 | 2.15 2.14 | 17.9 18.1 |
| 169 | OCH₃ | H | Cl | H | 2-chloro-4-methyl-3-pyridinyl | tan powder | 197–199 | 40.2 40.9 | 2.86 2.65 | 18.0 16.2 |
| 170 | OCH₃ | H | Cl | H | 2-chloro-4-methoxy-3-pyridinyl | white powder | 212–214 (d) | 38.6 39.6 | 2.74 3.35 | 17.3 15.1 |
| 171 | OCH₃ | H | Cl | H | 2-methyl-6-methoxycarbonylphenyl | white powder | 190–192 | 46.8 46.7 | 3.68 3.98 | 13.6 13.5 |
| 172 | H | Cl | H | OC₃H₇(n) | 4-bromo-1-methyl-3-pyrazolyl | yellow solid | 185–187 | 34.7 34.9 | 3.14 3.31 | 18.7 18.1 |
| 173 | H | Cl | H | OC₃H₇(n) | 2-fluoro-4-methyl-3-pyridinyl | off-white solid | 203–204 | 45.1 45.3 | 3.78 3.60 | 17.5 17.1 |
| 174 | Cl | H | CH₃ | H | 2-fluoro-4-methyl-3-pyridinyl | white solid | 223–225 | 45.5 45.5 | 3.54 3.37 | 18.9 18.6 |
| 175 | Cl | H | CH₃ | H | 4-bromo-1-methyl-3-pyrazolyl | tan powder | 240–242 (d) | 33.1 33.8 | 2.78 3.04 | 19.3 18.9 |
| 176 | Cl | H | CH₃ | H | 2,6-difluorophenyl | tan powder | 234–236 (d) | 42.2 42.3 | 3.07 2.85 | 13.8 14.4 |
| 177 | OC₃H₇(n) | H | Cl | H | 2,6-difluorophenyl | white powder | 199–200 (d) | 44.7 44.7 | 3.25 3.24 | 13.9 13.6 |
| 178 | OCH₃ | H | CH₃ | H | 2-fluoro-4-ethyl-3-pyridinyl | white powder | 221–222 (d) | 49.3 49.5 | 4.41 4.23 | 19.2 19.1 |
| 179 | H | Cl | H | OC₃H₇(i) | 2,6-difluorophenyl | yellow solid | 168–170 | 44.7 44.8 | 3.25 3.25 | 13.9 13.5 |
| 180 | H | Cl | H | OC₃H₇(i) | 2-fluoro-4-methyl-3-pyridinyl | yellow solid | 228–230 (d) | 45.1 45.1 | 3.78 3.76 | 17.2 16.6 |
| 181 | H | Cl | H | OC₃H₇(i) | 4-bromo-1-methyl-3-pyrazolyl | white solid | 209–210 | 34.7 34.5 | 3.14 3.02 | 18.7 18.6 |
| 182 | H | CH₃ | H | H | 2,6-difluorophenyl | yellow powder | 229–233 (d) | 48.2 49.3 | 3.11 3.23 | 17.8 17.1 |
| 183 | H | H | H | CH₃ | 2,6-difluorophenyl | yellow powder | 221–223 (d) | 48.2 48.5 | 3.11 3.13 | 17.3 16.8 |
| 184 | Cl | H | CH₃ | H | 2-chloro-4-propoxy-3-pyridinyl | colorless solid | 205–216 (d) | 43.3 43.2 | 3.63 3.75 | 16.8 16.6 |
| 185 | OCH₃ | H | CH₃ | H | 2-chloro-4-(1-methyl-ethoxy-3-pyridinyl | tan solid | 243–245 (d) | 43.3 43.1 | 3.63 3.50 | 16.8 16.5 |
| 186 | OCH₃ | H | CH₃ | H | 2-chloro-4-propoxy-3-pyridinyl | colorless solid | 206–207 (d) | 46.7 47.0 | 4.41 4.46 | 17.0 17.2 |
| 187 | OCH₃ | H | CH₃ | H | 2-chloro-4-(1-methyl-ethoxy-3-pyridinyl | white solid | 236–237 (d) | 46.7 46.0 | 4.41 4.33 | 17.0 16.7 |
| 188 | OCH₃ | H | Cl | H | 4-bromo-1-methyl-5-pyrazolyl | tan powder | 119 (d) | 31.3 33.1 | 2.39 3.14 | 19.9 17.4 |

TABLE 1-continued

N-ARYL[1,2,4]TRIAZOLO[1,5-A]PYRIDINE-2-SULFONAMIDE COMPOUNDS

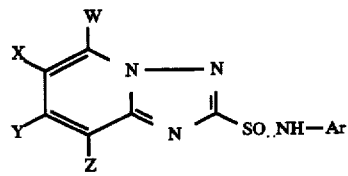

| Cpd. No. | W | X | Y | Z | Ar | Form | Melting point, °C. | % C calc. found | % H calc. found | % N calc. found |
|---|---|---|---|---|---|---|---|---|---|---|
| 189 | OC₃H₇(i) | H | CH₃ | H | 2,6-difluorophenyl | white powder | 235-237 | 50.3 50.4 | 4.22 4.03 | 14.7 14.8 |
| 190 | OCH₃ | H | Cl | H | 2-chloro-6-methoxycarbonylphenyl | white powder | 211-214 | 41.8 39.6 | 2.80 2.44 | 12.0 11.8 |
| 191 | OCH₃ | H | H | Cl | 2,6-difluorophenyl | lt. grey powder | >300 | 41.7 41.7 | 2.42 2.58 | 15.0 15.1 |
| 192 | OCH₃ | H | H | Br | 4-bromo-1-methyl-3-pyrazolyl | lt. tan powder | >300 | 31.3 31.8 | 2.39 2.44 | 19.9 19.8 |
| 193 | OCH₃ | H | H | Br | 2-fluoro-4-methyl-3-pyridinyl | lt. tan powder | >300 | 42.0 42.1 | 2.98 3.19 | 18.8 18.9 |
| 194 | OCH₃ | H | CH₃ | H | 4-chloro-1-methyl-3-pyrazolyl | tan solid | 235-237 | 40.4 40.2 | 3.67 3.75 | 23.6 23.7 |
| 195 | OCH₃ | H | CH₃ | H | 5-chloro-1-methyl-4-pyrazolyl | tan solid | 207-209 | 40.4 40.2 | 3.67 4.08 | 23.6 23.5 |
| 196 | OCH₂—CH₂F | H | CH₃ | H | 4-bromo-1-methyl-3-pyrazolyl | tan powder | 244-246 (d) | 36.0 36.7 | 3.26 3.15 | 19.4 18.9 |
| 197 | OCH₂—CH₂OCH₃ | H | Cl | H | 2,6-difluorophenyl | tan powder | 210-212 (d) | 43.0 43.1 | 3.13 3.27 | 13.4 13.1 |
| 198 | OCH₃ | H | Br | H | 2,6-difluorophenyl | lt. tan powder | 235-236 (d) | 37.2 37.2 | 2.16 2.18 | 13.4 13.4 |
| 199 | OCH₃ | H | Br | H | 2-fluoro-4-methyl-3-pyridinyl | lt. tan powder | 210-211 (d) | 37.5 37.7 | 2.66 2.54 | 16.8 16.6 |
| 200 | OCH₃ | H | Br | H | 4-bromo-1-methyl-3-pyrazolyl | lt. tan powder | 241-242 (d) | 28.3 28.7 | 2.16 2.25 | 18.0 18.3 |
| 201 | OCH₃ | H | H | Br | 2,6-difluorophenyl | off-white powder | >300 | 37.2 36.8 | 2.16 2.12 | 13.4 13.3 |
| 202 | OCH₃ | H | H | Br | 2-fluoro-4-methyl-3-pyridinyl | tan powder | >300 | 37.5 36.9 | 2.66 2.50 | 16.8 16.5 |
| 203 | OCH₃ | H | H | Br | 4-bromo-1-methyl-3-pyrazolyl | off-white powder | >300 | 28.3 28.5 | 2.16 2.13 | 18.0 17.9 |
| 204 | OCH₃ | H | CH₃ | H | 2,4,5-trichloro-3-pyridinyl | colorless solid | 235-236 (d) | 36.9 37.0 | 2.38 2.49 | 16.6 16.5 |
| 205 | OCH₂CH₃ | H | CH₃ | H | 2-chloro-4-ethoxy-3-pyridinyl | colorless solid | 200-201 | 46.7 46.7 | 4.41 4.18 | 17.0 16.9 |
| 206 | OCH₂CH₃ | H | CH₃ | H | 2-chloro-4-methoxy-3-pyridinyl | white solid | 239-240 (d) | 45.3 45.1 | 4.05 4.13 | 17.6 17.4 |
| 207 | Cl | H | CH₃ | H | 2-chloro-4-methoxycarbonyl-3-pyridinyl | white powder | 250-251 (d) | 38.6 40.0 | 2.74 2.66 | 17.3 16.3 |
| 208 | OC₃H₇(i) | H | CH₃ | H | 2-chloro-4-methoxy-3-pyridinyl | white powder | 244-245 (d) | 46.7 46.2 | 4.41 4.11 | 17.0 16.9 |
| 209 | OCH₂CF₃ | H | CH₃ | H | 2-chloro-4-methoxy-3-pyridinyl | white solid | 222-224 (d) | 39.9 39.6 | 2.90 2.53 | 15.5 15.1 |
| 210 | OCH₂CH₃ | H | CH₃ | H | 2-chloro-4-(1-methylethoxy)-3-pyridinyl | white solid | 217-218 (d) | 47.9 47.6 | 4.73 4.69 | 16.4 16.3 |
| 211 | OCH₂CH₃ | H | CH₃ | H | 4-ethoxycarbonyl-3-pyridinyl | white powder | 191-192 (d) | 50.4 50.8 | 4.46 4.72 | 17.4 17.3 |
| 212 | OCH₃ | H | CH₃ | H | 2-chloro-4-methoxycarbonyl-3-pyridinyl | white powder | 230-231 (d) | 43.8 44.0 | 3.43 3.46 | 17.0 16.8 |
| 213 | OCH₂CH₃ | H | Cl | H | 2-chloro-4-methyl-3-pyridinyl | lt. brown powder | 229-230 (d) | | | |
| 214 | OCH₃ | H | Cl | H | 2-chloro-4-ethoxy-3-pyridinyl | lt. brown powder | 161-162 (d) | | | |
| 215 | OCH₂CH₃ | H | Cl | H | 2-chloro-4-ethoxy-3-pyridinyl | lt. brown powder | 203-204 (d) | | | |
| 216 | OCH₂CH₃ | H | Cl | H | 2-chloro-4-methoxy-3-pyridinyl | lt. brown powder | 224-225 (d) | 40.2 40.6 | 3.13 3.26 | 16.4 6.6 |
| 217 | OCH₃ | H | CH₃ | H | 2-methoxy-4-methyl-3-pyridinyl | white powder | 235-237 (d) | 49.6 49.5 | 4.72 4.57 | 19.3 19.0 |
| 218 | OC₃H₇(i) | H | Cl | H | 2-chloro-4-methyl-3-pyridinyl | tan solid | 226-227 (d) | 43.3 43.1 | 3.63 3.70 | 16.8 16.2 |
| 219 | OC₃H₇(i) | H | Cl | H | 2-chloro-4-methoxy-3-pyridinyl | off-white solid | 154-1255 | 41.7 41.4 | 3.50 3.26 | 16.2 15.7 |
| 220 | H | CF₃ | H | OCH₃ | 2-chloro-4-methyl-3- | off-white | 225-227 | 38.4 | 2.53 | 16.0 |

TABLE 1-continued

N-ARYL[1,2,4]TRIAZOLO[1,5-A]PYRIDINE-2-SULFONAMIDE COMPOUNDS

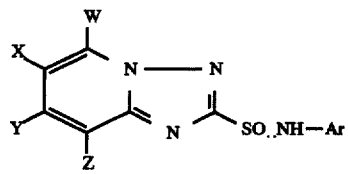

| Cpd. No. | W | X | Y | Z | Ar | Form | Melting point, °C. | % C calc. found | % H calc. found | % N calc. found |
|---|---|---|---|---|---|---|---|---|---|---|
| 221 | H | CF₃ | H | OCH₂CH₃ | 2-chloro-4-methoxy-3-pyridinyl | solid off-white solid | 162-163 | 38.6 39.9 37.5 | 2.20 2.90 3.22 | 16.1 15.5 14.7 |
| 222 | Cl | H | CH₃ | H | 2-methoxy-4-methyl-3-pyridinyl | off-white solid | 221-222 | 45.7 45.3 | 3.84 3.95 | 19.0 19.2 |
| 223 | OCH₃ | H | H | Cl | 2-chloro-4-methoxy-3-pyridinyl | off-white solid | >300 (d) | 38.6 38.4 | 2.74 2.75 | 17.3 17.1 |
| 224 | OC₃H₇(n) | H | H | Cl | 2-chloro-4-methoxy-3-pyridinyl | off-white powder | 168-170 (d) | 41.7 41.8 | 3.50 3.55 | 16.2 16.0 |
| 225 | OC₂H₅ | H | H | Cl | 2-chloro-4-methoxy-3-pyridinyl | off-white powder | 231-233 (d) | 41.7 40.3 | 3.50 3.31 | 16.2 16.3 |
| 226 | OCH₃ | H | CH₃ | H | 2-fluoro-4-methoxy-3-pyridinyl | white solid | 257-258 (d) | 45.8 45.8 | 3.84 3.87 | 19.1 19.0 |
| 227 | OC₂H₅ | H | CH₃ | H | 2-fluoro-4-methoxy-3-pyridinyl | white solid | 240-241 (d) | 47.2 46.7 | 4.23 4.55 | 18.4 18.1 |
| 228 | OCH₃ | H | H | Br | 2-chloro-4-methoxy-3-pyridinyl | tan solid | 220-222 (d) | 34.8 34.9 | 2.47 2.47 | 15.6 15.5 |
| 229 | OCH₃ | H | H | Br | 4-methoxycarbonyl-3-pyridinyl | tan powder | 154-156 (d) | 38.0 38.2 | 2.73 2.79 | 15.8 15.6 |
| 230 | OCH₃ | H | CH₃ | H | 2-chloro-4-(2,2,2-trifluoroethoxy)-3-pyridinyl | white solid | 213-214 | 39.9 38.9 | 2.90 3.12 | 15.5 15.2 |
| 213 | OC₂H₅ | H | CH₃ | H | 2-chloro-4-(2,2,2-trifluoroethoxy)-3-pyridinyl | white solid | 211-212 | 41.3 41.1 | 3.25 3.30 | 15.0 15.0 |
| 232 | OCH₃ | H | CH₃ | H | 2-bromo-4-methoxy-3-pyridinyl | white solid | 214-215 (d) | 39.3 39.0 | 3.30 3.46 | 16.4 16.0 |
| 233 | OC₂H₅ | H | CH₃ | H | 2-bromo-4-methoxy-3-pyridinyl | off-white solid | 245-246 (d) | 40.7 40.9 | 3.65 3.85 | 15.8 15.9 |
| 234 | H | CH₃ | H | OCH₃ | 2-chloro-4-methoxy-3-pyridinyl | tan powder | 198-200 | 43.8 43.0 | 3.68 3.76 | 18.3 17.9 |
| 235 | OCH₃ | H | CH₃ | H | 2-fluoro-4-ethoxy-3-pyridinyl | white solid | 253-255 | 47.2 47.3 | 4.23 4.00 | 18.4 18.5 |
| 236 | OC₂H₅ | H | CH₃ | H | 2-fluoro-4-ethoxy-3-pyridinyl | tan solid | 206-208 | 48.6 48.7 | 4.59 4.72 | 17.7 17.9 |
| 237 | Cl | H | CH₃ | H | 2-fluoro-4-ethoxy-3-pyridinyl | white solid | 218-219 | 43.6 43.6 | 3.40 3.38 | 18.2 18.4 |
| 238 | OC₂H₅ | H | CH₃ | H | 2-chloro-4-(n)propoxy 3-pyridinyl | white solid | 130-132 | 47.9 47.6 | 4.73 4.67 | 16.4 16.4 |
| 239 | OCH₃ | H | CH₃ | H | 2-chloro-4-(2-fluoro-ethoxy)-3-pyridinyl | off-white solid | 218-220 (d) | 43.3 43.1 | 3.64 3.60 | 16.8 16.7 |
| 240 | OC₂H₅ | H | CH₃ | H | 2-chloro-4-(2-fluoro-ethoxy)-3-pyridinyl | white solid | 210-212 (d) | 44.7 44.5 | 3.99 4.19 | 16.3 16.6 |
| 241 | OC₂H₅ | H | H | Cl | 2,6-difluorophenyl | white powder hydrate | >300 (d) | 41.3 41.3 | 3.22 2.65 | 13.8 13.6 |
| 242 | OCH₃ | H | H | Br | 2-chloro-6-methoxy-carbonylphenyl | tan powder | 202-204 (d) | 37.9 37.8 | 2.54 2.56 | 11.8 11.6 |
| 243 | OCH₃ | H | CH₃ | H | 4-bromo-1-methyl-3-pyrazolyl | white powder | 234-236 | 35.9 35.1 | 3.27 3.24 | 21.0 21.4 |
| 244 | OCH₃ | H | CH₃ | H | 1-methyl-4-(tri-fluoromethyl)-3-pyrazolyl | tan solid | 240-236 | 35.9 40.2 | 3.27 3.14 | 21.0 21.4 |
| 245 | Cl | H | CH₃ | H | 1-methyl-3-(tri-fluoromethyl)-5-methoxy-4-pyrazolyl | tan solid | 211-212 | 36.8 36.8 | 2.85 2.74 | 19.8 19.8 |
| 246 | OCH₃ | H | CH₃ | H | 1-methyl-3-(tri-fluoromethyl)-5-methoxy-4-pyrazolyl | off-white solid | 186-188 | 40.0 38.8 | 3.60 3.52 | 20.0 19.4 |
| 247 | OC₂H₅ | H | CH₃ | H | 1-methyl-3-(tri-fluoromethyl)-5-methoxy-4-pyrazolyl | brown solid | 205-207 | 41.5 40.5 | 3.94 3.52 | 19.4 19.1 |
| 248 | OCH₃ | H | CH₃ | H | 1,3-dimethyl-5-(tri- | off-white | 247-249 | 41.6 | 3.74 | 20.8 |

TABLE 1-continued

N-ARYL[1,2,4]TRIAZOLO[1,5-A]PYRIDINE-2-SULFONAMIDE COMPOUNDS

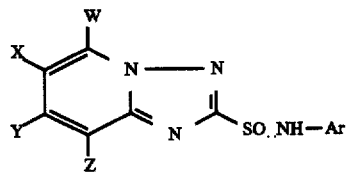

| Cpd. No. | W | X | Y | Z | Ar | Form | Melting point, °C. | % C calc. found | % H calc. found | % N calc. found |
|---|---|---|---|---|---|---|---|---|---|---|
| | | | | | fluoromethyl)-4-pyrazolyl | solid | | 41.1 | 4.07 | 20.6 |
| 249 | OCH₂H₅ | H | CH₃ | H | 1,3-dimethyl-5-(trifluoromethyl)-4-pyrazolyl | tan solid | 251–252 | 43.1 43.4 | 4.10 4.16 | 20.1 20.3 |
| 250 | OCH₃ | H | CH₃ | H | 1-methyl-3-(trifluoromethyl)-5-chloro-4-pyrazolyl | off-white solid | 226–228 | 36.8 36.9 | 2.85 3.04 | 19.8 19.5 |
| 251 | OC₂H₅ | H | CH₃ | H | 1-methyl-3-(trifluoromethyl)-5-chloro-4-pyrazolyl | white solid | 239–240 | 38.3 38.6 | 3.22 3.46 | 19.2 19.2 |
| 252 | Cl | H | H | OCH₃ | 2,6-difluorophenyl | off-white powder | 190–191 (d) | 41.7 41.3 | 2.42 2.37 | 15.0 15.0 |
| 253 | Cl | H | H | OCH₃ | 2-chloro-4-methoxy-3-pyridinyl | white powder | 253–253 (d) | 38.6 38.8 | 2.74 2.90 | 17.3 17.4 |
| 254 | Cl | H | H | OCH₃ | 1-methyl-4-bromo-3-pyrazoyl | lt. tan powder | 269–270 (d) | 31.3 31.9 | 2.39 2.39 | 19.9 19.6 |
| 255 | OCH₃ | H | H | OCH₃ | 2,6-difluorophenyl | off-white powder | 319–320 (d) | 45.1 43.4 | 3.27 3.13 | 15.1 14.8 |
| 256 | OCH₃ | H | H | OCH₃ | 2-chloro-4-methoxy-3-pyridinyl | lt. tan powder | 256–258 (d) | 42.1 41.7 | 3.53 2.85 | 17.7 17.3 |
| 257 | OCH₃ | H | H | OCH₃ | 1-methyl-4-bromo-3-pyrazoyl | tan powder | 257–258 (d) | 34.5 34.1 | 3.14 2.98 | 20.1 19.8 |
| 258 | OCH₂H₅ | H | CH₃ | H | 1,5-dimethyl-3-(ethoxycarbonyl)-4-pyrazolyl | | | | | |
| 259 | OCH₃ | H | F | H | 4-bromo-1-methyl-3-pyrazolyl | | | | | |
| 260 | OCH₃ | H | CF₃ | H | 2,6-difluorophenyl | | | | | |
| 261 | H | F | H | OCH₃ | 2,6-difluorophenyl | | | | | |
| 262 | OCH₃ | H | H | F | 2,6-difluorophenyl | | | | | |
| 263 | OCH₃ | H | H | I | 4-bromo-1-methyl-3-pyrazolyl | | | | | |

The compounds of Formula I wherein V represents hydrogen can generally be prepared by combining a 2-chlorosulfonyl[1,2,4]triazolo[1,5-a]pyridine compound of Formula II:

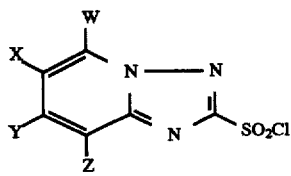

with an appropriately substituted aromatic primary amine compound of Formula III:

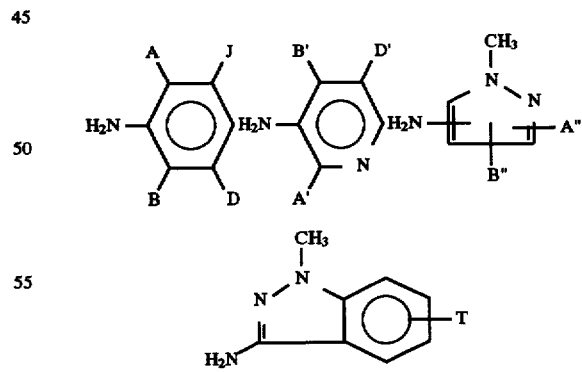

in the presence of pyridine or a methylpyridine compound, and, optionally but preferably, a catalytic amount of dimethyl sulfoxide. The substituents W, X, Y, and Z of Formula II and the substituents A, B, J, D, A', B', D', A", B", and T are as defined hereinbefore for the compounds of Formula I. Compounds of Formula II wherein one or both of W and Z represents Cl or OCH₃ or wherein W represents OCH₂CH₃ or OC₃H₇(i) are often preferred as are compounds of Formula II wherein two of W, X, Y, and Z represent hydrogen.

The preparation is usually accomplished by placing a 2-chlorosulfonyl[1,2,4]triazolo[1,5-a]pyridine compound of Formula II, an aromatic amine compound of Formula III, and an inert solvent, such as acetonitrile, N,N-dimethylformamide, N-methyl-2-pyrrolidinone, tetrahydrofuran, and the like, in a vessel and then adding the pyridine or methylpyridine, preferably pyridine, and a catalytic amount of dimethyl sulfoxide. The mixture is allowed to react, typically at ambient temperature, but heating if necessary. After a substantial quantity of the compound of Formula I has formed or a substantial quantity of the chlorosulfonyl compound of Formula II has been consumed, the desired product is recovered, typically by removing the solvent by evaporation, adding water, and removing the liquids from the solid that forms by centrifugation or filtration. The recovered product can be purified, if desired, by extracting with an immiscible organic solvent, such as methylene chloride, and with water. Alternatively, the desired compounds of Formula I can be purified by recrystallization and by other commonly used methods.

Approximately equimolar quantities of the compounds of Formulas II and III are generally used in the preparation of compounds of Formula I although a substantial excess of one or the other may be employed. The pyridine compound is generally employed in an amount of from at least 1 to about 5 moles per mole of compound of Formula II. Dimethyl sulfoxide is typically used in less than an equimolar amount; amounts over about 0.3 mole per mole of compound of Formula II are usually deleterious. Acetonitrile is often the preferred solvent.

It is sometimes advantageous to prepare the compounds of Formula I by condensing a compound of Formula II with an N-trialkylsilyl derivative of a substituted aromatic amine compound of Formula III. The method employed is analogous to that described in U.S. Pat. No. 4,910,706 for N-trialkylsilylanilines. The reaction conditions required are essentially the same as those described hereinabove for the condensation of a chlorosulfonyl compound of Formula II with a substituted aromatic amine of Formula III with the exception that the pyridine compound base may be omitted. The substituted N-trialkylsilyl derivatives of aromatic amines employed can be prepared from the corresponding substituted aromatic amine compounds by treatment with a trialkylsilyl halide and a trialkylamine essentially as described in U.S. Pat. No. 4,910,206 for aniline compounds. Sodium iodide is typically employed as a catalyst when the halide is chloride. The N-trialkylsilyl compounds are typically prepared and used immediately and without purification.

Compounds of Formula I wherein V represents hydrogen and W, Y, or Z represents OCH₂CF₃, S(C₁-C₃)alkyl, or O(C₁-C₃)alkyl optionally monosubstituted with F, Cl, or OCH₃ can be made from the corresponding compounds of Formula I wherein W, Y, or Z represents F, Cl, or Br by treatment with an appropriate nucleophilic reagent, such as sodium methoxide or sodium methanethiolate in methanol, acetonitrile, or dimethyl sulfoxide. Similarly, such compounds wherein W, Y, or Z represents F or Br can sometimes be made from corresponding compounds wherein W, Y, or Z represents Cl by treatment with an alkali metal halide, such as potassium fluoride. Typically, chloro compounds are the most readily available and are employed. The reaction conditions employed are similar to those used for the related exchange reactions of 2- and 4-halopyrimidines and pyridines. Non-aqueous media are preferred. The amount of heat and the time required are dependent on the position of the halogen, the identity of the halogen, the other substituents present, and the medium employed. The selective replacement of a halogen in the W position can readily be achieved as this halogen is much more reactive than are halogens in the X, Y, and Z positions. Halogens in the Z position are more reactive than those in the X position.

Many compounds of Formula I wherein one or more of X and Z represents F, Cl, Br, or H can be also be prepared by first preparing a compound of Formula I wherein one or both of X and Z represents nitro, reducing the nitro group to an amino group using standard reaction procedures for the reduction of a nitro group to an amino group well-known to those in the art, and then converting the amino group to a F, Cl, Br, I, OH, or H group by diazotization under appropriate reaction conditions generally known in the art.

Compounds of Formula I wherein V represents COR', CO₂R", or CONR'''₂ wherein R', R", and R''' are as defined hereinabove can be prepared from compounds of Formula I wherein V represents hydrogen by acylation with a compound of the formula ClCOR', ClCO₂R", or ClCONR'''₂ using conventional procedures known in the art for the acylation of sulfonamides.

The 2-chlorosulfonyl[1,2,4]triazolo[1,5-a]pyridine compounds of Formula II can be prepared by chloroxidation of 2-benzylthio[1,2,4]triazolo[1,5-a]pyridine compounds of Formula IV:

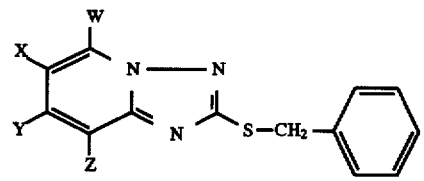

wherein W, X, Y, and Z are as defined hereinabove. Such compounds wherein one or both of W and Z represents Cl or OCH₃ or wherein W represents OCH₂CH₃ or OC₃H₇(i) are often preferred as are compounds wherein two of W, X, Y, and Z represent hydrogen. The chloroxidation reaction can be carried out under the reaction conditions usually employed for such reactions. In a typical operation, the compound of Formula IV is dissolved or suspended in a water-immiscible organic solvent, such as chloroform or dichloromethane, water is added, and chlorine is added with good agitation to the mixture at temperatures below about 20° C. when the reaction is complete, the organic solvent phase is separated and wasted with water and the solvent is typically removed by evaporation to obtain the desired chlorosulfonyl compound as a crude product. This crude product can be purified by standard methods, such as by recrystallization, extraction, or chromatography.

Compounds of Formula IV wherein W, Y, or Z represents I, F, OCH₂CF₃, S(C₁-C₃)alkyl, or O(C₁-C₃)alkyl optionally monosubstituted with F, Cl, or OCH₃ can be made from the corresponding compounds of Formula IV wherein W, Y, or Z represents F, Cl, or Br by treatment with an appropriate nucleophilic reagent, such as sodium methoxide or sodium methanethiolate in methanol or potassium ethoxide in ethanol, acetonitrile, or dimethyl sulfoxide. The reaction conditions are similar to those employed to make the corresponding conversion of compounds of Formula I wherein W, Y, or Z represents F, Cl, or Br to analogs wherein W, Y, or Z represents $OCH_2CF_3$, $S(C_1-C_3)$alkyl or $O(C_1-C_3)$alkyl optionally monosubstituted with F, Cl, or $OCH_3$. Heat is applied, if necessary, to accelerate the reaction. Compounds of Formula IV wherein W represents F, $OCH_2CF_3$, $S(C_1-C_3)$ alkyl or $O(C_1-C_3)$alkyl optionally mono-substituted with F, Cl, or $OCH_3$ and one or more of X, Y, and Z represents Cl or Br can be made in this way from compounds wherein W and one or more of X, Y, and Z represents chloro or bromo by the selective reaction of the chloro or bromo substituent in the 5-position (W) because it is considerably more easily displaced. Similarly, compounds of Formula IV wherein Z represents F, $OCH_2CF_3$, $S(C_1-C_3)$alkyl or $O(C_1-C_3)$alkyl optionally mono-substituted with F, Cl, or $OCH_3$ and X represents chloro or bromo can be made from compounds wherein both X and Z represent chloro or bromo by selective reaction.

Compounds of Formula IV wherein W represents Cl can be prepared in three steps from a substituted glutaconic anhydride. The anhydride is first treated with the reaction product of thiosemicarbazide and benzyl chloride in the presence of a tertiary amine, such as triethylamine, and in a solvent, such as 2-propanol. The reaction can be carried out by heating the reaction mixture described for a period, adding an alkali metal alkoxide, such as sodium methoxide and heating for another period, and then acidifying the reaction mixture and recovering the insoluble solid product that forms. This solid product can then converted to a compound of Formula IV wherein W represents OH by carefully heating until the evolution of carbon dioxide ceases. This compound of Formula I wherein W represents OH can then be converted to the corresponding compound wherein W represents Cl by combining it with an excess of phosphorus oxychloride and a tertiary amine, such as N,N-dimethylaniline, and heating. The product can then be recovered by removing the excess phosphorus oxychloride by evaporation under reduced pressure.

Compounds of Formula IV wherein one or both of X and Z represents F, Cl, Br, I, OH, or H can also be prepared by first preparing a compound of Formula IV wherein one or both of X and Z represents nitro, reducing the nitro group to an amino group using standard reaction procedures for the reduction of a nitro group to an amino group well-known to those in the art, and then converting the amino group to a F, Cl, Br, I, OH, or H group by diazotization under appropriate reaction conditions. Compounds wherein one of X and Z represents OR can be prepared from the corresponding compound wherein one of X and Z represents CH by consecutive treatment with phosphorus oxychloride and an alkali metal salt of the alcohol ROH. Compounds wherein W and/or Y represents chloro or bromo can be obtained by halogenation of the amino compounds before diazotization. Appropriate reaction conditions for such reactions are generally known in the art.

It has been found, however, that the reduction of a compound of Formula IV wherein W and X represent hydrogen, Y represents hydrogen, methyl, or a halogen, and Z represents nitro (2-benzylthio-8-nitro[1,2,4]triazolo[1,5-a]pyridine and certain 7-substituted analogs) with stannous chloride in the presence of stannic chloride and a reactive medium comprising hydrogen chloride or a $C_1$–$C_3$ alcohol produces not only the corresponding compound of Formula IV wherein Z represents amino, but also the corresponding compound of Formula IV wherein W represents chloro or alkoxy and Z represents amino. The latter can be made to be the dominate product. The amino compounds obtained can be converted into compounds of Formula IV wherein W represents chloro or alkoxy and Z represents hydrogen or a halogen by standard means.

When the reactive medium contains hydrogen chloride as an essential ingredient, an 8-amino-2-benzylthio-5-chloro[1,2,4]triazolo[1,5-a]pyridine compound is obtained along with a small amount of an 8-amino-2-benzylthio[1,2,4]triazolo[1,5-a]pyridine compound. The reactive medium generally includes a solvent, which can be water, N-methyl-2-pyrrolidinone, N,N-dimethylformamide, dimethyl sulfoxide, tetrahydrofuran, or other suitable solvent. Concentrated aqueous hydrochloric acid is the generally preferred reactive medium in this embodiment. When the reactive medium contains an alcohol as an essential ingredient, a 5-alkoxy-8-amino-2-benzylthio[1,2,4]triazolo[1,5-a]pyridine compound is obtained. Methanol, ethanol, and propanol are examples of suitable alcohols. The reaction is generally carried out by combining one molar equivalent of a 2-benzylthio-8-nitro[1,2,4]triazolo[1,5-a]pyridine compound with at least about 3 molar equivalents of stannous chloride, one molar equivalent of stannic chloride, and an excess of hydrogen chloride or at least one molar equivalent of the alcohol. The alcohols are typically employed in a large excess. The reaction mixture is heated at about 50° to about 120° C. with good agitation to effect the simultaneous reduction and substitution. The products can be recovered by standard means, including by dissolving the hydrochloride that is formed initially in water, basifying with an alkali metal hydroxide, and recovering the product by filtration or by solvent extraction.

Compounds of Formula IV wherein one or both of X and Z represents nitro can be prepared from (3 or 5)-nitro-2-hydrazinopyridine compounds by consecutive reactions with carbon disulfide, hydrogen peroxide, and benzyl chloride and triethylamine. The reactions take place at ambient temperatures and are exothermic. A reaction period of up to several days is sometimes required to assure that all of the product is in the desired, rearranged state, but rearrangement takes place spontaneously under the reaction conditions. The method is similar to that disclosed in the art for the preparation of 2-benzylthio[1,2,4]triazolo[1,5-c]pyrimidine compounds.

Many compounds of Formula IV can be prepared by the reaction 1-((1-imidazolylthionyl)amino)-2-iminopyridine compounds of Formula V:

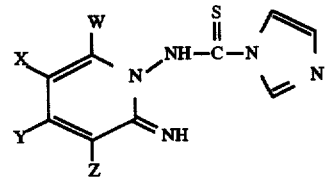

with benzyl chloride in a solvent, such as butanol, by heating. The desired compounds of Formula V can be recovered by conventional means.

Compounds of Formula V can be prepared by combining O-mesitylenesulfonylacetohydroxamate and perchloric acid in dioxane at temperatures below ambient, adding the solution obtained to 2-aminopyridine compounds of Formula VI:

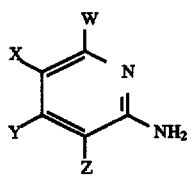

at temperatures below ambient, and then adding 1,1'-thiocarbonyldiimidazole to the mixture. The desired compounds of Formula VI can be recovered by conventional means.

It has additionally been found that compounds of Formula IV can be prepared from the corresponding 2-amino[1,2,4]triazolo[1,5-a]pyridine of Formula VII:

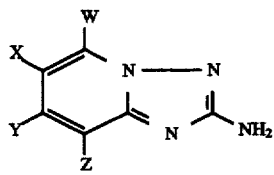

wherein W, X, Y, and Z are as defined for compounds of Formula I. Compounds of Formula VII wherein one or both of W and Z represents Cl or $OCH_3$ or wherein W represents $OCH_2CH_3$ or $OC_3H_7(i)$ are often preferred as are compounds of Formula II wherein two of W, X, Y, and Z represent hydrogen. The method is closely related to the chemistry disclosed in *J. Chemical Society Chemical Communications*, 1980 756–757. It is especially useful for the preparation of compounds of Formula I wherein W represents chloro, methoxy, ethoxy, or isopropoxy, X and Z each represent hydrogen, and Y represents methyl or a halogen; or wherein W represents chloro, methoxy or ethoxy, X and Y each represent hydrogen, and Z represents methyl, methoxy, or a halogen; or wherein Z represents chloro, methoxy or ethoxy, W and Y each represent hydrogen, and X represents methyl, trifluoromethyl, or a halogen. The preparation is preferably carried out by adding an excess of t-butyl nitrite to a solution consisting of a compound of Formula VII and dibenzyl disulfide in a compatible organic solvent, such as acetonitrile, and heating the combination to reflux until the evolution of gas subsides. The reaction is exothermic. The desired compounds of Formula IV can be recovered by conventional means, such as by removing the volatile components of the product mixture by evaporation, and can be purified by conventional means, such as by column chromatography or recrystallization.

Compounds of Formula VII can be prepared by treatment of appropriately substituted N-(2-pyridinyl)-N-carboethoxythiourea compounds with hydroxylamine in a solvent such as ethanol and heating for a few hours. The hydroxylamine is typically generated by neutralization of the hydrochloride with a hindered tertiary amine, such as diisopropylethylamine, or an alkoxide, such as sodium ethoxide. The desired compounds of Formula VII can be recovered by conventional means, such as by removal of the volatile components of the reaction mixture by evaporation, and can be purified by conventional means, such as by extraction with water and/or other solvents in which they are sparingly soluble. N-(2-Pyridinyl)-N-carboethoxythiourea compounds can be obtained by treatment of appropriately substituted 2-aminopyridine compounds with ethoxycarbonyl isothiocyanate. Compounds of Formula VII tan also be prepared from 2-cyanoaminopyridine compounds by the methods disclosed in *Monatshefte fur Chemie*, 114, 789–798 (1983).

The substituted anilines and 3-, 4-, and 5-aminopyrazoles that are required as intermediates for the compounds of Formula I are known in the art or can be prepared by general methods known in the art. The substituted 3-aminopyridines and 3-aminoindazoles that are required as intermediates can be prepared by the methods presented herein, are known in the art, or can be prepared by general methods known in the art.

4-Alkoxy-3-amino-2-chloropyridine compounds can be prepared by chlorination of known 4-alkoxy-3-aminopyridine compounds. 4-Alkoxy-3-amino-2-fluoropyridine compounds can be prepared from 4-alkoxy-2-fluoropyridine compounds by lithiation with butyl lithium and treatment of the intermediate with diphenyl phosphoryl azide. 4-Alkoxy-2-fluoropyridine compounds can be prepared by reduction of 4-Alkoxy-3,5-dichloro-2-fluoropyridine compounds with hydrogen. Many 4-substituted 2-alkoxy-3-aminopyridine compounds can be prepared from 2-alkoxy-3-aminopyridine compounds by lithiation of the corresponding t-butoxycarbonyl derivative and reaction of this with an electrophilic reagent in processes closely related to those disclosed in *J. Organic Chemistry*, 60, 1875–1877 (1995). Thus, 2-alkoxy-3-amino-4-fluoropyridine compounds can be prepared from t-butyl N-(2-alkoxy-3-pyridinyl)carbamates by fluorination with N-fluorodibenzenesulfonimide of the intermediate obtained on lithiation with t-butyl lithium followed by treatment with anhydrous p-toluenesulfonic acid to remove the protecting t-butoxycarbonyl group. Similarly, 2-alkoxy-3-amino-4-chloropyridine compounds can be obtained by chlorination of t-butyl N-(2-alkoxy-3-pyridinyl)carbamates with hexachloroethane in an analogous process. Alkyl 3-amino-2-alkoxyisonicotinate compounds can be prepared analogously from t-butyl N-(2-alkoxy-3-pyridinyl)carbamate compounds by lithiating with butyl lithium, treating the intermediate formed with carbon dioxide and then an alkyl iodide, and finally removing the protecting t-butoxycarbonyl group by treatment with anhydrous t2-toluenesulfonic acid. The amine-protected t-butyl N-(2-alkoxy-3-pyridinyl) carbamate compounds can be prepared from 2-alkoxy-3-aminopyridine compounds by treatment with di-t-butyl dicarbonate. 3-Amino-2-chloroisonicotinic acid esters can be prepared by chlorination of 3-aminoisonicotinic acid esters using 1,3-dichloro-5,5-dimethylhydantion as the chlorinating agent. 3-Amino-2-fluoro-4-methylpyridine can be prepared by palladium on carbon catalyzed reduction of 2-fluoro-4-methyl-3-nitropyridine with hydrogen. This compound can be converted to other 4-alkyl-3-amino-2-fluoropyridine compounds by alkylation of the methyl group. These and other 3-aminopyridine compounds of Formula III can be made using a variety of preparative methods well-established in the art.

While in is possible to utilize the 1,2,4-triazolo[1,5-a]pyridine-2-sulfonamide compounds of Formula I directly as herbicides, it is preferable to use them in mixtures containing an herbicidally effective amount of the compound along with at least one agriculturally acceptable adjuvant or carrier. Suitable adjuvants or carriers should not be phytotoxic to valuable crops, particularly at the concentrations employed in applying the compositions for selective weed control in the presence of crops, and should not react chemically with the compounds of Formula I or other composition ingredients. Such mixtures can be designed for application directly to weeds or their locus or can be concentrates or formulations which are normally diluted with additional carriers and adjuvants before application. They can be solids, such as, for example, dusts, granules, water dispersible granules, or wettable powders, or liquids, such as, for example, emulsifiable concentrates, solutions, emulsions or suspensions.

Suitable agricultural adjuvants and carriers that are useful in preparing the herbicidal mixtures of the invention are well known to those skilled in the art.

Liquid carriers that can be employed include water, toluene, xylene, petroleum naphtha, crop oil, acetone, methyl ethyl ketone, cyclohexanone, trichloroethylene, perchloroethylene, ethyl acetate, amyl acetate, butyl acetate, propylene glycol monomethyl ether and diethylene glycol monomethyl ether, methanol, ethanol. isopropanol, amyl alcohol, ethylene glycol, propylene glycol, glycerine, and the like. Water is generally the carrier of choice for the dilution of concentrates.

Suitable solid carriers include talc, pyrophyllite clay, silica, attapulgus clay, kieseiguhr, chalk, diatomaceous earth, lime, calcium carbonate, bentonite clay, Fuller's earth, cotton seed hulls, wheat flour, soybean flour, pumice, wood flour, walnut shell flour, lignin, and the like.

It is frequently desirable to incorporate one or more surface-active agents into the compositions of the present invention. Such surface-active agents are advantageously employed in both solid and liquid compositions, especially those designed to be diluted with carrier before application. The surface-active agents can be anionic, cationic or non-ionic in character and can be employed as emulsifying agents, wetting agents, suspending agents, or for other purposes. Typical surface active agents include salts of alkyl sulfates, such as diethanol-ammonium lauryl sulfate; alkylarylsulfonate salts, such as calcium dodecylbenzenesulfonate; alkylphenol-alkydene oxide addition products, such as nonylphenol-$C_{18}$ ethoxylate; alcohol-alkylene oxide addition products, such as tridecyl alcohol-$C_{16}$ ethoxylate; soaps, such as sodium stearate; alkylnaphthalenesulfonate salts, such as sodium dibutylnaphthalenesulfonate; dialkyl esters of sulfosuccinate salts, such as sodium di(2-ethylhexyl)sulfosuccinate; sorbitol esters, such as sorbitol oleate; quaternary amines, such as lauryl trimethylammonium chloride; polyethylene glycol esters of fatty acids, such as polyethylene glycol stearate; block copolymers of ethylene oxide and propylene oxide; and salts of mono and dialkyl phosphate esters.

Other adjuvants commonly utilized in agricultural compositions include antifoam agents, compatibilizing agents, sequestering agents, neutralizing agents and buffers, corrosion inhibitors, dyes, odorants, penetration aids, spreading agents, sticking agents, dispersing agents, thickening agents, freeze point depressants, antimicrobial agents, and the like. The compositions can also contain other compatible components, for example, other herbicides, plant growth regulants, fungicides, insecticides, and the like and can be formulated with liquid fertilizers or solid, particulate fertilizer carriers such as ammonium nitrate, urea and the like.

The concentration of the active ingredients in the herbicidal compositions of this invention is generally from about 0.001 to about 98 percent by weight. Concentrations from about 0.01 to about 90 percent by weight are often employed. In compositions designed to be employed as concentrates, the active ingredient is generally present in a concentration from about 5 to about 98 weight percent, preferably about 10 to about 90 weight percent. Such compositions are typically diluted with an inert carrier, such as water, before application. The diluted compositions usually applied to weeds or the locus of weeds generally contain about 0.001 to about 5 weight percent active ingredient and preferably contain about 0.01 to about 0.5 percent.

The present compositions can be applied to weeds or their locus by the use of conventional ground or aerial dusters, sprayers, and granule applicators, by addition to irrigation water, and by other conventional means known to those skilled in the art.

The compounds of Formula I have been found to be useful preemergence and postemergence herbicides. They can be employed at non-selective (higher) rates of application to control essentially all of the vegetation in an area and, often, at selective (lower) rates of application for the selective control of undesirable vegetation in grass crops, such as corn, wheat, barley, and rice as well as in broadleaf crops, such as soybeans and cotton. While each of the compounds encompassed by Formula I is within the scope of the invention, the degree of herbicidal activity, the selectivity, and the spectrum of weed control obtained varies depending upon the substituents present. The selection of a specific compound of the invention for a specific application can be done readily without invention from the data and information presented herein along with standard testing.

The term herbicide is used herein to mean an active ingredient which controls or adversely modifies the growth of plants. An herbicidally effective or vegetation controlling amount is an amount of active ingredient which causes an adversely modifying effect and includes deviations from natural development, killing, regulation, dessication, retardation, and the like. The terms plants and vegetation are meant to include germinant seeds, emerging seedlings and established vegetation.

Herbicidal activity is exhibited by the compounds of the present invention when they are applied directly to the plant or to the locus of the plant at any stage of growth or before emergence. The effect observed depends upon the plant species to be controlled, the stage of growth of the plant, the application parameters of dilution and spray drop size, the particle size of solid components, the environmental conditions at the time of use, the specific compound employed, the specific adjuvants and carriers employed, the soil type, and the like, as well as the amount of chemical applied. These and other factors can be adjusted as is known in the art to promote selective herbicidal action. Generally, it is preferred to apply the compounds of Formula I postemergence to relatively immature plants to achieve the maximum control of broadleaf weeds.

Application rates of about 0.001 to about 1 Hg/Ha are generally employed in postemergence operations; for preemergence applications, rates of about 0.01 to about 10 Kg/Ha are generally employed.

EXAMPLES

The following Examples are presented to illustrate the various aspects of this invention and should not be construed as limitations to the claims.

1. Preparation of 1-((1-Imidazolylthionyl)amino)-2-aminopyridine

A solution of ethyl O-mesitylenesulfonylacetohydroxamate (39.5 g (grams), 0.138 mol (mole)) in dioxane (225 mL (milliliters)), which was prepared according to Tetrahedron Letters 40, 4133–4135 (1972), was cooled to about 8° C. Perchloric acid (17.4 mL of 70 percent, 0.203 mol) was added dropwise with stirring over 5 min (minutes). The reaction was then allowed to warm to room temperature over 1.5 hours. It was then diluted with ice water and the solids that formed were recovered by filtration and washed with water. The damp solids obtained were mixed with chloroform (300 mL) and the organic layer that formed was added dropwise with stirring and cooling to a solution of 2-aminopyridine (12.4 g, 0.131 mol) in chloroform (300 mL) at 5° C. The temperature rose to 10° C. during the addition. The reaction was allowed to warm to room temperature and then 1,1'-thiocarbonyldiimidazole (30.0 g, 0.168 mol) was added and the mixture was warmed to 40° C. for several hours. The mixture was then cooled in an ice bath and the solid that slowly separated was recovered by filtration to obtain the 10.4 g (36 percent of theory) of title compound as a white powder melting at 174°–175° C. (d).

$^1$H NMR Nuclear Magnetic Resonance Spectroscopy (200 megahertz)) (DMSO-$d_6$(dimethyl sulfoxide)): 8.48 (s, 1H), 7.90 (s, 1H), 7.87 (d, 1H, J=4.0), 7.73 (t, 1H, J=4.0), 7.6–8.0 (broad s, 2H), 7.04 (d, 1H, J=4.0) 6.93 (s, 1H), 6.83 (t, 1H, J=4.0).

Elemental Analysis $C_9H_9N_5S$ Calc.: % C, 49.3; % H, 4.14; % N, 31.9; % S, 14.6 Found: % C, 49.5; % H, 4.06; % N, 32.2; % S, 14.3

2. Preparation of 2-Benzylthio[1,2,4]triazolo[1,5-a]pyridine 1-((1-Imidazolylthionyl)amino)-2-iminopyridine (9.9 g, 0.045 mol), benzyl chloride (8.6 g, 0.068 mol) and 1-propanol (100 mL) were mixed and heated to reflux for 2 hours. The solvent was removed by evaporation under reduced pressure and the residue obtained was mixed with dichloromethane. The resulting solution was washed with water and concentrated by evaporation under reduced pressure. The residue obtained was triturated with hexane to obtain 9.4 g (86 percent of theory) of the title compound as a white powder melting at 79°–81° C.

$^1$H NMR (DMSO-$d_6$): 8.85 (d, 1H, J=4.0), 7.72 (d, 1H, J=4.0), 7.63 (t, 1H, J=4.0), 7.2–7.5 (m, 5H), 7.12 (t, 1H, J=4.0), 4.50 (s, 2H); $^{13}$C NMR (DMSO-$d_6$): 163.7, 150.9, 137.6, 130.6, 129.5, 128.8, 128.7, 128.5, 128.4, 127.2, 114.6, 113.7, 34.6.

Elemental Analysis $C_{13}H_{11}N_3S$ Calc.: % C, 64.7; % H, 4.59; % N, 17.4; % S, 13.3 Found: % C, 64.5; % H, 4.86; % N, 17.3; % S, 11.8

3. Preparation of 2-Chlorosulfonyl[1,2,4]triazolo[1,5-a]pyridine

2-Benzylthio[1,2,4]triazolo[1,5-a]pyridine (8.6 g, 0.036 mol) was dissolved in dichloromethane (75 mL) and water (75 mL) and cooled in an ice bath with very good stirring. Chlorine (11.9 g, 0.168 mol) was added slowly at 3°–7° C. and was given another half hour to react. The layers were separated and the organic layer was dried over magnesium sulfate and sodium sulfate and then concentrated by evaporation under reduced pressure to obtain an oily residue. The residue was triturated with hexane to obtain 6.0 g (78 percent of theory) of the title compound as a white powder melting at 116°–118° C.

$^1$H NMR (CDCl$_3$): 8.74 (dr, 1H, J=3.4, 0.5), 7.94 (dt, 1H, J=3.4, 0.5), 7.79 (td, 1H, J=3.4, 0.5), 7.38 (td, 1H, J=3.4, 0.5); $^{13}$C NMR (CDCl$_3$): 164.2, 151.0, 132.7, 129.6, 118.5, 117.5.

4. Preparation of N-(2,6-Dichlorophenyl[1,2,4]triazolo[1,5-a]pyridine-2-sulfonamide Chlorotrimethylsilane (7.0 mL, 6.0 g, 0.055 mol), triethylamine (7.7 mL, 5.6 g, 0.055 mol) and 2,6-dichloroaniline (4.5 g, 0.027 mol) were added with stirring to a solution of anhydrous sodium iodide (8.3 g, 0.055 mol) in acetonitrile (75 mL) and the resulting mixture was stirred for another half hour. The volatile materials were removed by evaporation under reduced pressure and the residue obtained was extracted into ether. The extract was concentrated by evaporation under reduced pressure and the residue obtained was added to a solution of 2-chlorosulfonyl[1,2,4]triazolo[1,5-a]pyridine (2.0 g, 0.0092 mol) in acetonitrile (50 mL) with stirring. Dimethyl sulfoxide (130 μL, 0.144 g, 0.0018 mol) was then added and the mixture was allowed to react for 3.5 hours. The solvent was then removed by evaporation under reduced pressure and the residue obtained was diluted with dichloromethane. The resulting solution was washed well with water, dried over magnesium sulfate and concentrated by evaporation under reduced pressure. The residue obtained was triturated with hexane and the solids that formed were recovered by filtration. The solids were washed with ether and a small amount of dichloromethane to obtain 2.1 g (68 percent of theory) of the title compound as a white powder melting at 269°–270° C.

$^1$H NMR (DMSO-$d_6$): 10.86 (s, 1H), 9.08 (d, 1H, J=3.4), 7.98 (d, 1H, J=4.4), 7.82 (t, 1H, J=4.4), 7.28–7.52 (m, 4H).

Elemental Analysis $C_{12}H_8Cl_2N_4O_2S$ Calc.: % C, 42.0; % H, 2.35; % N, 16.3; % S, 9.34 Found: % C, 41.9; % H, 2.22; % N, 16.3; % S, 9.08

N-(2,6-Difluorophenyl[1,2,4]triazolo[1,5-a]pyridine-2-sulfonamide, a white powder melting at 222°–223° C., was prepared by the same procedure in 56 percent yield.

$^1$H NMR (DMSO-$d_6$): 10.75 (s, 1H), 9.07 (d, 1H, J=3.5), 7.98 (d, 1H, J=4.5), 7.83 (t, 1H, J=3.5), 7.02–7.48 (m, 5H).

Elemental Analysis $C_{12}H_8F_2N_4O_2S$ Calc.: % C, 46.5; % H, 2.60; % N, 18.1; % S, 10.3 Found: % C, 46.5; % H, 2.56; % N, 18.2; % S, 10.2

5. Preparation of 1,2-Diamino-4,6-dimethylpyridinum mesitylate

A solution of ethyl O-mesitylenesulfonylacetohydroxamate (51.0 g, 0.179 mol) in dioxane (300 mL) was cooled until the dioxane started to freeze. Seventy percent perchloric acid (22.5 mL, 0.263 mol) was then added dropwise and the reaction was allowed to warm to room temperature. After 1.5 hours the mixture was diluted with water and filtered and the collected solids were washed well with water. The damp solids were mixed with chloroform and the resulting organic solution portion of the mixture obtained was added slowly to an ice-cooled (5° C.) solution of 2-amino-4,6-dimethylpyridine (21.0 g, 0.172 mol) in chloroform (300 mL). The reaction was warmed to room temperature overnight and was then heated at reflux for several hours. The solvent was evaporated and the residue was triturated with ether and a small amount of chloroform. The resulting solid was recovered by filtration and rinsed with chloroform to obtain 22.9 g (39 percent of theory) of the title compound as a white powder melting at 193°–195° C.

Elemental Analysis $C_{16}H_{23}N_3O_2S$ Calc.: % C, 57.0; % H, 6.87; % N, 12.5; % S, 9.50 Found: % C, 57.1; % H, 7.01; % N, 12.6; % S, 9.51

$^1$H NMR (DMSO-$d_6$): 8.16 (s, 2H), 6.73 (s, 2H), 6.70 (s, 1H), 6.57 (s, 1H), 6.18 (s, 2H), 2.48 (s, 6H), 2.45 (s, 3H), 2.19 (s, 3H), 2.14 (s, 3H).

6. Preparation of 2-Benzylthio-5,7-dimethyl[1,2,4]triazolo[1,5-a]pyridine 1,2-Diamino-4,6-dimethylpyridinium mesitylate (14.0 g, 0.041 mol) and 1,1'-thiocarbonyldiimidazole (7.4 g, 0.041 mol) were mixed in chloroform (100 mL) and heated at reflux for an hour. The solvent was removed by evaporation under reduced pressure and the residue was triturated with ether and ethyl acetate and filtered to obtain 6.8 g of 1,2-diamino-4,6-dimethylpyridinium mesitylate as an insoluble solid and a filtrate. The insoluble solid was combined with another 8.3 g (15.1 g total) of the same material and with 1,1'-thiocarbonyldiimidazole (10.0 g, 0.056 mol) and the resulting mixture was stirred at room temperature for 3 days. The solvent was removed by evaporation under reduced pressure and the residue was diluted with ether and tetrahydrofuran and the mixture was filtered to obtain a filtrate. The earlier ether and ethyl acetate filtrate plus this ether and tetrahydrofuran filtrate were combined and concentrated by evaporation under reduced pressure. The resulting residue was purified by medium pressure liquid chromatography on silica gel eluting with 15 percent ethyl acetate in hexane to obtain 3.5 g (20 percent of theory) of the title compound as a white powder melting at 69°–70° C.

$^1$H NMR (CDCl$_3$): 7.1–7.5 (m, 6H), 6.5 (s, 1H), 4.5 (s, 2H), 2.6 (s, 3H), 2.4 (s, 3H); $^{13}$C NMR (CDCl$_3$): 164.1, 151.8, 140.9, 137.6, 137.1, 129.1, 128.4, 127.2, 114.7, 111.2, 35.9, 21.5, 17.4.

Elemental Analysis C$_{15}$H$_{15}$N$_3$S Calc.: % C, 66.9; % H, 5.61; % N, 15.6; % S, 11.9 Found: % C, 67.0; % H, 5.90; % N, 15.9; % S, 11.7

2-Benzylthio-7-methyl[1,2,4]triazolo[1,5-a]pyridine was prepared similarly from 1-((1-imidazolylthionyl)amino)-2-imino-4-methylpyridine. The product was a while powder melting at 81°–83° C.

$^1$H NMR (CDCl$_3$): 8.28 (d, 1H, J=3.5), 7.23–7.46 (m, 6.67 (d, 1H, J=3.5), 4.48 (s, 2H), 2.40 (s, 3H); $^{13}$C NMR (CDCl$_3$): 208.9, 164.9, 141.2, 137.2, 129.0, 128.5, 127.4, 126.7, 115.4, 113.9, 35.9, 21.5.

Elemental Analysis C$_{14}$H$_{13}$N$_3$S Calc.: % C, 65.9; % H, 5.13; % N, 16.5; % S, 12.6 Found: % C, 65.8; % H, 5.43; % N, 16.5; % S, 12.3

7. Preparation of 2-Chlorosulfonyl-5,7-dimethyl[1,2,4]triazolo[1,5-a]pyridine

2-Benzylthio-5,7-dimethyl[1,2,4]triazolo[1,5-a]pyridine (3.3 g, 0.012 mol) was mixed with dichloromethane 50 mL) and water (50 mL) with good stirring. Chlorine (4.7 g, 0.066 mol) was added slowly at 3°–6° C. and the mixture allowed to react for another half hour. The organic layer was separated, dried over a mixture of magnesium and sodium sulfates, and concentrated by evaporation under reduced pressure. The residue was triturated with hexane and the resulting solids were recovered by filtration to obtain 2.7 g of the title compound as a white powder melting at 125°–126° C.

$^1$H NMR (CDCl$_3$): 7.52 (s, 1H), 6.96 (s, 1H), 2.81 (s, 1H), 2.52 (s, 1H).

2-Chlorosulfonyl-7-methyl[1,2,4]triazolo[1,5-a]pyridine was prepared by the same procedure. An 86 percent of theory yield of this material was obtained as a pale yellow powder melting at 142°–144° C.

$^1$H NMR (CDCl$_3$): 8.57 (d, 1H, J=3.7), 7.66 (s, 1H), 7.14 (d, 1H, J=3.7), 2.57 (s, 3H).

2-Chlorosulfonyl-5-chloro-7-methyl[1,2,4]triazolo[1,5-a]pyridine was prepared similarly. A 91 percent of theory yield of this material was obtained as a pale yellow powder melting at 130°–132° C.

$^1$H NMR (CDCl$_3$): 7.62 (s, 1H), 7.25 (s, 1H), 2.57 (s, 3H). 2-Chlorosulfonyl-5,7-dichloro[1,2,4]triazolo[1,5-a]pyridine was prepared similarly. A 100 percent yield this compound was obtained as a pale yellow solid melting at 164°–166° C.

Elemental Analysis C$_6$H$_2$Cl$_2$N$_3$O$_2$S Calc.: % C, 25.2; % H, 0.70; % N, 14.7; % S, 11.2 Found: % C, 25.2; % H, 0.65; % N, 14.4; % S, 10.9

2-Chlorosulfonyl-5-chloro[1,2,4]triazolo[1,5-a]pyridine was prepared similarly. An 80 percent yield of this compound was obtained as a brownish powder melting at 102°–103° C.

2-Chlorosulfonyl-5-bromo-1,2,4-triazolo[1,5-a]pyridine was prepared similarly. An 89 percent yield of this compound was obtained as a brown powder melting at 96°–97° C.

6-Bromo-2-chlorosulfonyl-8-methoxy[1,2,4]triazolo[1,5-a]pyridine was prepared similarly. An 85 percent yield of this compound was obtained as a yellow solid.

$^1$H NMR (CDCl$_3$): 8.47 (s, 1H), 7.11 (s, 1H), 4.13 (s, 3H).

6-Chloro-2-chlorosulfonyl-8-methoxy[1,2,4]triazolo[1,5-a]pyridine was prepared similarly. An 84 percent yield of this compound was obtained as an orange gum.

$^1$H NMR (CDCl$_3$): 8.38 (d, 1H, J=1.8), 7.00 (d, 1H, J=1.8), 4.13 (s, 3H).

8-Chloro-2-chlorosulfonyl-5-methoxy[1,2,4]triazolo[1,5-a]pyridine was prepared similarly. A 96 percent yield of this compound was obtained as a tan powder melting at 147°–149° C.

8-Bromo-2-chlorosulfonyl-5-methoxy[1,2,4]triazolo[1,5-a]pyridine was prepared similarly. A 90 percent yield of this compound was obtained as a tan powder melting at 120°–122° C. with decomposition.

7-Bromo-2-chlorosulfonyl-5-methoxy[1,2,4]triazolo[1,5-a]pyridine was prepared similarly. A 95 percent yield of this compound was obtained as a tan powder melting at 113°–115° C.

8-Chloro-2-chlorosulfonyl[1,2,4]triazolo[1,5-a]pyridine was prepared similarly. An 84 percent yield of this compound was obtained as a pale yellow powder melting at 129°–131° C.

8. Preparation of 1,2-Diamino-4-methylpyridinium mesitylate

Ethyl O-mesitylenesulfonylacetohydroxamate (53.4 g, 0.191 mol) was dissolved in dioxane (300 mL) and cooled below 10° C. Perchloric acid (24.5 mL of 70 percent, 0.286 mol) was added dropwise with stirring. After 2 hours the solution was diluted with ice water and filtered to recover the solids. The damp solids were mixed with chloroform (300 mL) and the organic solution obtained was recovered and added to 2-amino-4-methylpyridine (19.6 g, 0.181 mol) in chloroform (300 mL) at 5°–10° C. The solution was warmed to room temperature for an hour. The solvent was then removed by evaporation under reduced pressure and the residue obtained was triturated with ether and then dichloromethane. The solids obtained were recovered by filtration to obtain 42.7 g (73 percent of theory) of the title compound as a white powder melting at 133°–136° C.

$^1$H NMR (DMSO-d$_6$): 8.15 (s, 2H), 7.88 (d, 1H, J=3.4), 6.61–6.83 (m, 6H), 2.49 (s, 6H), 2.26 (s, 3H), 2.16 (s, 3H).

9. Preparation of 1-((1-Imidazolylthionyl)amino)-2-imino-4-methylpyridine 1,2-Diamino-4-methylpyridinium mesitylate (1.0 g, 0.0031 mol) and 1,1'-thiocarbonyldiimidazole (0.6 g, 0.0031 mol) were mixed in chloroform (25 mL) at room temperature. After a few hours the yellow color was gone and more 1,1'-thiocarbonyldiimidazole (0.6 g, 0.0031 mol) was added and the mixture was shirred overnight. The volatiles were removed by evaporation under reduced pressure and the residue obtained was triturated with ether. The resulting solids were purified by medium pressure liquid chromatography on silica gel eluting initially with 2 percent methanol in dichloromethane and gradually changing to 5 percent methanol in dichloromethane. The solvent was removed by evaporation under reduced pressure and the residue obtained was mixed with ether. The resulting solids were recovered by filtration to obtain 0.25 g (35 percent of theory) of the title compound as an off-white powder melting at 176°–177° C.

$^1$H NMR (DMSO-d$_6$): 8.46 (s, 1H), 7.87 (s, 1H), 7.74 (d, 1H, J=3.4), 7.58 (broad s, 2H), 6.92 (s, 1H), 6.80 (s, 1H), 6.68 (dd, 1H, J=1.0, 3.4), 2.34 (s, 3H).

Elemental Analysis C$_{10}$H$_{11}$N$_5$S Calc.: % C, 51.5; % H, 4.75; % N, 30.0; % S, 13.7 Found: % C, 51.4; % H, 4.85; % N, 30.2; % S, 13.7

1-((1-Imidazolylthionyl)amino)-2-imino-3,5-dibromopyridine was prepared in the same manner. The product was obtained in 96 percent yield as a pale yellow solid melting at 185°–186° C.

$^1$H NMR (DMSO-$d_6$): 8.51 (d, 1H, J=1.8), 8.46 (s, 1H), 8.41 (d, 1H, J=2.1), 8.13 (brs, 2H), 7.86 (s, 1H), 6.93 (s, 1H).

1-((1-Imidazolylthionyl)amino)-2-imino-3,5-dichloropyridine was prepared in the same manner. The produce was obtained in 86 percent yield as a pale yellow solid melting at 176°–178° C.

Elemental Analysis $C_9H_7N_5Cl_2S$ Calc.: % C, 37.5; % H, 2.45; % N, 24.3; % S, 11.1 Found: % C, 37.7; % H, 2.50; % N, 24.0; % S, 11.2

$^1$H NMR (DMSO-$d_6$): 8.48 (s, 1H), 8.39 (s, 1H), 8.38 (s, 1H), 8.29 (brs, 2H), 7.89 (s, 1H), 6.95 (s, 1H); $^{13}$C NMR (DMSO-$d_6$): 181.1, 147.7, 138.7, 138.0, 136.4, 128.0, 120.5, 118.4, 117.8, 115.7.

10. Preparation of N-(2,6-Dichlorophenyl)-7-methyl[1,2,4]triazolo[1,5-a]pyridine-2-sulfonamide 2-Chlorosulfonyl-7-methyl[1,2,4]triazolo[1,5-a]pyridine (1.2 g, 0.0052 mol), 2,6-dichloroaniline (1.7 g, 0.010 mol) and pyridine (0.40 g, 0.0052 mol) were dissolved in anhydrous acetonitrile (20 mL). Dimethyl sulfoxide (60 µL, 0.0008 mol) was added with stirring. The reaction was allowed to stir overnight. The volatiles were removed by evaporation under reduced pressure and the residue obtained was taken up in dichloromethane. The resulting mixture was washed well with dilute aqueous hydrochloric acid and the organic solution phase was recovered and concentrated by evaporation under reduced pressure. The resulting residue was triturated with hexane and the solids that formed were recovered by filtration and dried to obtain 0.7 g (38 percent of theory) of the title compound as a tan powder melting at 232°–234° C.

Elemental Analysis $C_{13}H_{10}Cl_2N_4O_2S$ Calc.: % C, 43.7; % H, 2.82; % N, 15.7; % S, 8.98 Found: % C, 44.0; % H, 2.87; % N, 15.5; % S, 9.15.

$^1$H NMR (DMSO-$d_6$): 10.80 (s, 1H), 8.91 (d, 1H, J=3.5), 7.42 (s, 1H), 7.19–7.50 (m, 4H), 2.47 (s, 3H).

11. Preparation of 4-Methylglutaconic Anhydride

The procedure found in *J. Am. Chem. Soc.*, 75, 2377–9 (1953) was generally followed. Ethyl isodehydroacetate acetate (100 g, 0.51 mol) was added to a warm solution of sodium hydroxide (68.5 g., 0.71 mol) in water (500 mL) and stirred for an hour until the mixture became clear. The solution was acidified with concentrated hydrochloric acid (200 mL) and was extracted with ethyl acetate. The extract was dried over magnesium sulfate and concentrated by evaporation under reduced pressure. The residue was mixed with acetic anhydride (250 mL) and the resulting mixture was heated at reflux for 20–30 min. The solvent was removed by evaporation under reduced pressure and the residue obtained was crystallized from ether to obtain 60.8 g (94 percent of theory) of the title compound as a tan powder melting at 70°–72° C.

$^1$H NMR (CDCl$_3$): 6.01 (s, 1H), 3.41 (s, 2H), 2.04 (s, 3H).

The reaction works equally with methyl rather than ethyl isodehydroacetate. Acetyl chloride can be used instead of acetic anhydride, but acetic anhydride typically gave better results.

12. Preparation of 2-Benzylthio-5-hydroxy-7-methyl[1,2,4]triazolo[1,5-a]pyridine A mixture of thiosemicarbazide (50.0 g, 0.554 mol) and benzyl chloride (67.1 g, 0.53 mol) in 2-propanol (1 L) was heated to reflux with stirring for 2 hours. The reaction mixture was then cooled and 4-methylglutaconic anhydride (60.8 g, 0.482 mol) and triethylamine (75 mL, 53.6 g, 0.53 mol) were added. The reaction mixture was again heated at reflux with stirring for an hour. Sodium methoxide in methanol solution (250 mL of 25 percent, 1.09 mol) was then added and the yellow-brown mixture obtained was heated at reflux with stirring for 2.5 hours. The volatiles were removed by evaporation under reduced pressure and the residue obtained was combined with dilute aqueous acetic acid (150 mL) and ethyl acetate. The organic phase was recovered, washed well with water and concentrated by evaporation under reduced pressure. The residue obtained was heated with a heat gun under reduced pressure for 30 minutes until the bubbling had stopped and the reaction mixture had solidified. The mixture was cooled and diluted with methanol and the resulting solids were recovered by filtration to obtain 54.5 g (41 percent of theory) of the title compound as a yellow-brown powder melting at 214°–216° C.

Elemental Analysis $C_{13}H_{11}ClN_4S$ Calc.: % C, 62.0; % H, 4.83; % N, 15.5; % S, 11.9 Found: % C, 61.9; % H, 4.88; % N, 15.5; % S, 11.5

13. Preparation of 2-Benzylthio-5-chloro-7-methyl[1,2,4]triazolo[1,5-a]pyridine

N,N-Dimethylaniline (21.9 g, 0.18 mol) was added slowly to a mixture of 2-benzylthio-5-hydroxy-7-methyl[1,2,4]triazolo[1,5-a]pyridine (44.5 g, 0.164 mol) in 150 mL of phosphorus oxychloride with stirring. The mixture was heated at reflux with stirring for 20 hours. The excess phosphorus oxychloride was then removed by evaporation under reduced pressure. The residue obtained was dissolved in ethyl acetate, washed well with water and quickly concentrated by evaporation under reduced pressure to drive off the excess water. The residue was again dissolved in ethyl acetate and the resulting mixture was filtered with suction through a bed of silica gel. The filtrate was concentrated by evaporation under reduced pressure and the residue obtained was mixed with hexane. The resulting mixture was filtered to recover the solids and dried to obtain the 37.5 g. (79 percent of theory) of the title compound as a tan powder melting at 108°–110° C.

Elemental Analysis $C_{14}H_{12}ClN_3S$ Calc.: % C, 58.0; % H, 4.17; % N, 14.5; % S, 11.1 Found: % C, 58.4; % H, 3.93; % N, 14.6; % S, 11.0

$^1$H NMR (CDCl$_3$): 7.20–7.52 (m, 6H), 6.86 (s, 1H), 4.51 (s, 2H), 2.44 (s, 3H); $^{13}$C NMR (CDCl$_3$): 165.4, 152.5, 141.7, 131.2, 129.1, 128.4, 128.1, 127.3, 115.2, 112.2, 35.8, 21.4.

14. Preparation of 2-Benzylthio-5-methoxy-7-methyl[1,2,4]triazolo[1,5-a]pyridine A mixture of 2-benzylthio-5-chloro-7-methyl[1,2,4]triazolo[1,5-a]pyridine (5.0 g, 0.017 mol), sodium methoxide in methanol (16 mL of 25 percent, 3.7 g, 0.070 mol) and methanol (100 mL) were heated at reflux with stirring for 4 hours. The reaction mixture was then cooled, acidified with acetic acid (10 mL), and concentrated by evaporation under reduced pressure. The residue obtained was dissolved in dichloromethane and the resulting solution was washed well with water, dried over magnesium sulfate, and concentrated by evaporation under reduced pressure. The residue obtained was mixed with hexane and filtered to recover the solids. The solids were dried to obtain 4.7 g (97 percent of theory) of the title compound as a tan powder melting an 85°–87° C.

$^1$H NMR (CDCl$_3$): 7.24–7.46 (m, 5H), 7.02 (s, 1H), 6.06 (s, 1H), 4.51 (s, 2H), 4.10 (s, 3H), 2.43 (s, 3H).

Elemental Analysis $C_{15}H_{15}N_3OS$ Calc.: % C, 63.1; % H, 5.30; % N, 14.7; % S, 11.2 Found: % C, 62.9; % H, 5.12; % N, 14.7; % S, 11.3

15. Preparation of N-(2,6-Dichlorophenyl)-5-chloro-7-methyl[1,2,4]triazolo[1,5-a]pyridine-2-sulfonamide The title compound was prepared from 2-chlorosulfonyl-5-chloro-7-methyl[1,2,4]triazolo[1,5-a]pyridine using the procedure of Example 10. The white solid compound, which was obtained in 62 percent yield, had a melting point of 257°–258° C.

Elemental Analysis $C_{13}H_9C_{l3}N_4O_2S$ Calc.: % C, 39.9; % H, 2.32; % N, 14.3; % S, 8.19 Found: % C, 39.8; % H, 2.35; % N, 14.3; % S, 8.03

$^1$H NMR (DMSO-$d_6$): 10.80 (s, 1H), 7.81 (s, 1H), 7.60 (s, 1H), 7.03–7.48 (m, 3H), 2.48 (s, 3H).

16. Preparation of N-(2,6-Dichlorophenyl)-5-methoxy-7-methyl[1,2,4]triazolo[1,5-a]pyridine-2-sulfonamide N-(2,6-Dichlorophenyl)-5-chloro-7-methyl[1,2,4]triazolo[1,5-a]pyridine-2-sulfonamide (3.0 g, 0.0077 mol) and 25 percent sodium methoxide in methanol (12 mL, 2.8 g, 0.050 mol) were combined in methanol (100 mL) and heated to reflux with stirring for 2 hours. The reaction mixture was cooled and acidified with acetic acid and the volatiles were removed by evaporation under reduced pressure. The residue obtained was diluted with dichloromethane and the mixture was washed with water. The organic solution phase was filtered and the filtrate was concentrated by evaporation under reduced pressure. The residue obtained was mixed with ether and filtered to recover the solids. The solids were dried to obtain 2.6 g (87 percent of theory) of the title compound as a white powder melting at 269°–270° C.(d).

Elemental Analysis $C_{14}H_{12}Cl_2N_4O_3S$ Calc.: % C, 43.4; % H, 3.13; % N, 14.5; % S, 8.27 Found: % C, 43.3; % H, 3.13; % N, 14.4; % S, 8.18

$^1$H NMR (DMSO-$d_6$): 10.79 (s, 1H), 7.28–7.50 (m, 4H), 6.72 (s, 1H), 4.12 (s, 3H), 2.47 (s, 3H).

N-(2,6-Difluorophenyl)-5-methoxy-7-methyl[1,2,4]triazolo[1,5-a]pyridine-2-sulfonamide was prepared by the same procedure from N-(2,6-difluorophenyl)-5-chloro-7-methyl[1,2,4]triazolo[1,5-a]pyridine-2-sulfonamide. The product was obtained as a light tan powder melting at 248°–249° C.

Elemental Analysis $C_{14}H_{12}F_2N_4O_3S$ Calc.: % C, 47.6; % H, 3.41; % N, 15.8; % S, 9.05 Found: % C, 47.4; % H, 3.48; % N, 15.8; % S, 9.05

$^1$H NMR (DMSO-$d_6$): 10.66 (s, 1H), 7.02–7.46 (m, 4H), 6.73 (s, 1H), 4.12 (s, 3H), 2.47 (s, 3H).

17. Preparation of 2-Hydrazino-3-nitropyridine

2-Chloro-3-nitropyridine (100 g, 0.63 mol), hydrazine monohydrate (70.4 mL, 72.6 g, 1.45 mol) and methanol (1.3 L) were mixed and heated to reflux with stirring. After 30 min the reaction mixture was cooled and filtered collecting the insoluble materials. The filtrate was concentrated by evaporation under reduced pressure and the residue obtained as well as the insoluble materials from the filtration were diluted with water. The insoluble solids present were collected by filtration, washed with water, and dried to obtain 95.2 g (98 percent of theory) of the title compound as a bright yellow powder melting at 168°–169° C.

Elemental Analysis $C_5H_6N_4O_2$ Calc.: % C, 39.0; % H, 3.90; % N, 36.4; % S, 8.27 Found: % C, 39.1; % H, 4.17; % N, 36.1; % S, 8.18

18. Preparation of 2-Benzylthio-8-nitro[1,2,4]triazolo[1,5-a]pyridine

2-Hydrazino-3-nitropyridine (95.2 g, 0.618 mol) was combined with acetonitrile (1 L) and carbon disulfide (114 mL, 143.9 g, 1.89 mol) was added. The resulting mixture was stirred for 1.5 hours. Hydrogen peroxide (78.6 mL of 30 percent aqueous solution, 23.6 g, 0.693 mol) was added dropwise over a 20-min period with cooling at 15°–20° C. The mixture was stirred for another 2 hours and was then cooled in an ice bath. Benzyl chloride (91.7 g, 0.72 mol) was added and then triethylamine (110 mL, 79.6 g, 0.79 mol) was added slowly with stirring over a 2-hour period. The reaction was exothermic. The mixture was stirred at room temperature over the weekend. The volatiles were removed by evaporation under reduced pressure and the residue obtained was diluted with dichloromethane and water. The resulting mixture was filtered through Celite® to remove the precipitated sulfur. The organic phase of the filtrate was recovered, washed with water, and concentrated by evaporation under reduced pressure. The solid residue obtained was diluted with hexane, recovered by filtration, and dried to obtain 174.0 g (98 percent of theory) of the title compound as a brown powder melting at 125°–126° C.(d).

Elemental Analysis $C_{13}H_{10}N_4O_2S$ Calc.: % C, 54.5; % H, 3.52; % N, 19.6; % S, 11.2 Found: % C, 54.8; % H, 3.64; % N, 19.7; % S, 11.3

19. Preparation of 8-Amino-2-benzylthio[1,2,4]triazolo[1,5-a]pyridine

2-Benzylthio-8-nitro[1,2,4]triazolo[1,5-a]pyridine (174.0 g, 0.61 mol), iron filings (204.2 g., 3.65 mol) and acetic acid (2 L) were combined and heated with stirring at 70°–80° C. for 6 hours. The reaction mixture was cooled and diluted with water and dichloromethane. The resulting mixture was filtered through Celite®, the liquid phases in the filtrate were separated, and the aqueous layer was extracted with a little more dichloromethane. The organic phase and extract were combined and washed several times with water and then with dilute aqueous sodium hydroxide. The resulting organic solution was concentrated by evaporation under reduced pressure and the residue obtained was mixed with ether. The insoluble solids were collected by filtration and dried to obtain 106.3 g of the title compound as a brown powder melting at 116°–117° C. An additional 14.2 g of lower purity product was isolated from the ether filtrate (77 percent of theory total yield). This reduction was also carried out with iron powder and calcium chloride in aqueous ethanol and with stannous chloride in hydrochloric acid.

20. Preparation of 8-Amino-2-benzylthio-5,7-dichloro[1,2,4]triazolo[1,5-a]pyridine 8-Amino-2-benzylthio[1,2,4]triazolo[1,5-a]pyridine (20.0 g, 0.078 mol), N-chlorosuccinimide (10.4 g, 0.078 mol) and carbon tetrachloride were combined and heated to reflux with stirring for 1 hour. The reaction mixture was cooled, more N-chlorosuccinimide (10.4 g) was added, and the reaction heated to reflux with stirring for another hour. The reaction mixture was then cooled and filtered. The filtrate was concentrated by evaporation under reduced pressure and the residue obtained was purified by column chromatography on silica gel eluting with dichloromethane. The product fractions were concentrated by evaporation under reduced pressure and the residues were combined and mixed with ether. The insoluble solids were collected by filtration and dried to obtain 18.0 g (71 percent of theory) of the title compound as a light tan powder melting at 118°–119° C.

21. Preparation of 2-Benzylthio-5,7-dichloro[1,2,4]triazolo[1,5-a]pyridine

8-Amino-2-benzylthio-5,7-dichloro[1,2,4]triazolo[1,5-a]pyridine (25.8 g, 0.079 mol), t-butyl nitrite (18.9 mL, 16.4 g, 0.158 mol) and tetrahydrofuran (1.5 L) were combined and heated at reflux with stirring. Gas evolution began immediately and stopped after a few minutes, but the reaction was heated at reflux for an hour. The volatiles were removed by evaporation under reduced pressure and the residue obtained was chromatographed on silica gel eluting with dichloromethane. The product fractions were concentrated by evaporation under reduced pressure and the residue obtained was mixed with ether. The insoluble solid material was collected by filtration. The ether filtrate was concentrated by evaporation under reduced pressure and the residue was rechromatographed on silica gel eluting with 10 percent ethyl acetate in hexane. The product fractions were concentrated by evaporation under reduced pressure and the residue obtained was combined with the insoluble solid material obtained before to obtain 12.2 g (50 percent of theory) of the title compound as a red-brown powder melting at 88°–89° C.

Elemental Analysis $C_{13}H_9Cl_2N_3S$ Calc: % C, 50.3; % H, 2.92; % N, 13.6; % S, 10.3 Found: % C, 50.1; % H, 2.92; % N, 13.6; % S, 10.2

2-Benzylthio-5,7-dibromo[1,2,4]triazolo[1,5-a]pyridine was prepared similarly from 8-amino-2-benzylthio-5,7-dibromo[1,2,4]triazolo[1,5-a]pyridine. A 32 percent yield of this compound was obtained as a light tan powder melting at 113°–114° C.

22. Preparation of N-(2,6-Dichlorophenyl)-5-methoxy-7-chloro[1,2,4]triazolo[1,5-a]pyridine-2-sulfonamide Sodium methoxide in methanol (1.1 mL of 25 percent solution, 0.26 g, 0.005 mol) was added to a solution of N-(2,6-dichlorophenyl)-5,7-dichloro[1,2,4]triazolo[1,5-a]pyridine-2-sulfonamide (0.9 g, 0.02 mol) in dimethyl sulfoxide (30 mL) at ambient temperature with stirring. The reaction was complete in a few minutes, but was stirred for 30 min. The mixture was then acidified with acetic acid and diluted with dichloromethane. The resulting organic phase was recovered and washed with water and the volatiles were removed by evaporation under reduced pressure. The residue obtained was mixed with hexane and the insoluble solids were collected by filtration and dried to obtain 0.8 g (90 percent of theory) of the title compound as a light tan powder melting at 232°–234° C.(d).

Elemental Analysis $C_{13}H_9Cl_3N_4O_3S$ Calc.: % C, 38.3; % H, 2.22; % N, 13.7; % S, 7.87 Found: % C, 38.3; % H, 2.12; % N, 13.7; % S, 7.63

23. Preparation of N-(2,6-Dichlorophenyl)-5,7-dimethoxy[1,2,4]triazolo[1,5-a]pyridine-2-sulfonamide Sodium methoxide in methanol (3.0 mL of 25 percent solution, 0.71 g, 0.013 mol) was added to a solution of N-(2,6-dichlorophenyl)-5-methoxy-7-chloro[1,2,4]triazolo[1,5-a]pyridine-2-sulfonamide (0.66 g, 0.0016 mol) in dimethyl sulfoxide (30 mL) with stirring over several hours. The mixture was allowed to react and was then acidified with acetic acid and diluted with dichloromethane. The resulting organic phase was recovered and washed with water and the volatiles were removed by evaporation under reduced pressure. The residue obtained was chromatographed on silica gel starting with 0.5 percent acetic acid in dichloromethane and gradually increasing the strength to 0.5 percent acetic acid plus 1.0 percent ethanol in dichloromethane. The product fractions were concentrated by evaporation under reduced pressure to obtain 118 mg (13 percent of theory) of the title compound as a pale yellow powder melting at 252°–253° C.(d).

Elemental Analysis $C_{14}H_{12}Cl_2N_4O_4S$ Calc.: % C, 41.7; % H, 3.00; % N, 13.9; % S, 7.95 Found: % C, 41.8; % H, 2.67; % N, 13.6; % S, 8.00

24. Preparation of N-(2-fluoro-5-methyl-3-pyridinyl)-5-methoxy-7-methyl[1,2,4]triazolo[1,5-a]pyridine-2-sulfonamide To a solution of 0.70 g (1.9 mmol) of N-(2-fluoro-5-methyl-3-pyridinyl)-5-chloro-7-methyl[1,2,4]triazolo[1,5-a]pyridine-2-sulfonamide in 25 mL of dry dimethyl sulfoxide was added with stirring 1.0 mL (4.6 mmol) of sodium methoxide as a 25 percent solution in methanol. After 3 min, 3 mL of acetic acid was added and the solution was diluted with 600 mL of dichloromethane. The resulting solution was washed with water (5×100 mL), dried over magnesium sulfate, filtered, and concentrated by evaporation under reduced pressure to obtain 0.5 g (71 percent of theory) of the title compound as a white solid melting at 262°–264° C. with decomposition.

Elemental Analysis $C_{13}H_{11}ClFN_5O_3S$ Calc.: % C, 42.0; % H, 2.98; % N, 18.8; % S, 8.62 Found: % C, 41.9; % H, 2.93; % N, 18.8; % S, 8.47

$^1$H NMR (DMSO-$d_6$): 10.7 (br, 1H), 8.1 dd, 1H), 8.05 (dd, 1H), 7.4 (s, 1H), 6.8 (s, 1H), 4.1 (s, 1H), 2.5 (s, 3H).

25. Preparation of 8-Amino-2-benzylthio-5-chloro[1,2,4]triazolo[1,5-a]pyridine

A solution of 8-amino-2-benzylthio[1,2,4]triazolo[1,5-a]pyridine (14.0 g, 0.0546 mol) and 1,3-dichloro-5,5-dimethylhydantoin (5.4 g, 0.0273 mol) were combined in 500 mL of dichloromethane and the mixture was heated at reflux with stirring for two hours. Additional 1,3-dichloro-5,5-dimethylhydantoin (5.0 g, 0.025 mol) was added and the reaction was heated with stirring for an additional hour. The reaction mixture was cooled and dilute aqueous sodium bisulfite was added with stirring and allowed to react for an hour. The mixture was then washed with water and the volatiles were removed by evaporation under reduced pressure. The residue obtained was chromatographed on silica gel eluting with dichloromethane to obtain 6.0 g (38 percent of theory) of the title compound as a light tan powder melting at 113°–114° C.

Elemental Analysis $C_{13}H_{11}ClN_4S$ Calc.: % C, 53.7; % H, 3.81; % N, 19.3; % S, 11.0 Found: % C, 53.9; % H, 3.84; % N, 19.5; % S, 11.0

26. Preparation of 2-Benzylthio-5-chloro[1,2,4]triazolo[1,5-a]pyridine

A solution of 8-amino-2-benzylthio-5-chloro[1,2,4]triazolo[1,5-a]pyridine (9.0 g, 0.031 mol) and acetic acid (2.0 g, 0.033 mol) in tetrahydrofuran (100 mL) was added dropwise with stirring over 30 min to a solution of t-butyl nitrite (6.4 g, 0.062 mol) in tetrahydrofuran (500 mL) at 50°–55° C. and allowed to react another 15 minutes after the addition was complete. The volatiles were removed by evaporation under reduced pressure and the residue obtained was chromatographed on silica gel eluting with a gradient of 5–15 percent ethyl acetate in hexane. The product fractions were concentrated by evaporation under reduced pressure to obtain 3.4 g (37 percent of theory) the title compound as a dark low-melting solid.

27. Preparation of 8-Amino-2-benzylthio-5-bromo[1,2,4]triazolo[1,5-a]pyridine

8-Amino-2-benzylthio[1,2,4]triazolo[1,5-a]pyridine (25.6 g, 0.1 mol), N-bromosuccinimide (17.8 g, 0.1 mol) and 2 L of dichloromethane were combined with stirring for an hour. The solution was washed with dilute aqueous sodium bisulfite and then with water and the volatiles were removed by evaporation under reduced pressure. The residue obtained was chromatographed on silica gel eluting with 25 percent ethyl acetate in hexane. The product fractions were concentrated by evaporation under reduced pressure and the solid residue obtained was extracted with ether and dried to obtain 17.5 g (52 percent of theory) of the title compound as a light tan powder melting at 125°–126° C.

Elemental Analysis $C_{13}H_{11}BrN_4S$ Calc.: % C, 46.6; % H, 3.31; % N, 16.7; % S, 9.56 Found: % C, 46.7; % H, 3.34; % N, 17.0; % S, 9.56

28. Preparation of 8-Amino-2-benzylthio-5-chloro[1,2,4]triazolo[1,5-a]pyridine by Reduction A mixture of 1.0 g (3.5 mmol) of 2-benzylthio-8-nitro[1,2,4]triazolo[1,5-a]pyridine, 1.35 g (3.85 mmol) of stannic chloride pentahydrate, and 10 mL of concentrated hydrochloric acid was prepared and heated to 90° C. with stirring. A solution of 1.99 g (10.5 mmol) of stannous chloride in 10 mL of concentrated aqueous hydrochloric acid was added slowly over a 1-hour period. After a short reaction period the mixture was allowed to cool and the solids present were collected by filtration. The collected solids were placed in water and the mixture was basified with dilute aqueous sodium hydroxide. The resulting mixture was extracted with dichloromethane and the organic extract was concentrated by evaporation under reduced pressure to obtain 0.60 g (66 percent of theory) of product as a brown solid. This solid was found to be 93 percent the title compound and 7 percent 8-amino-2-benzylthio[1,2,4]triazolo[1,5-a]pyridine by high pressure liquid chromatography. The pure compound melts at 113°–114° C.

29. Preparation of 8-Amino-2-benzylthio-5-ethoxy[1,2,4]triazolo[1,5-a]pyridine by Reduction 2-Benzylthio-8-nitro[1,2,4]triazolo[1,5-a]pyridine (5.0 g, 0.017 mol) and stannic chloride petrahydrate (7.3 g, 0.021 mol) were mixed with 100 mL of ethanol and the mixture was heated to reflux with stirring. A solution of stannous chloride (13.2 g, 0.07 mol) in 100 mL of ethanol was added dropwise with stirring over 45 minutes and the heating was continued another 20 minutes after the addition was complete. The reaction mixture was diluted with dichloromethane. The resulting mixture was washed well with 2N aqueous hydrochloric acid and was then concentrated by evaporation under reduced pressure. The residue was chromatographed on silica gel eluting first with 5 percent ethyl acetate in dichloromethane and gradually increasing to 20 percent ethyl acetate in dichloromethane. The product fractions were concentrated by evaporation under reduced pressure and the residue was dissolved in dichloromethane. The resulting solution was washed well with 2N aqueous sodium hydroxide, dried over magnesium sulfate, and concentrated by evaporation under reduced pressure. The residue was mixed with hexane and the insoluble solids were recovered by filtration and dried to obtain 1.7 g (33 percent of theory) of the title compound as a dark tan powder melting at 106°–107° C.

Elemental Analysis $C_{15}H_{16}N_4OS$ Calc.: % C, 60.0; % H, 5.37; % N, 18.7; % S, 10.7 Found: % C, 59.8; % H, 5.49; % N, 18.8; % S, 10.5

30. Preparation of 1,2-Diamino-3,5-dichloropyridinium Mesitylate

2-Amino-3,5-dichloropyridine (9.48 g, 58.1 mmol) was dissolved in chloroform (100 mL) in a round bottom flask and the mixture was cooled to 5° C. in an ice bath. To this mixture was added dropwise with stirring a freshly prepared solution of O-mesitylenesulfonylhydoxylamine (15.5 g, 69.8 mmol) in chloroform. (warning; this compound is an explosive solid). A thick white precipitate began to form after 15 min. The mixture was allowed to warm to room temperature while stirring overnight. The solids present were recovered by filtration, washed with chloroform (3×100 mL), and dried to obtain 17.5 g (80 percent of theory) of the title compound as a white crystalline solid melting at 231°–232° C.

Infrared Analysis (KBr): 3407, 3203, 3025, 2936, 1656, 1369, 1182, 1086, 1014, 679, 600, 548 cm$^{-1}$;

$^1$H NMR (DMSO-d$_6$): 8.81 (s, 2H), 8.42 (s, 2H), 7.01 (s, 2H), 6.73 (s, 2H), 2.50 (s, >6H), 2.16 (s, 3H).

1,2-Diamino-3,5-dibromopyridinium mesitylate was prepared similarly and was obtained in 92 percent yield as an off-white solid melting at 212°–213° C.

$^1$H NMR (DMSO-d$_6$): 8.67 (brs, 2H), 8.58 (d, 1H, J=2.1), 8.47 (d, 1H, J=2.1), 6.99 (s, 2H), 6.74 (s, 2H), 2.49 (s, >6H), 2.17 (s, 3H).

Elemental Analysis $C_{14}H_{17}Br_2N_3O_3S$ Calc.: % C, 36.1; % H, 3.68; % N, 9.01; % S, 6.88 Found: % C, 35.9; % H, 3.98; % N, 8.89; % S, 6.86

31. Preparation of 2-Benzylthio-6,8-dichloro[1,2,4]triazolo[1,5-a]pyridine 1-((1-Imidazolylthionyl)amino)-2-imino-3,5-dichloropyridine (1.0 g, 3.5 mmol) was combined with n-butanol (10 mL) in a round bottom flask and heated to 100° C. with stirring. Benzyl chloride (0.48 mL, 4.2 mmol) was added and the mixture was heated at reflux with stirring for 1.5 hour. The volatiles were then removed by evaporation under reduced pressure and the solid residue obtained was triturated with hexane (20 mL), water (20 mL), and hexane (20 mL). The resulting solid was washed with hexane on a filter and dried to obtain 0.80 g (74 percent of theory) of the title compound as a pale yellow solid melting at 115°–116° C.

Elemental Analysis $C_{13}H_9N_3Cl_2S$ Calc.: % C, 50.3; % H, 2.92; % N, 13.6; % S, 10.3 Found: % C, 49.4; % H, 2.32; % N, 13.8; % S, 10.1

$^1$H NMR (DMSO-d$_6$): 9.28 (s, 1H), 8.08 (s, 1H), 7.46 (d, 2H, J=7.2), 7.27–7.31 (m, 3H), 4.50 (s, 2H); $^{13}$C NMR (DMSO-d$_6$): 164.9, 148.2, 137.2, 130.5, 128.9, 128.5, 127.4, 126.5, 119.7, 119.4, 34.7.

2-Benzylthio-6,8-dibromo[1,2,4]triazolo[1,5-a]pyridine was prepared similarly. The product was obtained in 84 percent yield as a pale yellow solid melting at 122°–124° C.

Elemental Analysis $C_{13}H_9N_3Br_2S$ Calc.: % C, 39.1; % H, 2.27; % N, 10.5; % S, 8.03 Found: % C, 38.8; % H, 2.34; % N, 10.6; % S, 8.17

$^1$H NMR (DMSO-d$_6$): 9.34 (d, 1H, J=1.8), 8.23 (d, 1H, J=1.5), 7.47 (d, 2H, J=6.9), 7.25–7.33 (m, 3H), 4.49 (s, 2H).

32. Preparation of 2-Benzylthio-6-bromo-8-methoxy[1,2,4]triazolo[1,5-a]pyridine

2-Benzylthio-6,8-dibromo[1,2,4]triazolo[1,5-a]pyridine (9.5 g, 23.8 mmol) was mixed with acetonitrile (50 mL) in a round bottom flask. Sodium methoxide (13.1 mL of 25 percent solution in methanol, 57.1 mmol) was added and the mixture was heated at reflux for 2 hours. Glacial acetic acid (10 mL) was added and the entire reaction mixture was poured into a mixture of ice and water (300 mL). The brown precipitate that formed was recovered by filtration and dried. This was chromatographed on silica gel eluting with a 1:1 mixture of ethyl acetate and hexane. Product-containing fractions were combined and concentrated under reduced pressure to obtain 6.58 g (80 percent of theory) of the title compound as a pale yellow solid.

Elemental Analysis $C_{14}H_{12}N_3BrSO$ Calc.: % C, 48.0; % H, 3.45; % N, 12.0; % S, 9.75 Found: % C, 47.8; % H, 3.36; % N, 11.9; % S, 9.22

$^1$H NMR (DMSO-d$_6$): 8.85 (d, 1H, J=1.5), 7.42 (d, 2H, J=7.5), 7.23–7.31 (m, 4H), 4.46 (s, 2H), 3.97 (s, 3H).

2-Benzylthio-6-chloro-8-methoxy[1,2,4]triazolo[1,5-a]pyridine was prepared similarly. The product was obtained in 87 percent yield as a tan solid melting at 125°–126° C.

$^1$H NMR (DMSO-d$_6$): 8.84 (d, 1H, J=1.5), 7.46 (d, 2H, J=6.9), 7.26–7.36 (m, 2H), 7.24 (d, 1H, J=1.5), 4.50 (s, 2H), 4.02 (s, 3H).

2-Benzylthio-6-chloro-8-ethoxy[1,2,4]triazolo[1,5-a]pyridine was prepared similarly. The product was obtained in 100 percent yield as a pale orange oil.

$^1$H NMR (DMSO-d$_6$): 8.83 (d, 1H, J=1.2), 7.45 (d, 2H, J=7.2), 7.26–7.34 (m, 3H), 7.22 (d, 9H, J=1.2), 1H), 4.49 (s, 2H), 4.28 (q, 2H, J=7.2), 1.41 (t, 3H, J=6.9).

33. Preparation of 6-Bromo-5-chloro-2-chlorosulfonyl-8-methoxy[1,2,4]triazolo[1,5-a]pyridine 2-Benzylthio-6-bromo-8-methoxy[1,2,4]triazolo[1,5-a]pyridine (2.0 g, 5.7 mmol) was dissolved in dichloromethane (30 mL) in a three-necked flask equipped with high-speed stirrer and a dry ice condenser and was cooled in an ice bath to 5° C. Aqueous hydrochloric acid (2N, 30 mL, 60 mmol) and then sodium hypochlorite (5 percent aqueous solution, 50 mL, 34 mmol) were added with stirring. The mixture was allowed to react for 2 hours. The layers were then separated and the aqueous layer was washed with dichloromethane (2×10 mL). The dichloromethane layer and wash were combined, washed with water (20 mL) and saturated aqueous sodium chloride solution (20 mL), and concentrated by evaporation under reduced pressure to obtain a gum. This was triturated with hexane to obtain 1.94 g (97 percent of theory) of the title compound as a yellow gum.

$^1$H NMR (CDCl$_3$): 7.14 (s, 1H); 4.13 (s, 3H).

34. Preparation of 2-Benzylthio-5,8-dichloro[1,2,4]triazolo[1,5-a]pyridine

A mixture of 9.9 g (0.10 mol) of copper(I) chloride with 300 mL of acetonitrile was prepared and 8.7 mL (6.8 g, 0.066 mol) of 90 percent t-butyl nitrite was added with stirring. After 10 minutes 9.5 g (0.033 mol) of 8-amino-2-benzylthio-5-chloro[1,2,4]triazolo[1,5-a]pyridine was added and the reaction mixture was allowed to react with stirring for 3 days. The mixture was then diluted with dichloromethane and 2N aqueous hydrochloric acid, and after mixing this well, the phases were separated. The organic layer was washed with 2N aqueous hydrochloric acid and concentrated by evaporation under reduced pressure. The residue was chromatographed on silica gel eluting with dichloromethane to obtain 6.5 g (63 percent of theory) of the title compound as a yellow powder melting at 103°–104° C.

Elemental Analysis C$_{13}$H$_9$Cl$_2$N$_3$S Calc.: % C, 50.3; % H, 2.92; % N, 13.6; % S, 10.3 Found: % C, 50.4; % H, 2.08; % N, 13.6; % S, 10.3

2-Benzylthio-8-chloro[1,2,4]triazolo[1,5-a]pyridine was prepared similarly from 8-amino-2-benzylthio[1,2,4]triazolo[1,5-a]pyridine. A 65 percent yield of this compound was obtained as a yellow powder melting at 82°–83° C.

Elemental Analysis C$_{13}$H$_{10}$ClN$_3$S Calc.: % C, 56.6; % H, 3.66; % N, 15.2; % S, 11.6 Found: % C, 56.6; % H, 3.33; % N, 15.3; % S, 11.5

35. Preparation of 2-Benzylthio-8-chloro-5-methoxy[1,2,4]triazolo[1,5-a]pyridine 2-Benzylthio-5,8-dichloro[1,2,4]triazolo[1,5-a]pyridine (6.0 g, 0.019 mol) and 25 percent sodium methoxide in methanol (26.5 mL, 6.3 g, 0.116 mol) were combined in methanol and the mixture was heated to reflux for 2 hours. The mixture was then cooled, acidified with acetic acid, and concentrated by evaporation under reduced pressure. The residue was dissolved in dichloromethane and the solution was washed with water and concentrated by evaporation under reduced pressure. The residue was triturated with hexane and the resulting solids were collected by filtration and dried to obtain 5.76 g (99 percent of theory) of the title compound as a light tan powder melting at 90°–91° C.

Elemental Analysis C$_{14}$H$_{12}$ClN$_3$OS Calc.: % C, 55.0; % H, 3.96; % N, 13.7; % S, 10.5 Found: % C, 54.9; % H, 4.02; % N, 13.4; % S, 10.7

36. Preparation of 2-Benzylthio-8-bromo-5-chloro[1,2,4]triazolo[1,5-a]pyridine Copper(I) bromide (4.9 g., 0.0034 mol) was combined with 200 mL of acetonitrile for 15 minutes and then 3.0 mL (2.3 g, 0.0023 mol) of 90 percent t-butyl nitrite was added and the mixture was stirred for a few minutes. 8-Amino-2-benzylthio-5-chloro[1,2,4]triazolo[1,5-a]pyridine (3.3 g, 0.0013 mol) was then added and the resulting mixture was stirred for 2 days. The resulting mixture was concentrated by evaporation under reduced pressure and the residue was chromatographed on silica gel eluting with dichloromethane. After the solvent of the product fractions was removed by evaporation under reduced pressure, the residue was mixed with hexane and the solid material was recovered by filtration and dried to obtain 2.6 g (56 percent of theory) of the title compound as a yellow powder melting at 122°–124° C.

Elemental Analysis C$_{13}$H$_9$BrClN$_3$S Calc.: % C, 44.0; % H, 2.56; % N, 11.9; % S, 9.04 Found: % C, 43.9; % H, 2.59; % N, 11.9; % S, 8.86

37. Preparation of 2-Benzylthio-8-bromo-5-methoxy[1,2,4]triazolo[1,5-a]pyridine 2-Benzylthio-8-bromo-5-chloro[1,2,4]triazolo[1,5-a]pyridine (7.7 g, 0.0217 mol) and 25 percent sodium methoxide in methanol (19.9 mL, 4.7 g, 0.0868 mol) were mixed with 400 mL of methanol and the mixture was heated to reflux for 1.5 hours. It was then cooled and acidified with acetic acid. The volatiles were removed by evaporation under reduced pressure and the residue was dissolved in dichloromethane. The resulting solution was washed with water and concentrated by evaporation under reduced pressure. The resulting residue was triturated with hexane and the solids obtained were recovered by filtration and dried to obtain 7.3 g (96 percent of theory) of the title compound as a light tan powder melting at 78°–79° C.

Elemental Analysis C$_{14}$H$_{12}$BrN$_3$OS Calc.: % C, 48.0; % H, 3.45; % N, 12.0; % S, 9.16 Found: % C, 48.0; % H, 3.52; % N, 12.2; % S, 9.01

38. Preparation of N-(2,6-Difluorophenyl)-8-methoxy[1,2,4]triazolo[1,5-a]pyridine-2-sulfonamide N-(2,6-Difluorophenyl)-8-chloro[1,2,4]triazolo[1,5-a]pyridine-2-sulfonamide (0.8 g, 0.0023 mol) and 25 percent sodium methoxide in methanol (1.6 mL, 0.37 g, 0.007 mol) were combined with 20 mL of dimethyl sulfoxide and the resulting solution was stirred at ambient temperature overnight. Another 1.6 mL of 25 percent sodium methoxide in methanol was added and the reaction mixture was stirred another 3 days. The mixture was then acidified with acetic acid and diluted with dichloromethane. The resulting solution was washed well with water and concentrated by evaporation under reduced pressure. The residue, which appeared to contain considerable starting material, was dissolved in 20 mL of dimethyl sulfoxide and potassium methoxide (0.4 g, 0.0057 mol) was added with stirring at ambient temperature. After about 3 hours the mixture was acidified with acetic acid and diluted with dichloromethane. The resulting solution was washed well with water and concentrated by evaporation under reduced pressure. The residue was mixed with hexane and the solids present were collected by filtration, washed with ether and with dichloromethane and dried to obtain 0.30 g (38 percent of theory) of the title compound as a white powder melting at 254°–255° C.

Elemental Analysis C$_{13}$H$_{10}$F$_2$N$_4$O$_3$S Calc.: % C, 45.9; % H, 2.96; % N, 16.5; % S, 9.42 Found: % C, 45.9; % H, 2.55; % N, 16.4; % S, 9.34

39. Preparation of 8-Amino-2-benzylthio-5,7-dibromo[1,2,4]triazolo[1,5-a]pyridine 8-Amino-2-benzylthio[1,2,4]triazolo[1,5-a]pyridine (14.0 g, 0.055 mol) was dissolved in dichloromethane and N-bromosuccinimide (9.7 g., 0.055 mol) was added with stirring at ambient temperature. After 1 hour, another 6.0 g of N-bromosuccinimide was added. The mixture was allowed To stir overnight and was then washed well with dilute aqueous sodium bisulfite solution and with water and concentrated by evaporation under reduced pressure. The residue was chromatographed on silica gel eluting with 30 percent ethyl acetate in hexane to obtain 10.0 g (44 percent of theory) of the title compound as a dark gray powder melting at 116°–118° C.

40. Preparation of 2-Benzylthio-7-bromo-5-methoxy[1,2,4]triazolo[1,5-a]pyridine

2-Benzylthio-5,7-dibromo[1,2,4]triazolo[1,5-a]pyridine (11.6 g, 0.029 mol) and 25 percent sodium methoxide in methanol (13.0 mL, 3.1 g, 0.057 mol) were combined with 300 mL of acetonitrile and the mixture was heated to reflux with stirring for an hour. An additional 26 mL of 25 percent sodium methoxide in methanol was then added. After a 15-min reaction period, the mixture was acidified with acetic acid and the volatiles were removed by evaporation under reduced pressure. The residue was chromatographed on silica gel eluting with 20 percent ethyl acetate in hexane to obtain 4.97 g (49 percent of theory) of the title compound as a tan powder melting at 80°–82° C.

Elemental Analysis $C_{14}H_{12}BrN_3OS$ Calc.: % C, 48.0; % H, 3.45; % N, 12.0; % S, 9.16 Found: % C, 48.2; % H, 3.42; % N, 11.9; % S, 9.24

41. Preparation of 3-Amino-2-fluoro-4-methylpyridine

To a solution of 10.1 g (65 mmol) of 2-fluoro-4-methyl-3-nitropyridine in 200 mL of ethyl acetate was added 25 g (0.40 mol) of acetic acid and 0.8 g of 5 percent palladium on carbon catalyst. This mixture was shaken under 50 psig (pounds per square inch gauge, 2400 kiloPascals) pressure of hydrogen for 18 hours, was filtered, and was concentrated by evaporation under reduced pressure to obtain an oil. This oil was partitioned between dilute aqueous sodium bicarbonate and ether. The organic phase was separated, dried over magnesium sulfate, and filtered. The filtrate was concentrated by evaporation under reduced pressure and the residue was purified by column chromatography to obtain 7.2 g (88 percent of theory) of the title compound as a colorless solid melting at 63°–64° C.

Elemental Analysis $C_6H_7FN_2$ Calc.: % C, 57.1; % H, 5.59; % N, 22.2 Found: % C, 57.2; % H, 5.73; % N, 22.1

$^1$H NMR $CDCl_3$: 7.4 (d, 1H, J=5.0); 6.8 (d, 1H, J=5.0); 3.7 (br, 2H); 2.1 (s, 3H); $^{13}$C NMR $CDCl_3$: 152.6 (d, J=229); 134.1 (d, J=8.6); 133.8 (d, J=14.5); 128.1 (d, J=27.1); 123.3, 16.4 (d, J=4.1).

3-Amino-2-fluoro-5-methylpyridine was prepared analogously from 2-fluoro-5-methyl-3-nitropyridine. This compound was obtained in 89 percent yield as white solid melting at 27°–28.5° C.

Elemental Analysis $C_6H_7FN_2$ Calc.: % C, 57.1; % H, 5.59; % N, 22.2 Found: % C, 56.9; % H, 5.65; % N, 22.6

$^1$H NMR $CDCl_3$: 7.2 (d, 1H); 6.8 (d, 1H); 3.7 (br, 2H); 2.1 (s, 3H); $^{13}$C NMR $CDCl_3$: 151.8 (d, J=229); 134.5 (d, J=12.6); 132.2 (d, J=3.9); 129.9 (d, J=28.7); 125.8 (d, J=5.3), 17.8.

42. Preparation of 3-Amino-2-chloro-4-methoxypyridine

To a solution of 6.4 g (51 mmol) of 3-amino-4-methoxypyridine in 30 mL of 37 percent aqueous hydrochloric acid was slowly added 7.8 g of 30 percent aqueous hydrogen peroxide at room temperature with stirring. After 30 min this solution was slowly poured into 300 mL of saturated aqueous sodium bicarbonate and the resulting mixture was extracted with ether (3×200 mL). The ethereal extracts were combined, dried over magnesium sulfate, and filtered. The filtrate was concentrated by evaporation under reduced pressure to obtain a light brown solid. This solid was purified by column chromatography eluting with 17:83 acetone:hexane to obtain 6.54 g (81 percent of theory) of the title compound as colorless needles melting at 86°–87° C.

Elemental Analysis $C_6H_7ClN_2O$ Calc.: % C, 45.4; % H, 4.45; % N, 17.7 Found: % C, 45.4; % H, 4.65; % N, 17.8

$^1$H NMR $CDCl_3$: 7.7 (d, 1H, J=5.4), 6.6 (d, 1H, J=5.4), 4.0 (br, 2H), 3.8 (s, 3H); $^{13}$C NMR $CDCl_3$: 153.3, 138.5, 135.6, 129.9, 105.2, 55.9.

3-Amino-2-chloro-4-ethoxypyridine was prepared from 3-amino-4-ethoxypyridine in an analogous procedure and was obtained as a white solid melting at 72°–73° C.

Elemental Analysis $C_7H_9ClN_2O$ Calc.: % C, 48.7; % H, 5.26; % N, 16.2 Found: % C, 48.9; % H, 4.98; % N, 16.5

$^1$H NMR $CDCl_3$: 7.7 (d, 1H, J=5.4), 6.6 (d, 1H, J=5.4), 4.1 (q, 2H, J=7.0), 4.0 (br, 2H), 1.5 (t, 3H, J=7.0).

3-Amino-2-chloro-4-propoxypyridine was prepared from 3-amino-4-propoxypyridine in an analogous procedure and was obtained as a white solid melting at 46°–47° C.

Elemental Analysis $C_8H_{11}ClN_2O$ Calc.: % C, 51.5; % H, 5.94; % N, 15.0 Found: % C, 51.8; % H, 5.97; % N, 15.2

$^1$H NMR $CDCl_3$: 7.7 (d, 1H, J=5.4), 6.6 (d, 1H, J=5.4), 4.1 (br, 2H), 4.0 (t, 2H, J=6.5), 1.84 (m, 2H), 1.0 (t, 3H, J=7.4).

3-Amino-2-chloro-4-(1-methylethoxy)pyridine was prepared from 3-amino-4-(1-methylethoxy)pyridine in an analogous procedure and was obtained as an amber oil.

Elemental Analysis $C_8H_{11}ClN_2O$ Calc.: % C, 51.5; % H, 5.94; % N, 15.0 Found: % C, 51.1; % H, 5.87; % N, 15.4

$^1$H NMR $CDCl_3$: 7.7 (d, 1H, J=5.5), 6.6 (d, 1H, J=5.4), 4.6 (m, 1H, J=6.0), 4.0 (br, 2H), 1.34 (d, 6H, J=6.0).

43. Preparation of 3-Amino-2-ethylthio-4-methylpyridine

2-Ethylthio-4-methyl-3-nitropyridine (10.0 g, 50.4 mmol) was added slowly with stirring to a solution of 57 g (0.25 mole) of stannous chloride in 250 mL of concentrated aqueous hydrochloric acid. An exothermic reaction took place. The solution was held at 70° C. for 30 min, cooled, and then poured slowly into saturated aqueous sodium bicarbonate solution. The resulting mixture was extracted with ember and the extract was dried over magnesium sulfate, filtered, and concentrated by evaporation under reduced pressure to obtain 5.8 g (68 percent of theory) of a light yellow oil that solidified upon standing. This solid was recrystallized from hexane to obtain 3.2 g of the title compound as a white solid melting at 37°–38° C.

Elemental Analysis $C_8H_{12}N_2S$ Calc.: % C, 57.1; % H, 7.19; % N, 16.7; % S, 19.1 Found: % C, 57.3; % H, 6.88; % N, 16.8; % S, 19.0

$^1$H NMR $CDCl_3$: 7.8 (d, 1H, J=4.8), 6.7 (d, 1H, J=4.8), 3.8 (br, 2H), 3.2 (q, 2H, J=7.4), 2.1 (s, 3H), 1.3 (t, 3H, J=7.4); $^{13}$C NMR $CDCl_3$: 142.2, 139.5, 139.3, 128.9, 122.4, 25.4, 17.0, 15.0.

44. Preparation of Methyl 3-Amino-2-chloroisonicotinate

A mixture of 18 g (118 mmol) of methyl 3-aminoisonicotinate and 12 g (60 mmol) of 1,3-dichloro-5,5-dimethylhydantoin in 1500 mL of tetrachloroethylene was warmed slowly to 80° C. with stirring and held there for 3 hours. The solution was then cooled, filtered, washed with dilute aqueous sodium bicarbonate, dried over magnesium sulfate, filtered, and concentrated by evaporation under reduced pressure to obtain a dark oil. This oil was purified by careful column chromatography to obtain 6.7 g (30 percent of theory) of the title compound as a colorless solid melting at 91°–92° C.

Elemental Analysis $C_7H_7ClN_2O_2$ Calc.: % C, 45.1; % H, 3.78; % N, 15.0 Found: % C, 45.2; % H, 3.94; % N, 15.1

$^1$H NMR $CDCl_3$: 7.7 (d, 1H, J=5.1); 7.6 (d, 1H, J=5.1); 6.2 (br, 2H); 3.9 (s, 3H); $^{13}$C NMR $CDCl_3$: 166.7, 141.9, 139.0, 134.7, 122.8, 116.5, 52.3.

45. Preparation of 3-Amino-4-ethyl-2-fluoropyridine

Trimethylsilyl chloride (2.2 g, (0.18 mmol) and sodium iodide (2.7 g, 0.18 mmol) were added to a solution of 3.6 g (0.15 mmol) of t-butyl N-(4-ethyl-2-fluoro-3-pyridyl) carbamate in 50 mL of dry acetonitrile with stirring at ambient temperature. After 2 hours the mixture was poured into ether and the resulting solution was washed with dilute aqueous sodium bisulfite, dried over magnesium sulfate, and filtered. The filtrate was concentrated by evaporation under reduced pressure to obtain an oil. This oil was purified by column chromatography to obtain 1.6 g (76 percent of theory) of the title compound as a gold oil.

Elemental Analysis $C_7H_9FN_2$ Calc.: % C, 60.0; % H, 6.47; % N, 20.0 Found: % C, 59.8; % H, 6.66; % N, 20.2

$^1$H NMR $CDCl_3$: 7.4 (d, 1H, J=5.0); 6.8 (d, 1H, J=5.0); 3.7 (br, 2H); 2.45 (q, 2H, J=7.5); 1.2 (t, 3H, J=7.5).

3-Amino-4-(1-methylethyl)-2-fluoropyridine was prepared in an analogous way from t-butyl N-(4-(1-methylethyl)-2-fluoro-3-pyridyl)carbamate. This compound was obtained in 92 percent yield as a gold oil.

Elemental Analysis $C_8H_{11}FN_2$ Calc.: % C, 62.3; % H, 7.19; % N, 12.3 Found: % C, 62.5; % H, 7.24; % N, 12.6

$^1$H NMR $CDCl_3$: 7.4 (d, 1H, J=5.2); 6.8 (d, 1H, J=5.1); 3.8 (br, 2H); 2.87 (m, 1H); 1.2 (d, 6H, J=6.8).

46. Preparation of t-butyl N-(4-Ethyl-2-fluoro-3-pyridyl) carbamate

A solution of lithium diisopropylamine (LDA) was prepared from 19.3 mL (137 mmol) of diisopropylamine and 55 mL (137 mmol) of 2.5M n-butyllithium in hexane in 250 mL of dry tetrahydrofuran at –20° C. A solution of 14.4 g (62.5 mmol) of 1-butyl N-(4-methyl-2-fluoro-3-pyridyl) carbamate in 80 mL of dry tetrahydrofuran was added dropwise with stirring at a rate slow enough to maintain the temperature below –60° C. After a 30-min reaction period, 27 g (190 mmol) of methyl iodide was added and the solution was allowed to warm to –10° C. The resulting mixture was diluted with 100 mL of aqueous ammonium chloride and 200 mL of ether and the phases were separated. The aqueous phase was washed with ether (3×100 mL). The organic phase and washes were combined, dried over magnesium sulfate, and filtered. The filtrate was concentrated by evaporation under reduced pressure to obtain a gold oil. This oil was purified by column chromatography to obtain 11.4 g (76 percent of theory) of the title compound as a white solid melting at 84°–86° C.

$^1$H NMR $CDCl_3$: 7.7 (d, 1H, J=5.08); 6.8 (d, 1H, J=5.08); 6.1 (br, 1H); 2.45 (q, 2H, J=7.6); 1.2 (s, 9H); 1.0 (t, 3H, J=7.6).

t-Butyl N-(4-(1-methylethyl)-2-fluoro-3-pyridyl) carbamate was prepared analogously from t-butyl N-(4-ethyl-2-fluoro-3-pyridyl)carbamate. This compound was obtained in 69 percent yield as a colorless solid melting at 60°–62° C.

Elemental Analysis $C_{13}H_{19}FN_2O_2$ Calc.: % C, 61.4; % H, 7.53; % N, 11.0 Found: % C, 61.6; % H, 7.78; % N, 11.3

$^1$H NMR $CDCl_3$: 7.9 (d, 1H, J=5.4); 7.0 (d, 1H, J=5.4); 6.0 (br, 1H); 3.2 (m, 1H); 1.4 (s, 9H); 1.2 (d, 6H, J=5.2).

47. Preparation of 3-Amino-2,4,5-trichloropyridine

Thirty percent aqueous hydrogen peroxide (3.0 g, 26 mmol) was added dropwise with stirring at 15° C. to a solution of 8.0 g (49 mmol) of 3-amino-4,5-dichloropyridine in 450 mL of 37 percent aqueous hydrochloric acid. After 30 min another 2.6 g (23 mmol) of 30 percent aqueous hydrogen peroxide was added and the solution was allowed to slowly warm to room temperature. The resulting mixture was diluted with water, neutralized with sodium carbonate, and extracted with ether. The ethereal extract was dried over magnesium sulfate and filtered. The filtrate was concentrated by evaporation under reduced pressure to obtain a viscous oil. This oil was partially purified by chromatography to obtain 2.5 g (26 percent of theory) of the title compound, a white solid melting at 88°–90° C., and 5.3 g of a mixture of the title compound and 3-amino-2,4,5,6-tetrachloropyridine.

Elemental Analysis $C_5H_3Cl_3N_2$ Calc.: % C, 30.4; % H, 1.53; % N, 14.2 Found: % C, 30.5; % H, 1.47; % N, 14.1

$^1$H NMR $CDCl_3$: 7.7 (s, 1H); 4.6 (br, 2H).

48. Preparation of 3-Amino-4-fluoro-2-methoxypyridine

A solution 5.0 g (26.2 mmol) of p-toluenesulfonic acid monohydrate in 150 mL of toluene was refluxed to azeotropically remove the water and was then allowed to cool. A 5.0 g (20.6 mmol) amount of t-butyl N-(4-fluoro-2-methoxy-3-pyridyl)carbamate was added and the solution was heated to reflux with stirring for 5 min. The mixture was cooled and the liquid was removed by decantation. The solid residue was partitioned between ether and saturated aqueous sodium carbonate and the organic phase was recovered, dried over magnesium sulfate, filtered, and concentrated by evaporation. The residue was purified by flash chromatography to obtain 2.7 g (91 percent of theory) of the title compound as a near-clear oil.

Elemental Analysis $C_6H_7FN_2O$ Calc.: % C, 50.7; % H, 4.96; % N, 19.7 Found: % C, 50.9; % H, 5.26; % N, 19.1

$^1$HNMR $(CDCl_3)$: 7.5 (dd, 1H, j=5.7, 7.8); 6.6 (dd, 1H, j=5.7, 9.4); 3.9 (s, 3H); 3.7 (br, 2H).

49. Preparation of t-Butyl N-(4-Fluoro-2-methoxy-3-pyridinyl)carbamate

To a solution of 8 g (35.7 mmol) of t-butyl N-(2-methoxy-3-pyridyl)carbamate in 200 mL of dry tetrahydrofuran was added with stirring at –60° C., 46.2 mL (78.5 mmol) of 1.7M t-butyl lithium in pentane. The resulting solution was allowed to warm slowly with stirring to –20° C. over a 20 to 30 min period. It was then cooled to about –60° C. and 12.2 g (38.7 mmol) of N-fluorodibenzenesulfonimide was added with stirring all at once. The mixture was allowed to warm to –20° C. and was poured into 500 mL of ether. The resulting ethereal solution was washed with a mixture of 2.5 g (41.7 mmol) of acetic acid and 150 mL of water. The aqueous phase was extracted with 200 mL of ether. The ethereal extracts were combined, dried over magnesium sulfate, filtered, and concentrated by evaporation. The residue was purified by flash chromatography to obtain 6.7 g (77 percent of theory) of the title compound as a colorless solid melting at 75°–77° C.

Elemental Analysis $C_{11}H_{15}FN_2O_3$ Calc.: % C, 54.5; % H, 6.24; % N, 11.6 Found: % C, 54.2; % H, 6.39; % N, 11.4

$^1$H NMR $(CDCl_3)$: 7.88 (dd, 1H, j=5.8, 7.6); 6.68 (dd, 1H, j=5.8, 8.9); 5.9 (br, 1H); 3.9 (s, 3H); 1.45 (s, 9H).

50. Preparation of Methyl 3-Amino-2-ethoxyisonicotinate

A solution 7.5 g (39.4 mmol) of p-toluenesulfonic acid monohydrate in 150 mL of toluene was refluxed to azeotropically remove the water. The mixture was allowed to cool and then 11.0 g (37.1 mmol) of t-butyl N-(4-carboxymethyl-2-ethoxy-3-pyridyl)carbamate was added with stirring and the solution was heated to 95° C. for 15 min. The resulting mixture was cooled and the liquid was removed by decantation. The solid residue was partitioned between ether and saturated aqueous sodium carbonate. The organic phase was recovered, dried over magnesium sulfate, filtered, and concentrated by evaporation. The residue was purified by column chromatography to obtain 6.4 g (88 percent of theory) of the title compound as a light yellow solid melting at 59°–60.5° C.

Elemental Analysis $C_9H_{12}N_2O_3$ Calc.: % C, 55.1; % H, 6.16; % N, 14.3 Found: % C, 54.6; % H, 6.00; % N, 14.5

¹H NMR (CDCl₃): 7.3 (d, 1H, j=5.6); 7.1 (d, 1H, j=5.6); 5.9 (br, 2H); 4.3 (q, 2H, j=7.1); 3.8 (s, 3H); 1.37 (t, 3H, j=7.1).

Methyl 3-amino-2-methoxyisonicotinate, an amber oil, was prepared analogously.

Elemental Analysis C₈H₁₀N₂O₃ Calc.: % C, 50.0; % H, 4.80; % N, 16.7 Found: % C, 50.2; % H, 5.26; % N, 16.6

¹H NMR (CDCl₃): 7.3 (d, 1H, j=5.6); 7.1 (d, 1H, j=5.6); 5.9 (br, 2H); 3.96 (s, 3H); 3.8 (s, 3H).

Ethyl 3-amino-2-methoxyisonicotinate, a light yellow oil, was prepared analogously.

Elemental Analysis C₉H₁₂N₂O Calc.: % C, 55.1; % H, 6.16; % N, 14.3 Found: % C, 54.2; % H, 6,56; % N, 14.6

¹H NMR (CDCl₃): 7.3 (d, 1H, j=5.6); 7.1 (d, 1H, j=5.6); 5.9 (br, 2H); 4.28 (q, 2H, j=7.2); 3.9 (s, 3H); 1.33 (t, 3H, j=7.14).

51. Preparation of t-Butyl N-(4-Carboxymethyl-2-ethoxy-3-pyridinyl)carbamate To a solution of ! 2.0 g (50.3 mmol) of t-butyl N-(2-ethoxy-3-pyridinyl)carbamate in 200 mL of dry tetrahydrofuran was added with stirring at −50° C., 66 mL (111 mmol) of 1.7M t-butyl lithium in pentane. The resulting solution was allowed to warm slowly to 0° C. over a 20 to 30 min. period and was then cooled to −60° C. and poured into 500 mL of ether saturated with crushed dry ice (carbon dioxide). The resulting mixture was acidified at room temperature with 3.0 g (50 mmol) of acetic acid and the fine white solid precipitate that formed was collected by filtration and dried under reduced pressure at 50° C. to obtain 17.0 g of a lithium salt containing some tetrahydrofuran. This salt was combined with 30.0 g (211 mmol) of iodomethane in 150 mL of dry dimethyl sulfoxide and the mixture was stirred for 1 hr. It was then poured into 400 mL of water. The aqueous mixture was extracted with 500 then 200 mL of ether. The ether extracts were combined, dried over magnesium sulfate, filtered, and concentrated by evaporation. The residue was purified by column chromatography to obtain 11.5 g (77 percent of theory) of the title compound as a colorless solid melting at 94°–95.5° C.

Elemental Analysis C₁₄H₂₀N₂O₅ Calc.: % C, 56.8; % H, 6.80; % N, 9.45 Found: % C, 56.8; % H, 7.00; % N, 9.63

¹H NMR (CDCl₃): 7.8 (d, 1H, j=5.3); 7.1 (d, 1H, j=5.3); 6.9 (br, 1H); 4.4 (q, 2H, j=7.0); 3.8 (s, 3H); 1.46 (s, 9H); 1.37 (t, 3H, j=7.0).

t-Butyl N-(4-carboxyethyl-2-methoxy-3-pyridinyl) carbamate, a colorless solid melting at 40°–41° C., was prepared analogously.

Elemental Analysis C₁₄H₂₀N₂O₅ Calc.: % C, 56.8; % H, 6.80; % N, 9.45 Found: % C, 56.6; % H, 6.76; % N, 9.26

¹H NMR (CDCl₃): 7.9 (d, 1H, j=5.3); 7.1 (d, 1H, j=5.25); 6.9 (br, 1H); 4.27 (q, 2H, j=7.15); 3.96 (s, 3H); 1.45 (s, 9H); 1.33 (t, 3H, j=7.14).

t-Butyl N-(4-Carboxymethyl-2-methoxy-3-pyridinyl) carbamate, a colorless solid melting at 107°–108° C., was obtained analogously.

Elemental Analysis C₁₃H₁₈N₂O₅ Calc.: % C, 55.3; % H, 6.43; % N, 9.92 Found: % C, 55.5; % H, 6.22; % N, 10.1

¹H NMR (CDCl₃): 7.9 (d, 1H, j=5.3); 7.1 (d, 1H, j=5.4); 6.9 (br, 1H); 3.97 (s, 3H); 1.46 (s, 9H).

52. Preparation of t-Butyl N-(4-Chloro-2-ethoxy-3-pyridinyl)carbamate

To a solution of 15 g (63 mmol) of t-butyl N-(2-ethoxy-3-pyridinyl)carbamate in 175 mL of dry tetrahydrofuran was added with stirring at −60° C., 78 mL (132 mmol) of 1.7M t-butyl lithium in pentane. The resulting solution was allowed to warm to −10° C. over a 30 min. period and was then cooled to −60° C. A A 22.3 g (94 mmol) amount of hexachoroethane was added all at once with stirring and the mixture are allowed to warm to ambient temperature. It was then diluted with 600 mL of ether and the resulting solution was washed with 150 mL of water, dried over magnesium sulfate, filtered, and concentrated by evaporation. The residue was purified by column chromatography to obtain 11.1 g (65 percent of theory) of the title compound as a colorless solid melting at 73°–74° C.

Elemental Analysis C₁₂H₁₇ClN₂O₃: Calc.: % C, 52.9; % H, 6.28; % N, 10.3 Found: % C, 53.0; % H, 6.30; % N, 10.3

¹H NMR (CDCl₃): 7.88 (d, 1H, j=5.5); 6.93 (d, 1H, j=5.5); 6.0 (br, 1H); 4.4 (q, 2H, j=7.0); 1.5 (s, 9H); 1.39 (t, 3H, j=7.0.).

53. Preparation of t-Butyl N-(2-Ethoxy-3-pyridinyl) carbamate

To a solution of 38.1 g (0.28 mol) of 3-amino-2-ethoxypyridine in 400 mL of dry dioxane was added with stirring 60 g (0.28 mol) of di-t-butyl dicarbonate and the solution was slowly heated to reflux over a 4 hr period. The resulting solution was cooled below reflux and another 5.0 g (23 mmol) of di-t-butyl dicarbonate was added with stirring the the mixture was reheat at reflux for 1 hr. The volatiles were removed by evaporation under reduced pressure and the residue obtained was purified by column chromatography to obtain 58.3 g (89 percent of theory) of the title compound as a colorless oil.

Elemental Analysis C₁₂H₁₈N₂O₃ Calc.: % C, 60.5; % H, 7.61; % N, 11.8 Found: % C, 59.7; % H, 9.03; % N, 11.9

¹H NMR (CDCl₃): 8.2 (broad d, 1H, j=7.0); 7.7 (d, 1H, j=5.0); 6.9 (br, 1H); 6.8 (dd, 1H, j=5.0, 5.0), 4.4 (q, 2H, j=7.1); 1.47 (s, 9H); 1.36 (t, 3H, j=7.1).

54. Preparation of 3-Amino-4-ethoxy-2-fluoropyridine

To a solution of 19 g (74 mmol) of t-butyl N-(4-ethoxy-2-fluoro-3-pyridinyl)carbamate and 12.2 g (81.5 mmol) of sodium iodide in 400 mL of dry acetonitrile was added with stirring 8.9 g (81.5 mmol) of trimethylsilyl chloride. The mixture was allowed to react for 4 hr and then a 100 mL solution of aqueous sodium bicarbonate was added with stirring. The resulting mixture was extracted with 1 L of ether and the ether extract was dried over magnesium sulfate, filtered, and concentrated by evaporation. The residue was purified by column chromatography to obtain 6.3 g (55 percent of theory) of the title compound as a colorless solid melting at 76°–77° C.

Elemental Analysis C₇H₉FN₂O Calc.: % C, 53.5; % H, 5.81; % N, 17.9 Found: % C, 54.3; % H, 6.44; % N, 17.7

¹H NMR (CDCl₃): 7.5 (d, 1H, j=5.74); 6.5 (d, 1H, j=5.64); 4.1 (q, 2H, j=7.0); 3.6 (br, 2H); 1.4 (t, 3H, j=6.9).

3-Amino-2-fluoro-4-methoxypyridine, a colorless solid melting at 48°–50° C., was prepared analogously.

Elemental Analysis C₆H₇FN₂O Calc.: % C, 50.7; % H, 4.96; % N, 19.7 Found: % C, 50.9; % H, 5.13; % N, 19.9

¹H NMR (CDCl₃): 7.5 (d, 1H, j=5.57); 6.63 (d, 1H, j=5.47); 3.8 (s, 3H); 3.7 (br, 2H).

3-Amino-2-fluoro-4-propoxypyridine, a colorless oil, was prepared analogously.

Elemental Analysis C₈H₁₁FN₂O Calc.: % C, 55.5; % H, 6.51; % N, 16.5 Found: % C, 56.7; % H, 6.66; % N, 16.2

¹H NMR (CDCl₃): 7.4 (d, 1H, j=5.61); 6.5 (d, 1H, j=5.71); 4.5 (t, 2H, j=6.5); 3.7 (br, 2H); 1.8 (m, 2H, j=7.3); 1.0 (t, 3H, j=7.4).

3-Amino-2-fluoro-4-(1-methylethoxy)pyridine, a gold oil, was prepared analogously.

Elemental Analysis C₈H₁₁FN₂O Calc.: % C, 55.5; % H, 6.51; % N, 16.5 Found: % C, 56.9; % H, 6.69; % N, 16.4

¹H NMR (CDCl₃): 7.5 (d, 1H, j=5.57); 6.6 (d, 1H, j=5.71); 4.5 (m, 1H, j=6.0); 3.6 (br, 2H); 6.6 (d, 6H, j=6.1).

55. Preparation of t-Butyl N-(4-ethoxy-2-fluoro-3-pyridinyl)carbamate

To a solution of 18.5 g (131 mmol) of 4-ethoxy-2-fluoropyridine in 300 mL of dry tetrahydrofuran at −78° C. was added slowly, with stirring and cooling to maintain the temperature below −65° C., 58 mL of 2.5M butyl lithium in hexane. The mixture was allowed to react for 1 hr and then the resulting slurry was poured into 1300 mL of ether containing excess powdered dry ice (carbon dioxide). The fine white precipitate that formed was collected by filtration and dried under reduced pressure for 90 min. The hygroscopic solid obtained was taken into 700 mL of t-butanol and 68 g (0.24 mol) of diphenyl phosphoryl azide was added with stirring. This mixture was slowly warmed to reflux for 2 hr during which time there was a vigorous evolution of nitrogen. The resulting slurry was filtered and the filtrate was diluted with 800 mL of dichloromethane. The organic phase was separated, washed with water (2×100 mL), and concentrated by evaporation to obtain a semi-solid residue. This was dissolved in fresh dichloromethane and the solution was dried over magnesium sulfate, filtered, and concentrated by evaporation. The residue was purified by column chromatography to obtain 19.5 g (63 percent of theory) of the title compound as a colorless solid melting at 130°–131° C.

Elemental Analysis $C_{12}H_{17}FN_2O_3$ Calc.: % C, 56.2; % H, 6.69; % N, 10.9 Found: % C, 56.1; % H, 6.99; % N, 11.3

$^1$H NMR (CDCl$_3$): 7.85 (d, 1H, j=5.7); 6.6 (d, 1H, j=5.7); 6.0 (br, 1H); 4.1 (q, 2H, j=7.0); 1.4 (t, 3H, j=6.9); 1.35 (t, 3H, j=7.0).

t-Butyl N-(2-fluoro-4-(1-methylethoxy)-3-pyridinyl) carbamate, a colorless solid melting at 80°–81.5° C., was obtained analogously.

Elemental Analysis $C_{13}H_{19}FN_2O_3$ Calc.: % C, 57.8; % H, 7.09; % N, 10.4 Found: % C, 57.9; % H, 6.94; % N, 10.7

$^1$H NMR (CDCl$_3$): 7.9 (d, 1H, j=5.9); 6.7 (d, 1H, j=5.96); 6.0 (br, 1H); 4.6 (m, 1H, j=6.1); 1.45 (s, 9H); 1.35 (d, 6H, j=6.1).

t-Butyl N-(2-fluoro-4-propoxy-3-pyridinyl)carbamate, a colorless solid melting at 84°–86° C., was obtained analogously.

Elemental Analysis $C_{13}H_{19}FN_2O_3$ Calc.: % C, 57.8; % H, 7.09; % N, 10.4 Found: % C, 57.8; % H, 7.37; % N, 10.5

$^1$H NMR (CDCl$_3$): 7.9 (d, 1H, j=5.8); 6.7 (d, 1H, j=5.8); 5.8 (br, 1H); 4.0 (t, 2H, j=6.5); 1.83 (m, 2H, j=7.36); 1.46 (s, 9H); 1.0 (t, 3H, j=7.5).

56. Preparation of 4-Ethoxy-2-fluoropyridine

To a solution of 60.5 g (0.31 mol) of 3,5-dichloro-4-ethoxy-2-fluoropyridine and 32.2 g (0.32 mol) of sodium acetate in 400 mL of ethanol in a 1 L stirred steel Parr bomb was added 3 g of 5 percent palladium on carbon catalyst. The reactor was charged with 500 pounds per square inch gauge (3550 kiloPascals) of hydrogen and heated with stirring to 100° C. for 4 hr. The mixture was cooled, filtered, and concentrated by evaporation. The residue was dissolved in ether and the resulting solution was dried over magnesium sulfate, filtered, and concentrated by evaporation. The residue was purified by bulb to bulb distillation (60°–80° C. at 0.5 mm Hg (67 Pascals) to obtain 18.5 g (42 percent of theory) of the title compound as a colorless oil which solidified upon standing and melted at 35°–36° C.

Elemental Analysis $C_7H_8NO$ Calc.: % C, 59.6; % H, 5.71; % N, 9.92 Found: % C, 59.2; % H, 5.97; % N, 9.95

$^1$H NMR (CDCl$_3$): 7.9 (d, 1H, j=5.8); 6.6 (m, 1H); 6.3 (d, 1H, j=2.2); 4.0 (q, 2H, j=7.0); 1.4 (t, 3H, j=7.0).

2-Fluoro-4-methoxypyridine, a colorless oil boiling at 119°–122° C. at 30 mm Hg (4.0 kiloPascals), was prepared analogously.

Elemental Analysis $C_6H_6FNO$ Calc.: % C, 59.6; % H, 5.71; % N, 9.92 Found: % C, 59.2; % H, 5.97; % N, 9.95

$^1$H NMR (CDCl$_3$): 8.0 (d, 1H, j=5.9); 6.7 (m, 1H); 6.4 (d, 1H, j=2.1); 3.9 (s, 3H).

2-Fluoro-4-(1-methylethoxy)pyridine, a colorless oil, was obtained analogously.

Elemental Analysis $C_8H_{10}FNO$ Calc.: % C, 61.9; % H, 6.50; % N, 9.03 Found: % C, 61.5; % H, 6.59; % N, 9.32

$^1$H NMR (CDCl$_3$): 8.0 (d, 1H, j=5.9); 6.6 (dd, 1H, j=4.5, 1.4); 6.33 (d, 1H, j=2.0); 4.0 (t, 2H, j=6.6); 1.8 (m, 2H, j=7.3); 1.0 (t, 3H, j=7.3).

2-Fluoro-4-propoxypyridine, a colorless oil, was obtained analogously.

Elemental Analysis $C_8H_{10}FNO$ Calc.: % C, 61.9; % H, 6.50; % N, 9.03 Found: % C, 61.0; % H, 7.50; % N, 9.09

$^1$H NMR (CDCl$_3$): 8.0 (d, 1H, j=5.9); 6.6 (m, 1H); 6.3 (d, 1H, j=2.2); 4.57 (m, 1H, j=6.1); 1.3 (d, 6H, j=6.1).

57. Preparation of 3,5-Dichloro-4-ethoxy-2-fluoropyridine

To a solution of 70.2 g (0.38 mol) of 3,5-dichloro-2,4-difluoropyridine in 600 mL of ethanol was slowly added with stirring a solution of sodium ethoxide in ethanol prepared from 16 g (0.40 mol) of sodium hydride (60 percent in mineral oil, hexane washed) in 200 mL of ethanol. The mixture was allowed to stir overnight and the brown solution obtained was filtered through powdered cellulose and concentrated by evaporation under reduced pressure. The residue was partitioned between 500 mL of ether and 400 mL of water. The organic phase was recovered, dried over magnesium sulfate, filtered, and concentrated by evaporation. The residue was distilled to obtain 62 g (84 percent of theory) of the title compound as a colorless oil having a boiling point of 175°–180° C. at 0.4 mm Hg (53 Pascals).

Elemental Analysis $C_7H_6Cl_2FN$ Calc.: % C, 43.3; % H, 3.12; % N, 7.22 Found: % C, 40.0; % H, 2.92; % N, 6.66

$^1$H NMR (CDCl$_3$): 8.04 (s, 1H); 4.3 (q, 2H, j=7.0); 1.48 (t, 3H, j=7.1).

3,5-Dichloro-2-fluoro-4-methoxypyridine, a colorless oil, was obtained analogously.

$^1$H NMR (CDCl$_3$): 8.1 (s, 1H); 4.88 (m, 1H, j=6.1); 1.4 (d, 6H, j=6.1).

1,5-Dichloro-2-fluoro-4-(1-methylethoxy)pyridine, a colorless oil, was obtained analogously.

$^1$H NMR (CDCl$_3$): 8.0 (s, 1H); 4.88 (m, 1H, j=6.1); 1.4 (d, 6H, j=6.1).

3,5-Dichloro-2-fluoro-4-propoxypyridine, a colorless oil, was obtained analogously.

$^1$H NMR (CDCl$_3$): 8.1 (s, 1H); 4.2 (t, 2H, j=6.7); 1.86 (m, 2H, j=7.1); 1.1 (t, 3H, j=7.3).

58. Preparation of 3-Amino-4-fluoro-1-methylindazole

Methylhydrazine (4.96 g, 108 mmol was added to a solution of 15.0 g (108 mmol) of 2,6-difluorobenzonitrile in 150 mL of ethanol and the mixture was heated to reflux with stirring for 72 hours. The volatiles were when removed by evaporation under reduced pressure and the residue was dissolved in dichloromethane. The resulting solution was washed with water, dried over magnesium sulfate, and evaporated to dryness under reduced pressure to obtain the title compound as a white solid. This was recrystallized from ethanol to obtain 10.1 g (57 percent of theory) of the title compound as white crystals melting at 125°–127° C.

Elemental Analysis $C_8H_8FN_3$ Calc.: % C, 58.2; % H, 4.88; % N, 25.4 Found: % C, 58.7; % H, 4.76; % N, 25.9

$^1$H NMR CDC$_3$: 7.19 (m, 1H), 7.11 (d, 1H, J=8.4), 6.59 (d of d, 1H, J=8.4, 3.3), 5.26 (brs, 2H), 3.72 (s, 3H); $^{13}$C NMR CDCl$_3$: 157.35, 154.88, 146.20, 146.18, 143.85, 143.76, 127.62, 127.55, 105.31, 105.27, 103.44, 103.24, 101.96, 101.78, 34.74.

59. Preparation of 3-Amino-1-methyl-4-(trifluoromethylthio)pyrazole

Trifluoromethanesulfenyl chloride (11.6 g, 85.0 mmol) was added to a solution of 3-amino-1-methylpyrazole (8.0 g, 82.4 mmol) in 150 mL of dichloromethane with stirring at a rate such that the temperature did not rise above 5° C. when the addition was complete the mixture was allowed to warm to ambient temperature and stir for 18 hours and was then purged with nitrogen gas for 1 hour to remove any unreacted trifluoromethanesulfenyl chloride. The solid that formed during the reaction was collected by filtration and the filtrate was concentrated by evaporation under reduced pressure to obtain additional solids. The combined solids were dissolved in water and the solution as basified with 1N aqueous sodium hydroxide. The resulting mixture was extracted with dichloromethane (2×100 mL) and the extracts were combined, dried over magnesium sulfate, and filtered. The filtrate was concentrated by evaporation under reduced pressure to obtain a solid residue that appeared to be a mixture of two compounds. This solid was recrystalized from methylcyclohexane to obtain 16.2 g (40 percent of theory) of the title compound as a yellow solid melting at 138°–140° C. The impurity was identified as 1-methyl-3-((trifluoromethanesulfenyl)amino)-4-(trifluoromethylthio)pyrazole.

Elemental Analysis $C_5H_6F_3N_3S$ Calc.: % C, 30.5; % H, 3.07; % N, 21.3; % S, 16.3 Found: % C, 30.5; % H, 2.87; % N, 21.1; % S, 16.5

$^1$H (CDCl$_3$): 7.31 (s, 1H), 4.00 (brs, 2H), 3.68 (s, 3H);

$^{13}$C (CDCl$_3$): 157.47, 137.04, 133.61, 130.52, 127.44, 124.35, 84.23, 38.97.

60. Preparation of Methyl 6-Chloro-3-methoxypicolinate and Methyl 3-Chloro-6-methoxypicolinate Sodium methoxide in methanol (100 mL of 25 percent, 22.8 g, 0.42 mol) was added to a solution of methyl 3,6-dichloropicolinate (44.0 g, 0.21 mol) in acetonitrile (400 mL) and the resulting solution was stirred at room temperature for 3.5 hours. The reaction mixture was acidified with acetic acid and the solvent was removed by evaporation. The residue obtained was mixed with dichloromethane and washed sequentially with water, dilute aqueous sodium hydroxide, and dilute aqueous hydrochloric acid. The organic solvent was removed by evaporation and the residue obtained was purified by column chromatography on silica gel, eluting with 20 percent ethyl acetate in hexane until the methyl 3-chloro-6-methoxypicolinate desorbed and then with 25 percent ethyl acetate in hexane until the methyl 6-chloro-3-methoxypicolinate desorbed. Methyl 3-chloro-6-methoxypicolinate (23.4 g) was recovered as a white powder melting at 38°–39° C. and the methyl 6-chloro-3-methoxypicolinate (8.5 g) was recovered as a white powder melting at 81°–82° C.

61. Preparation of 6-Chloro-3-methoxypicolinamide

Methyl 6-chloro-3-methoxypicotinate (8.0 g, 40 mmol) was added to a mixture of dichloromethane (50 mL) and concentrated ammonium hydroxide (100 mL) at room temperature and the combination was allowed to stir overnight. The resulting mixture was filtered and the organic and aqueous layers were separated. The organic layer was concentrated by evaporation and the solid residue obtained was washed with water and a little ether and then dried to obtain 6.7 g of the title compound as a white powder melting at 223°–224° C.

62. Preparation of 2-Amino-6-chloro-3-methoxypyridine

Sodium hydroxide (6.1 g, 196 mmol) was dissolved in water (75 mL) and cooled in an ice bath. Chlorine (3.8 g, 53 mmol) was added slowly with stirring keeping the temperature below 5° C. 6-Chloro-3-methoxypicolinamide (16.1 g, 23 mmol) was added to this solution and the mixture was stirred at 0° C. for 4 hours (until the solids had dissolved). The reaction mixture was acidified with acetic acid and extracted with dichloromethane. The organic extract was concentrated by evaporation and the residue obtained was diluted with hexane. The resulting slurry was filtered and the solids collected were dried to obtain 4.1 g of the title compound as a tan powder melting at 134°–135° C.

Elemental Analysis for $C_6H_7ClN_2O$ Calc.: % C, 45.4; % H, 4.45; % N, 17.7 Found: % C, 45.2; % H, 4.58; % N, 17.4

63. Preparation of N-(6-Chloro-3-methoxy-2-pyridinyl)-N'-carboethoxythiourea Ethoxycarbonyl isothiocyanate (3.7 mL, 4.1 g, 31.5 mmol) was added slowly with stirring to a solution of 2-amino-6-chloro-3-methoxypyridine (5.0 g, 31.5 mmol) in chloroform (40 mL) and the mixture was stirred overnight. The solvent was removed by evaporation and the residue obtained was mixed with hexane. The resulting slurry was filtered and the solids collected were washed with a small amount of ether and dried to obtain 8.3 g of the title compound as a man powder melting at 184°–185° C. with decomposition.

The following compounds were prepared by analogous procedures from known 2-aminopyridine compounds:

N-2-Pyridinyl-N'-carboethoxythiourea (a yellow powder melting at 94°–96° C.).

N-(6-Chloro-2-pyridinyl)-N'-carboethoxythiourea (a pale yellow powder melting at 73°–74° C.).

N-(3-Methoxy-2-pyridinyl)-N'-carboethoxythiourea (a pale yellow powder melting at 147°–148° C.).

N-(3,6-Dichloro-2-pyridinyl)-N'-carboethoxy thiourea (a yellow powder melting at 159°–161° C.).

Elemental Analysis $C_9H_9Cl_2N_3O_2S$ Calc.: % C, 36.8; % H, 3.08; % N, 14.3; % S, 10.9 Found: % C, 36.9; % H, 2.88; % N, 14.4; % S, 10.7

N-(3,5-Dichloro-2-pyridinyl)-N'-carboethoxythiourea (a yellow powder).

Elemental Analysis $C_9H_9Cl_2N_3O_2S$ Calc.: % C, 36.8; % H, 3.08; % H, 14.3; % S, 10.9 Found: % C 36.5, % H, 3.36; % N, 14,4; % S, 11.1

N-(3-Fluoro-5-trifluoromethyl-2-pyridinyl)-N'-carboethoxythiourea. (a white powder melting at 86°–90° C.).

Elemental Analysis $C_{10}H_9F_4N_3O_2S$ Calc.: % C, 38.6; % H, 2.91; % N, 13.5; % S, 10.3 Found: % C, 38.5; % H, 2.69; % N, 13.4; % S, 10.2

N-(3-Bromo-5-methyl-2-pyridinyl)-N'-carboethoxythiourea (a yellow powder melting at 148°–150° C.).

Elemental Analysis $C_{10}H_{12}BrN_3O_2S$ Calc.: % C, 37.8; % H, 3.80; % N, 13.2; % S, 10.1 Found: % C, 37.8; % H, 3.72; % N, 13.1; % S, 10.1

64. Preparation of 2-Amino-5-chloro-8-methoxy[1,2,4]triazolo[1,5-a]pyridine

Hydroxylamine hydrochloride (9.6 g, 138 mmol) and diisopropylethylamine (14.4 mL, 10.7 g, 83 mmol) were mixed with ethanol (300 mL) for a few minutes and then N-(6-chloro-3-methoxy-2-pyridinyl)-N'-carboethoxythiourea (7.6 g, 27.5 mmol) was added with stirring. The resulting mixture was stirred at room temperature for 20 min and then heated to reflux for 3 hours. The volatile components were removed by evaporation and the residue obtained was mixed with water. The resulting slurry was filtered and the solids collected were washed with ether, a small amount of methanol, and finally hexane and were then dried. The title compound (3.2 g) was obtained as a tan powder melting at 207°–208° C.

Elemental Analysis $C_7H_7ClN_4O$ Calc.: % C, 42.3; % H, 3.55; % N, 28.2 Found: % C, 41.7, % H, 2.91; % N, 27.9

The following compounds were prepared by analogous procedures from the products of Example 63:

2-Amino[1,2,4]triazolo[1,5-a]pyridine (a yellow powder melting at 100°–102° C.).

2-Amino-5-chloro[1,2,4]triazolo[1,5-a]pyridine (an off-white powder melting at 212°–213° C.).

Elemental Analysis $C_6H_5ClN_4$ Calc.: % C, 42.7; % H, 2.99; % N, 33.2 Found: % C, 42.7; % H, 3.01; % N, 33.6

2-Amino-8-methoxy[1,2,4]triazolo[1,5-a]pyridine (a light tan powder melting at 204°–206° C.).

Elemental Analysis $C_6H_8N_4O$ Calc.: % C, 51.2; % H, 4.91; % N, 34.1 Found: % C, 51.3; % H, 6.09; % N, 33.8

2-Amino-5,8-dichloro[1,2,4]triazolo[1,5-a]pyridine (a white powder melting at 236°–238° C.).

Elemental Analysis $C_6H_4Cl_2N_4$ Calc.: % C, 35.5; % H, 1.99; % N, 27.6 Found: % C, 35.6; % H, 2.12; % N, 27.4

2-Amino-6,8-dichloro[1,2,4]triazolo[1,5-a]pyridine (a white powder melting above 280° C.).

Elemental Analysis $C_6H_4Cl_2N_4$ Calc.: % C, 35.5; % H, 1.99; % N, 27.6 Found: % C, 35.8; % H, 1.96; % N, 27.3

2-Amino-8-fluoro-6-trifluoromethyl[1,2,4]triazolo[1,5-a]pyridine (an off-white powder melting at 221°–224° C.).

Elemental Analysis $C_7H_4F_4N_4$ Calc.: % C, 38.2; % H, 1.83; % N, 25.5 Found: % C, 38.1; % H, 2.04; % N, 24.1

2-Amino-8-bromo-6-methyl[1,2,4]triazolo[1,5-a]pyridine (a white powder melting above 280° C.).

Elemental Analysis $C_7H_7BrN_4$ Calc.: % C, 37.0; % H, 3.11; % N, 24.7 Found: % C, 37.0; % H, 3.14; % N, 24.7

65. Preparation of 2-Benzylthio-5-chloro-8-methoxy[1,2,4]triazolo[1,5-a]pyridine t-Butyl nitrite (6.7 mL, 5.2 g, 50 mmol) was added all at once to a mixture of 2-amino-5-chloro-8-methoxy[1,2,4]triazolo[1,5-a]pyridine (5.0 g, 25 mmol) and dibenzyl disulfide (18.6 g, 75 mmol) in acetonitrile (250 mL) at 35° C. with stirring. The reaction was exothermic, but a mantle was placed under the reaction flask to heat it to reflux rapidly. The evolution of gas began immediately and stopped after about 15 minutes. The volatiles were removed by evaporation and the residue was purified by column chromatography on silica gel eluting with 30 percent ethyl acetate in hexane. The dibenzyl disulfide eluted first followed by the title compound. The solvent was removed by evaporation and the residue was mixed with hexane and filtered. The collected solids were dried to obtain 6.1 g of the title compound as a light tan powder melting at 99°–100° C.

Elemental Analysis $C_{14}H_{12}ClN_3OS$ Calc.: % C, 55.0; % H, 3.96; % N, 13.7; % S, 10.5 Found: % C, 54.9; % H, 4.08; % N, 13.9; % S, 10.5

2-Benzylthio-5-chloro[1,2,4]triazolo[1,5-a]pyridine (a pale yellow powder melting at 65°–66° C.) was prepared by an analogous procedure.

Elemental Analysis $C_{13}H_{10}ClN_3S$ Calc.: % C, 56.6; % H, 3.66; % N, 15.2; % S, 11.6 Found: % C, 56.7; % H, 3.56; % N, 15.4; % S, 11.5

66. Preparation of 2-Chlorosulfonyl-5-chloro-8-methoxy[1,2,4]triazolo[1,5-a]pyridine Chlorine (6.7 g, 96 mmol) was added slowly with stirring at 3°–7° C. to a mixture of 2-benzylthio-5-chloro-8-methoxy[1,2,4]triazolo[1,5-a]pyridine (6.5 g, 21 mmol) in dichloromethane (75 mL) and water (75 mL) and the reaction mixture was stirred for a 30 min period after the chlorine had been added. The layers were separated and the organic layer was dried over a mixture of magnesium and sodium sulfates and concentrated by evaporation under reduced pressure. The residue obtained was triturated with hexane, filtered, and dried to obtain 5.2 g of the title compound as a light tan powder melting at 149°–151° C.

67. Preparation of N-(2,6-Difluorophenyl)-5-chloro-8-methoxy[1,2,4]triazolo[1,5-a]pyridine-2-sulfonamide Dimethyl sulfoxide (90 microliters, 94 micrograms, 1.2 mmol) was added with stirring to a solution of 2-chlorosulfonyl-5-chloro-8-methoxy[1,2,4]triazolo[1,5-a]pyridine (1.7 g, 6 mmol), 2,6-difluoroaniline (1.6 g, 12 mmol) and pyridine (0.5 g, 6 mmol) in acetonitrile (20 mL) at ambient temperature. The reaction was complete in about 20 min. Dichloromethane and water were added and the solid that separated was collected by filtration. The organic layer was concentrated by evaporation and the residue obtained was washed with water and combined with the earlier obtained solid. The combined solids were then washed with ether and hexane and dried to obtain 1.4 g of the title compound as an off-white powder melting at 190°–191° C. (d).

Elemental Analysis $C_{13}H_9ClF_2N_4O_3S$ Calc.: % C, 41.7; % H, 2.42; % N, 15.0; % S, 8.56 Found: % C, 41.3; % H, 2.37; % N, 15.0; % S, 8.69

The following compounds were prepared analogous procedures:

N-(2-Chloro-4-methoxy-3-pyridinyl)-5-chloro-8-methoxy[1,2,4]triazolo[1,5-a]pyridine-2-sulfonamide (a white powder melting at 253°–254° C. (d)).

Elemental Analysis $C_{13}H_{11}Cl_2N_5O_4S$ Calc.: % C, 38.6; % H, 2.74; % N, 17.3; % S, 7.90 Found: % C, 38.8; % H, 2.90; % N, 17.4; % S, 7.47

N-(1-Methyl-4-bromo-3-pyrazoyl)-5-chloro-8-methoxy[1,2,4]triazolo[1,5-a]pyridine-2-sulfonamide (a light tan powder melting at 269°–270° C. (d)).

Elemental Analysis $C_{11}H_{10}BrClN_6O_3S$ Calc.: % C, 31.3; % H, 2.39; % N, 19.9; % S, 7.60 Found: % C, 31.9; % H, 2.39; % N, 19.6; % S, 7.60

68. Preparation of N-(2,6-Difluorophenyl)-5,8-dimethoxy[1,2,4]triazolo[1,5-a]pyridine-2-sulfonamide N-(2,6-Difluorophenyl)-5-chloro-8-methoxy[1,2,4]triazolo[1,5-a]pyridine-2-sulfonamide (1.0 g, 2.7 mmol), sodium methoxide (25 percent in methanol, 2.5 mL, 0.58 g, 11 mmol) and dimethyl sulfoxide (20 mL) were mixed with stirring and slowly heated to 70° C. over a 40-min period. After a short reaction period, the reaction mixture was acidified with acetic acid and diluted with dichloromethane and water. The solid that separated was recovered by filtration. The organic layer was separated, was washed several times with water, and was concentrated by evaporation under reduced pressure. The residue obtained was washed with water and combined with the previously obtained solid. The combined solids were washed with ether and hexane and dried to obtain 0.7 g of the title compound as an off-white powder melting at 319°–320° C. (d).

Elemental Analysis $C_{14}H_{12}F_2N_4O_4S$ Calc.: % C, 45.1; % H, 3.27; % N, 15.1; % S, 8.66 Found: % C, 43.4; % H, 3.13; % N, 14.8; % S, 8.23

The following compounds were prepared by analogous procedures from compounds of Example 68:

N-(2-Chloro-4-methoxy-3-pyridinyl)-5,8-dimethoxy[1,2,4]triazolo[1,5-a]pyridine-2-sulfonamide (a light tan powder melting at 257°–258° C. (d)).

Elemental Analysis $C_{14}H_{14}ClN_5O_5S$ Calc.: % C, 42.1; % H, 3.53; % N, 17.7; % S, 8.02 Found: % C, 41.7; % H, 2.85; % N, 17.3; % S, 7.74

N-(1-Methyl-4-bromo-3-pyrazoyl)-5,8-dimethoxy[1,2,4]triazolo[1,5-a]pyridine-2-sulfonamide (a tan powder melting at 257°–258° C. (d)).

Elemental Analysis $C_{12}H_{13}BrN_6O_4S$ Calc.: % C, 34.5; % H, 3.14; % N, 20.1; % S, 7.68 Found: % C, 34.1; % H, 2.98; % N, 19.8; % S, 7.27

69. Evaluation of Postemergence Herbicidal Activity

Seeds of the desired test plant species were planted in Grace-Sierra MetroMix® 206 planting mixture, which typically has a pH of 6.0 to 6.8 and an organic matter content of about 30 percent, in plastic pots with a surface area of 64 square centimeters. When required to ensure good germination and healthy plants, a fungicide treatment and/or other chemical or physical treatment was applied. The plants were grown for 7–21 days in a greenhouse with an approximately 15 hr photoperiod maintained at about 23°–19° C. during the day and 22°–28° C. during the night. Nutrients and water were added on a regular basis and supplemental lighting was provided with overhead metal halide 1000 Watt lamps as necessary. The plants were employed for testing after they reached the first or second true leaf stage.

A weighed amount, determined by the highest rate to be tested, of each test compound was placed in a 20 mL glass vial and was dissolved in 4 mL of a 97:3 (volume/volume) mixture of acetone and dimethyl sulfoxide to obtain concentrated stock solutions. If the test compound did not dissolve readily, the mixture was warmed and/or sonicated. The concentrated stock solutions obtained were diluted with an aqueous mixture containing acetone, water, isopropyl alcohol, dimethyl sulfoxide, Atplus 411F crop oil concentrate, and Triton X-155 surfactant in a 48.5:39:10:1.5:1.0:0.02 v/v ratio to obtain spray solutions of known concentration. The solutions containing the highest concentration to be tested were prepared by diluting 2 mL aliquots of the stock solution with 13 mL of the mixture and lower concentrations were prepared by dilution of appropriate smaller portions of the stock solution. Approximately 1.5 mL aliquots of each solution of known concentration were sprayed evenly onto each of the test plant pots using a DeVilbiss atomizer driven by compressed air pressure of 2 no 4 psi (140 to 280 kiloPascals) to obtain thorough coverage of each plant. Control plants were sprayed in the same manner with the aqueous mixture. In this test an application rate of 1 ppm results in the application of approximately 1 g/Ha.

The treated plants and control plants were placed in a greenhouse as described above and watered by sub-irrigation to prevent wash-off of the test compounds. After 2 weeks the condition of the test plants as compared with that of the untreated plants was determined visually and scored on a scale of 0 to 100 percent where 0 corresponds to no injury and 100 corresponds to complete kill. Some of the compounds tested, application rates employed, plant species tested, and results are given in Tables 2 and 2A.

TABLE 2

POSTEMERGENCE HERBICIDAL ACTIVITY

| Cpd. No. | Rate, ppm | Cockle-bur | Jimson-weed | Lambs-quarters | Morning-glory | Velvet-leaf | Field Pansy | Wild Buck-wheat | Black-grass | Barn-yard grass | Giant fox-tail | Johnson-grass |
|---|---|---|---|---|---|---|---|---|---|---|---|---|
| 1 | 62.5 | 20 | 70 | 70 | 95 | 95 | 30 | 90 | 0 | 0 | 0 | 0 |
| 2 | 62.5 | 95 | 80 | 70 | 95 | 100 | 40 | 90 | 0 | 0 | 0 | 0 |
| 3 | 125 | 85 | 70 | 85 | 80 | 95 | 30 | 80 | 20 | 20 | 0 | 20 |
| 4 | 125 | 100 | 80 | 20 | 70 | 100 | 75 | 75 | 0 | 0 | 0 | 0 |
| 5 | 62.5 | 85 | 50 | 90 | 50 | 95 | 85 | 0 | 0 | 0 | 0 | 0 |
| 6 | 125 | 0 | 0 | 25 | 50 | 85 | 100 | 0 | 25 | 0 | 0 | 0 |
| 7 | 125 | 98 | 70 | 70 | 70 | 80 | 100 | 75 | 70 | 50 | 50 | 70 |
| 8 | 3.9 | 100 | 50 | 85 | 70 | 65 | 60 | 70 | 100 | 80 | 25 | 93 |
| 9 | 31.3 | 90 | 95 | 70 | 90 | 98 | 100 | 85 | 85 | 80 | 70 | 75 |
| 10 | 500 | 80 | 80 | 20 | 40 | 80 | 100 | 40 | 80 | 70 | 0 | 0 |
| 11 | 125 | 80 | 40 | 20 | 80 | 85 | 95 | 50 | 20 | 50 | 35 | 0 |
| 12 | 250 | 90 | 90 | 60 | 80 | 95 | 100 | 70 | 80 | 98 | 60 | 80 |
| 13 | 15.6 | 75 | 70 | 90 | 100 | 98 | 100 | 85 | 80 | 90 | 50 | 90 |
| 14 | 250 | 100 | 100 | 60 | 100 | 80 | 100 | 90 | 80 | 98 | 85 | 70 |
| 15 | 1000 | 80 | 30 | 0 | 40 | 65 | 25 | 0 | 60 | 0 | 0 | 0 |
| 16 | 125 | 35 | 80 | 90 | 100 | 95 | 100 | — | 95 | — | 20 | 50 |
| 17 | 31.3 | 40 | 65 | 65 | 85 | 85 | 100 | 90 | 0 | 35 | 25 | 35 |
| 18 | 62.5 | 95 | 95 | 90 | 75 | 95 | 95 | — | 0 | — | 40 | 10 |
| 19 | 15.6 | 95 | 75 | 80 | 80 | 85 | 80 | 80 | 85 | 90 | 90 | 80 |
| 20 | 3.9 | 100 | 90 | 80 | 80 | 85 | 85 | 80 | 35 | 80 | 50 | 88 |
| 21 | 7.8 | 100 | 90 | 90 | 86 | 85 | 75 | 85 | 85 | 88 | 35 | 85 |
| 22 | 83.3 | 85 | 75 | 50 | 90 | 90 | 50 | 30 | 20 | 35 | 0 | 0 |
| 23 | 15.6 | — | — | 75 | 100 | 85 | 85 | 90 | 80 | 85 | 75 | 90 |
| 24 | 15.6 | 88 | — | 75 | 90 | — | 90 | 90 | 70 | 89 | 70 | 85 |
| 25 | 31.3 | 100 | 100 | 70 | 98 | 98 | 100 | 100 | 90 | 85 | 40 | 70 |
| 26 | 31.3 | 98 | 70 | 40 | 80 | 85 | 100 | 100 | 20 | 30 | 20 | 60 |
| 27 | 31.3 | 90 | 80 | 50 | 60 | 98 | 80 | 100 | 50 | 40 | 20 | 40 |
| 28 | 1.95 | 90 | 85 | 60 | 95 | 75 | 98 | 100 | 55 | 70 | 20 | 75 |
| 29 | 31.3 | 100 | 70 | 80 | 50 | 99 | 100 | 99 | 80 | 80 | 55 | 75 |
| 30 | 15.6 | 98 | 98 | 30 | 100 | 85 | 90 | 85 | 98 | 80 | 30 | 75 |
| 31 | 3.9 | 100 | 88 | 40 | 80 | 90 | 100 | 90 | 0 | 25 | 60 | 50 |
| 32 | 7.8 | 90 | 70 | 78 | 90 | 88 | 100 | 100 | 20 | 80 | 75 | 80 |
| 33 | 31.3 | 98 | 50 | 80 | 100 | 80 | 100 | 80 | 80 | 75 | 50 | 75 |
| 34 | 31.3 | 98 | 70 | 80 | 98 | 100 | 100 | 85 | 70 | 98 | 40 | 98 |
| 35 | 31.3 | 90 | 50 | 70 | 90 | 80 | 100 | 100 | 20 | 40 | 0 | 70 |
| 36 | 31.3 | 90 | 55 | 80 | 100 | 80 | 98 | 99 | 35 | 70 | 40 | 90 |
| 37 | 3.9 | 55 | 60 | 20 | 99 | 97 | 100 | 100 | 35 | 0 | 0 | 0 |
| 38 | 7.8 | 100 | 95 | 15 | 70 | 97 | 100 | 95 | 0 | 0 | 30 | 65 |
| 39 | 15.6 | 97 | 80 | 60 | 70 | 93 | 99 | 70 | 50 | 35 | 50 | 80 |
| 40 | 31.3 | 93 | 80 | 35 | 70 | 93 | 100 | 80 | 80 | 70 | 60 | 75 |
| 41 | 15.6 | 100 | 85 | 0 | 93 | 99 | 90 | 99 | 50 | 30 | 45 | 65 |
| 42 | 15.6 | 100 | 85 | 100 | 90 | 90 | 100 | 85 | 50 | 75 | 75 | 75 |

5,700,940

TABLE 2-continued

POSTEMERGENCE HERBICIDAL ACTIVITY

| Cpd. No. | Rate, ppm | Cockle-bur | Jimson-weed | Lambs-quarters | Morning-glory | Velvet-leaf | Field Pansy | Wild Buck-wheat | Black-grass | Barn-yard grass | Giant fox-tail | Johnson-grass |
|---|---|---|---|---|---|---|---|---|---|---|---|---|
| 43 | 62.5 | — | 90 | 90 | 100 | 90 | 90 | 88 | 50 | 65 | 70 | 55 |
| 44 | 7.8 | — | 90 | 90 | 85 | 85 | 85 | 75 | 85 | 85 | 70 | 85 |
| 45 | 15.6 | — | 90 | 90 | 90 | 85 | 75 | 75 | 50 | 65 | 35 | 60 |
| 46 | 250 | 80 | 100 | 50 | 80 | 80 | 80 | 40 | 70 | 70 | 50 | 75 |
| 47 | 15.6 | 70 | 70 | 55 | 90 | 70 | 100 | 0 | 90 | 70 | 70 | 80 |
| 48 | 7.8 | 100 | 83 | 10 | 100 | 80 | 100 | 80 | 0 | 0 | 20 | 15 |
| 49 | 31.3 | 100 | 99 | 50 | 80 | 99 | 99 | 75 | 0 | 10 | 45 | 65 |
| 50 | 31.3 | 85 | 99 | 30 | 70 | 95 | 80 | 65 | 70 | 75 | 50 | 83 |
| 51 | 15.6 | 90 | 60 | 75 | 98 | 100 | 90 | 85 | 90 | 75 | 30 | 95 |
| 52 | 500 | 50 | 80 | 70 | 90 | 88 | 100 | 75 | 20 | 20 | 25 | 60 |
| 53 | 15.6 | 40 | 97 | 85 | 80 | 85 | 100 | 65 | 70 | 90 | 35 | 95 |
| 54 | 62.5 | 40 | 95 | 85 | 80 | 100 | 70 | 65 | 90 | 80 | 80 | 93 |
| 55 | 62.5 | 90 | 85 | 90 | 90 | 70 | 88 | 80 | 88 | 85 | 70 | 85 |
| 56 | 31.3 | 90 | 85 | 75 | 87 | 90 | 100 | 85 | 90 | 75 | 70 | 70 |
| 57 | 15.6 | 90 | 70 | 85 | 90 | 88 | 85 | 80 | 75 | 85 | 65 | 88 |
| 58 | 3.9 | 70 | 60 | 90 | 85 | 85 | 100 | 90 | 80 | 50 | 30 | 60 |
| 59 | 31.3 | 90 | 85 | 60 | 85 | 85 | 100 | 80 | 80 | 60 | 50 | 85 |
| 60 | 31.3 | 95 | 85 | 75 | 85 | 85 | 95 | 85 | 90 | 80 | 60 | 90 |
| 61 | 15.6 | 90 | — | 85 | 85 | 85 | 98 | 95 | 85 | 75 | 60 | 80 |
| 62 | 31.3 | 85 | — | 90 | 80 | 85 | 100 | 90 | 75 | 40 | 60 | 50 |
| 63 | 15.6 | 85 | — | 85 | 80 | 90 | 90 | 95 | 90 | 40 | 55 | 80 |
| 64 | 500 | 90 | 90 | 50 | 70 | 25 | 60 | 50 | 60 | 30 | 50 | 80 |
| 65 | 500 | 75 | 75 | 60 | 30 | 60 | 70 | 60 | 0 | 0 | 10 | 40 |
| 66 | 7.8 | 90 | 90 | 100 | 75 | 85 | 95 | 98 | 70 | 80 | 95 | 100 |
| 67 | 15.6 | 88 | — | 55 | 85 | 85 | 85 | 88 | 60 | 70 | 70 | 85 |
| 69 | 15.6 | 90 | — | 85 | 90 | 88 | 90 | 88 | 85 | 90 | 80 | 90 |
| 70 | 15.6 | 90 | 88 | 30 | 88 | 75 | 80 | 100 | 70 | 30 | 30 | 40 |
| 71 | 15.6 | 90 | 85 | 60 | 90 | 88 | 10 | 90 | 70 | 50 | 35 | 40 |
| 72 | 7.8 | 90 | 85 | 88 | 90 | 80 | 75 | 85 | 80 | 75 | 60 | 75 |
| 73 | 3.9 | 50 | 70 | 60 | 87 | 90 | 75 | 80 | 50 | 85 | 40 | 85 |
| 74 | 62.5 | 100 | 90 | 50 | 80 | 80 | 80 | 60 | 60 | 75 | 50 | 30 |
| 75 | 62.5 | 100 | 70 | 40 | 75 | 90 | 85 | 40 | 40 | 10 | 20 | 0 |
| 76 | 125 | 80 | 80 | 65 | 90 | 80 | 80 | 50 | 50 | 75 | 70 | 70 |
| 77 | 125 | 98 | 60 | 40 | 90 | 98 | 80 | 65 | 50 | 50 | 45 | 40 |
| 78 | 31.3 | 100 | 80 | 40 | 90 | 98 | 100 | 85 | 60 | 60 | 0 | 40 |
| 79 | 62.5 | 90 | — | 70 | 75 | 80 | 100 | 85 | 70 | 70 | 40 | 80 |
| 80 | 0.98 | 85 | 60 | 20 | 60 | 80 | 75 | 100 | 60 | 60 | 30 | 60 |
|  | 7.8 | 100 | 100 | 75 | 90 | 100 | 90 | 98 | 98 | 78 | 40 | 75 |
| 81 | 1.95 | 95 | 80 | 60 | 98 | 75 | 100 | 95 | 80 | 75 | 40 | 80 |
| 82 | 31.3 | 100 | 90 | 70 | 98 | 85 | 100 | 100 | 95 | 98 | 80 | 98 |
| 83 | 31.3 | 100 | 100 | 90 | 90 | 90 | 100 | 100 | 88 | 90 | 85 | 100 |
| 84 | 7.8 | 100 | 30 | 90 | 90 | 90 | 100 | 85 | 90 | 80 | 50 | 80 |
| 85 | 15.6 | 80 | 60 | 70 | 80 | 90 | 80 | 50 | 90 | 75 | 50 | 98 |
| 86 | 3.9 | 90 | 80 | 70 | 55 | 50 | 100 | 80 | 95 | 75 | 75 | 40 |
| 87 | 125 | 60 | 50 | 75 | 75 | 85 | 70 | — | 75 | 75 | 20 | 70 |
| 88 | 31.3 | 80 | 80 | 100 | 75 | 85 | 80 | 85 | 80 | 65 | 40 | 90 |
| 89 | 125 | 100 | 85 | 50 | 85 | 80 | 95 | 80 | 30 | 60 | 40 | 40 |
| 90 | 15.6 | 100 | 85 | 75 | 60 | 70 | — | 40 | 50 | 40 | 30 | 50 |
| 91 | 3.9 | 85 | 90 | 40 | 85 | 60 | 60 | 75 | 60 | 80 | 20 | 90 |
| 92 | 125 | 100 | 80 | 75 | 85 | 85 | 85 | 90 | 80 | 85 | 50 | 85 |
| 93 | 500 | 100 | 75 | 60 | 75 | 60 | 30 | 40 | 40 | 10 | 20 | 0 |
| 94 | 62.5 | 100 | 85 | 25 | 85 | 50 | 60 | 40 | 70 | 30 | 30 | 60 |
| 95 | 125 | 100 | — | 70 | 100 | 75 | 97 | 83 | 20 | 5 | 40 | 20 |
| 96 | 0.49 | 90 | 80 | 10 | 70 | 80 | 80 | 65 | 10 | 0 | 0 | 10 |
| 97 | 62.5 | 90 | 90 | 80 | 80 | 90 | 95 | 85 | 70 | 88 | 60 | 80 |
| 98 | 1.95 | 85 | 80 | 60 | 100 | 97 | 80 | 75 | 50 | 60 | 0 | 80 |
| 99 | 125 | 90 | 50 | 60 | 40 | 80 | 100 | 60 | 50 | 40 | 20 | 30 |
| 100 | 250 | 99 | — | 30 | 60 | 93 | 10 | 85 | 30 | 70 | 20 | 10 |
| 101 | 15.6 | 100 | 80 | 80 | 98 | 70 | 80 | 75 | 80 | 90 | 75 | 90 |
| 102 | 1000 | 80 | — | 0 | 0 | 10 | 0 | 0 | 0 | 0 | 0 | 0 |
| 103 | 7.8 | 93 | — | 80 | 60 | 80 | 65 | 95 | 70 | 85 | 70 | 90 |
| 104 | 31.3 | 95 | — | 97 | 70 | 75 | 80 | 97 | 90 | 80 | 60 | 99 |
| 105 | 500 | 93 | — | 55 | 20 | 70 | 60 | 65 | 45 | 65 | 45 | 35 |
| 106 | 3.9 | 85 | — | 35 | 50 | 15 | 90 | 65 | 93 | 75 | 55 | 0 |
| 107 | 500 | 97 | — | 60 | 60 | 80 | 20 | 80 | 10 | 5 | 0 | 0 |
| 108 | 1.95 | 97 | — | 70 | 75 | 90 | 80 | 80 | 40 | 50 | 50 | 55 |
| 109 | 31.3 | 98 | 90 | 55 | 90 | 65 | 65 | 75 | 0 | 10 | 0 | 40 |
| 110 | 7.8 | 90 | 65 | 85 | 65 | 70 | 85 | 70 | 15 | 65 | 60 | 65 |
| 111 | 62.5 | 99 | 60 | 97 | 93 | 75 | 97 | 70 | 75 | 70 | 65 | 70 |
| 112 | 125 | 100 | 95 | 20 | 70 | 100 | 45 | 70 | 0 | 0 | 0 | 0 |
| 113 | 62.5 | 98 | 90 | 0 | 100 | 90 | 20 | 75 | 0 | 0 | 0 | 0 |
| 114 | 500 | 90 | 75 | 50 | 75 | 90 | 0 | 0 | 0 | 0 | 0 | 0 |
| 115 | 1.95 | 100 | 85 | 70 | 100 | 80 | 65 | 65 | 45 | 0 | 60 | 50 |

TABLE 2-continued

POSTEMERGENCE HERBICIDAL ACTIVITY

| Cpd. No. | Rate, ppm | Cocklebur | Jimsonweed | Lambsquarters | Morningglory | Velvetleaf | Field Pansy | Wild Buckwheat | Blackgrass | Barnyard grass | Giant foxtail | Johnsongrass |
|---|---|---|---|---|---|---|---|---|---|---|---|---|
| 116 | 3.9 | 97 | 70 | 85 | 97 | 95 | 75 | — | 25 | 65 | 0 | 60 |
| 117 | 7.8 | 100 | 70 | 100 | 100 | 90 | 80 | 80 | 83 | 80 | 65 | 65 |
| 118 | 62.5 | 100 | 90 | 60 | 85 | 80 | 60 | 80 | 0 | 75 | 30 | 80 |
| 119 | 1000 | 100 | 15 | 0 | — | 0 | 70 | 0 | 0 | 35 | 0 | 0 |
| 120 | 125 | 100 | 60 | 60 | 85 | 75 | 75 | 0 | 40 | 35 | 0 | 0 |
| 121 | 62.5 | 100 | 85 | 40 | 98 | 78 | 80 | 78 | 75 | 70 | 65 | 70 |
| 122 | 62.5 | 90 | 90 | 40 | 80 | 85 | 70 | 80 | 0 | 75 | 70 | 75 |
| 123 | 15.6 | 90 | 90 | 70 | 80 | 75 | 90 | 75 | 60 | 75 | 80 | 55 |
| 124 | 1000 | 75 | 80 | 0 | 80 | 30 | 75 | 50 | 0 | 30 | 0 | 0 |
| 125 | 500 | 85 | 80 | 80 | 75 | 40 | 90 | 30 | 78 | 80 | 40 | 80 |
| 126 | 15.6 | 100 | 85 | 80 | 98 | 80 | 50 | 80 | 0 | 0 | 50 | 0 |
| 127 | 62.5 | 100 | 75 | 80 | 80 | 80 | 70 | 80 | 80 | 75 | 75 | 75 |
| 128 | 31.3 | 85 | 90 | 75 | 75 | 80 | 90 | 80 | 75 | 60 | 60 | 75 |
| 129 | 15.6 | 100 | 90 | 75 | 90 | 70 | 75 | 80 | 75 | 75 | 98 | 90 |
| 130 | 31.3 | — | 100 | 60 | 80 | 75 | 85 | 60 | 90 | 80 | — | 80 |
| 131 | 250 | — | 98 | 50 | 90 | 90 | 75 | 80 | 50 | 30 | — | 75 |
| 132 | 3.9 | — | 100 | 30 | 85 | 90 | 80 | 80 | 85 | 55 | — | 75 |
| 133 | 125 | — | 98 | 30 | 95 | 90 | 85 | 80 | 90 | 45 | — | 75 |
| 134 | 15.6 | 90 | 80 | 95 | 90 | 70 | 85 | — | 50 | 70 | 20 | 50 |
| 135 | 31.3 | 90 | — | 85 | 90 | 85 | — | 85 | 75 | 65 | 75 | — |
| 136 | 125 | 70 | 90 | 80 | 90 | 75 | 80 | 80 | 75 | 75 | 0 | 70 |
| 137 | 500 | 95 | — | 70 | 75 | 70 | — | 75 | 80 | 5 | 60 | — |
| 138 | 31.3 | 90 | 90 | 90 | 80 | 80 | 70 | 80 | 98 | 85 | 70 | 95 |
| 139 | 31.3 | 90 | 95 | 75 | 85 | 80 | 75 | 75 | 98 | 90 | 75 | 90 |
| 140 | 31.3 | 80 | 90 | 95 | 85 | 75 | 75 | 85 | 75 | 75 | 60 | 75 |
| 141 | 1000 | 70 | 80 | 60 | 70 | 40 | 75 | 75 | 20 | 20 | 0 | 40 |
| 142 | 500 | 85 | — | 20 | 100 | 75 | — | 70 | 40 | 0 | 55 | — |
| 143 | 250 | 95 | — | 0 | 90 | 75 | — | 70 | — | 0 | 30 | — |
| 144 | 500 | 89 | — | 0 | 70 | 20 | — | 55 | — | 0 | 50 | — |
| 145 | 7.8 | 100 | — | 89 | 90 | 88 | — | 65 | 75 | 65 | 30 | — |
| 146 | 7.8 | 85 | — | 80 | 100 | 80 | — | 80 | 30 | 60 | 40 | — |
| 147 | 31.3 | 80 | — | 60 | 90 | 80 | — | 88 | 80 | 80 | 75 | — |
| 148 | 31.3 | 98 | — | 90 | 75 | 95 | — | 75 | 75 | 80 | 80 | — |
| 151 | 31.3 | 98 | — | 90 | 80 | 95 | — | 80 | 75 | 80 | 70 | — |
| 152 | 1000 | 98 | — | 50 | 85 | 30 | — | 75 | 70 | 60 | 60 | — |
| 153 | 62.5 | 88 | — | 75 | 100 | 85 | — | 80 | 65 | 55 | 70 | — |
| 154 | 15.6 | 100 | — | 80 | 100 | 85 | — | 75 | 70 | 80 | 75 | — |
| 155 | 6205 | 100 | — | 90 | 100 | 90 | — | 85 | 88 | 85 | 75 | — |
| 156 | 125 | 85 | — | 85 | 80 | 70 | — | 80 | 85 | 80 | 80 | — |
| 157 | 15.6 | 100 | — | 60 | 100 | 78 | — | 85 | 60 | 80 | 70 | — |
| 158 | 7.8 | 100 | — | 40 | 86 | 89 | — | 75 | 20 | 25 | 30 | — |
| 159 | 31.3 | 90 | — | 85 | 85 | 88 | — | 88 | 80 | 85 | 85 | — |
| 160 | 62.5 | 90 | — | 85 | 90 | 80 | — | 80 | 88 | 80 | 85 | — |
| 161 | 125 | 80 | — | 85 | 85 | 80 | — | 85 | 80 | 80 | 80 | — |
| 162 | 31.3 | 100 | — | 80 | 90 | — | — | — | 0 | 30 | 60 | — |
| 163 | 125 | 80 | — | 95 | 95 | — | — | — | 50 | 75 | 85 | — |
| 164 | 125 | 90 | — | 80 | 100 | — | — | — | 0 | 20 | 50 | — |
| 165 | 15.6 | 100 | — | 90 | 100 | — | — | — | 75 | 80 | 95 | — |
| 166 | 1.95 | 90 | — | 85 | 95 | — | — | — | 50 | 85 | 85 | — |
| 167 | 31.3 | 90 | — | 95 | 100 | — | — | — | 30 | 75 | 90 | — |
| 168 | 62.5 | 100 | — | 88 | 90 | 80 | — | 80 | 85 | 80 | 88 | — |
| 169 | 15.6 | 95 | — | 90 | 100 | 85 | — | 85 | 75 | 85 | 90 | — |
| 170 | 31.3 | 90 | — | 85 | 85 | 70 | — | 85 | 90 | 85 | 80 | — |
| 171 | 31.3 | 100 | — | 70 | 90 | 90 | — | 85 | 90 | 70 | 25 | — |
| 172 | 125 | 90 | — | 80 | 90 | 90 | — | 85 | 70 | 75 | 60 | — |
| 173 | 125 | 95 | — | 30 | 95 | 75 | — | 85 | 35 | 30 | 0 | — |
| 174 | 31.3 | 100 | — | 85 | 90 | 80 | — | 80 | 75 | 80 | 60 | — |
| 176 | 31.3 | 100 | — | 75 | 85 | 88 | — | 85 | 70 | 70 | 60 | — |
| 177 | 125 | 100 | — | 60 | 85 | 85 | — | 85 | 40 | 20 | 50 | — |
| 178 | 31.3 | 100 | — | 80 | 95 | 90 | — | 80 | 70 | 80 | 60 | — |
| 179 | 62.5 | 100 | — | 60 | 80 | 85 | — | 80 | 15 | 20 | 20 | — |
| 180 | 250 | 95 | — | 50 | 95 | 75 | — | 80 | 30 | 30 | 25 | — |
| 181 | 125 | 85 | — | 88 | 88 | 85 | — | 78 | 60 | 80 | 70 | — |
| 182 | 500 | 100 | — | 72 | 85 | 90 | — | 75 | 20 | 0 | 30 | — |
| 183 | 500 | 90 | — | 60 | 100 | 90 | — | 85 | 20 | 10 | 15 | — |
| 186 | 250 | 100 | — | 90 | 85 | 88 | — | 80 | 80 | 80 | 85 | — |
| 187 | 62.5 | 90 | — | 90 | 85 | 90 | — | 85 | 85 | 85 | 80 | — |
| 188 | 31.3 | 90 | — | 60 | 85 | 35 | — | 80 | 35 | 75 | 60 | — |
| 189 | 31.3 | 90 | — | 85 | 85 | 75 | — | 85 | 25 | 25 | 40 | — |
| 190 | 7.8 | 100 | — | 80 | 95 | 85 | — | 85 | 40 | 70 | 30 | — |
| 191 | 3.9 | 100 | — | 70 | 90 | 80 | — | 80 | 10 | 50 | 40 | — |
| 192 | 62.5 | 75 | — | 80 | 80 | 70 | — | 80 | 80 | 75 | 60 | — |
| 193 | 31.3 | 100 | — | 70 | 95 | 55 | — | 70 | 50 | 80 | 50 | — |

TABLE 2-continued

POSTEMERGENCE HERBICIDAL ACTIVITY

| Cpd. No. | Rate, ppm | Cockle-bur | Jimson-weed | Lambs-quarters | Morning-glory | Velvet-leaf | Field Pansy | Wild Buck-wheat | Black-grass | Barn-yard grass | Giant fox-tail | Johnson-grass |
|---|---|---|---|---|---|---|---|---|---|---|---|---|
| 194 | 15.6 | 100 | — | 70 | 90 | 60 | — | 60 | 80 | 80 | 85 | — |
| 195 | 250 | 80 | — | 70 | 75 | 50 | — | 80 | 70 | 70 | 70 | — |
| 198 | 31.3 | 100 | — | 98 | 80 | 98 | — | 90 | 30 | 50 | 70 | — |
| 199 | 62.5 | 98 | — | 80 | 100 | 95 | — | 90 | 50 | 80 | 75 | — |
| 200 | 62.5 | 95 | — | 60 | 85 | 70 | — | 80 | 85 | 90 | 75 | — |
| 201 | 31.3 | 100 | — | 85 | 90 | 95 | — | 90 | 60 | 85 | 60 | — |
| 202 | 125 | 85 | — | 90 | 90 | 85 | — | 90 | 80 | 85 | 85 | — |
| 203 | 125 | 50 | — | 85 | 85 | 80 | — | 80 | 90 | 85 | 95 | — |
| 204 | 250 | 90 | — | 85 | 90 | 75 | — | 80 | 40 | 75 | 30 | — |
| 205 | 62.5 | 90 | — | 90 | 90 | 90 | — | 85 | 90 | 85 | 80 | — |
| 208 | 31.3 | 90 | — | 80 | 90 | 70 | — | 90 | 40 | 70 | 75 | — |
| 212 | 15.6 | 100 | — | 40 | 90 | 40 | — | 85 | 90 | 65 | 40 | — |

TABLE 2A

POSTEMERGENCE HERBICIDAL ACTIVITY

| Cpd. No. | Rate, ppm | Chick-weed | Cockle-bur | Lambs-quarters | Morning-glory | Velvet-leaf | Field Pansy | Wild Buck-wheat | Black-grass | Barn-yard grass | Giant fox-tail | Rox Orange Sorghum |
|---|---|---|---|---|---|---|---|---|---|---|---|---|
| 213 | 7.8 | 95 | 98 | 50 | 100 | 85 | 80 | 90 | 40 | 40 | 0 | 95 |
| 214 | 7.8 | 90 | 90 | 60 | 80 | 70 | 70 | 90 | 80 | 65 | 50 | 95 |
| 215 | 15.6 | 70 | 90 | 75 | 85 | 70 | 80 | 90 | 90 | 75 | 10 | 98 |
| 216 | 7.8 | 98 | 90 | 75 | 90 | 70 | 90 | 85 | 90 | 75 | 20 | 95 |
| 217 | 125 | 75 | 90 | 75 | 90 | 85 | 85 | 75 | 85 | 80 | 78 | 90 |
| 218 | 31.3 | 100 | 70 | 65 | 85 | 85 | 78 | 85 | 35 | 30 | 30 | 55 |
| 219 | 31.3 | 90 | 75 | 75 | 80 | 75 | 80 | 85 | 70 | 40 | 60 | 95 |
| 220 | 125 | 90 | 80 | 70 | 80 | 85 | 88 | 85 | 75 | 40 | 60 | 60 |
| 221 | 62.5 | 85 | 85 | 70 | 75 | 75 | 85 | 85 | 75 | 75 | 70 | 60 |
| 223 | 31.3 | 90 | 70 | 90 | 90 | 60 | 90 | 60 | 85 | 65 | 65 | 90 |
| 224 | 500 | 50 | 70 | 100 | 70 | 75 | 90 | 85 | 85 | 35 | 20 | 78 |
| 225 | 250 | 80 | 85 | — | 80 | 60 | 90 | 80 | 85 | 80 | 35 | 70 |
| 226 | 7.8 | 90 | 100 | 98 | 70 | 75 | 80 | 80 | 80 | 78 | 70 | 90 |
| 227 | 7.8 | 90 | 100 | 95 | 70 | 70 | 90 | 80 | 95 | 80 | 78 | 90 |
| 228 | 62.5 | 95 | 100 | 90 | 90 | 85 | 90 | 75 | 90 | 80 | 90 | 95 |
| 229 | 62.5 | 95 | 90 | 90 | 50 | 75 | 75 | 80 | 60 | 75 | 60 | 60 |
| 230 | 125 | 70 | — | 95 | 88 | 90 | 90 | 80 | 88 | 85 | 80 | 85 |
| 231 | 125 | 78 | — | 95 | 85 | 90 | 88 | 85 | 90 | 88 | 30 | 88 |
| 232 | 15.6 | 70 | — | 90 | 90 | 88 | 95 | 90 | 80 | 75 | 75 | 90 |
| 233 | 31.3 | 85 | — | 90 | 80 | 85 | 0 | 85 | 83 | 85 | 95 | 90 |
| 234 | 15.6 | 85 | 99 | 100 | 80 | 95 | 83 | 95 | 98 | 78 | 85 | 95 |
| 235 | 7.8 | 95 | 98 | 99 | 75 | 75 | 85 | 85 | 85 | 78 | 55 | 78 |
| 236 | 15.6 | 98 | 100 | 100 | 75 | 70 | 83 | 80 | 85 | 80 | 50 | 78 |
| 238 | 15.6 | 90 | 100 | 95 | 80 | 90 | 85 | 80 | 80 | 78 | 55 | 78 |
| 239 | 15.6 | 80 | 70 | 95 | 90 | 70 | 78 | 95 | 98 | 75 | 78 | 78 |
| 240 | 7.8 | 78 | 98 | 98 | 75 | 70 | 75 | 88 | 98 | 78 | 65 | 75 |
| 241 | 31.3 | 80 | 90 | 40 | 75 | 95 | 80 | 80 | 0 | 0 | 0 | 0 |
| 242 | 3.9 | 85 | 100 | 90 | 95 | 95 | 85 | 80 | 60 | 70 | 40 | 99 |
| 243 | 3.9 | 90 | 100 | 100 | 95 | 80 | 80 | 50 | 70 | 75 | 35 | 78 |
| 244 | 31.3 | 98 | 100 | 98 | 98 | 65 | 85 | 75 | 95 | 78 | 98 | 78 |
| 245 | 125 | 40 | — | 60 | 75 | 75 | 75 | 80 | — | 75 | 10 | 20 |
| 246 | 62.5 | 79 | — | 90 | 85 | 90 | 85 | 85 | — | 88 | 88 | 88 |
| 247 | 62.5 | 70 | — | 90 | 85 | 80 | 90 | 85 | — | 88 | 80 | 88 |
| 248 | 125 | 70 | — | 70 | 80 | 80 | 85 | 88 | — | 85 | 90 | 90 |
| 249 | 125 | 70 | — | 90 | 80 | 65 | 90 | 80 | — | 85 | 75 | 90 |
| 250 | 31.3 | 88 | 100 | 100 | 93 | 95 | 70 | 88 | 90 | 78 | 83 | 99 |
| 251 | 62.5 | 95 | 100 | 100 | 95 | 98 | 60 | 80 | 98 | 75 | 78 | 98 |
| 252 | 7.8 | 95 | 95 | 95 | 95 | 95 | 78 | 85 | 25 | 25 | 35 | 75 |
| 253 | 62.5 | 80 | 95 | 95 | 85 | 78 | 85 | 80 | 60 | 80 | 78 | 80 |
| 254 | 31.3 | 95 | 90 | 100 | 90 | 75 | 80 | 80 | 80 | 90 | 75 | 85 |
| 255 | 31.3 | 95 | 95 | 90 | 85 | 95 | 78 | 85 | 50 | 70 | 78 | 85 |
| 256 | 125 | 85 | 90 | 90 | 70 | 75 | 90 | 75 | 65 | 55 | 78 | 65 |
| 257 | 31.3 | 90 | 95 | 90 | 80 | 70 | 85 | 78 | 80 | 90 | 95 | 78 |
| 258 | 97.5 | 35 | 95 | 95 | 75 | 83 | 83 | 85 | 90 | 60 | 70 | 78 |

70. Evaluation of Preemergence Herbicidal Activity

Seeds of the desired test plant species were planted in a soil matrix prepared by mixing a loam soil which was composed of about 43 percent silt, 19 percent clay, and 38 percent sand and had a pH of about 8.1 and an organic matter content of about 1.5 percent and sand in a 70 to 30 ratio. The soil matrix was contained in plastic pots with a surface area of 161 square centimeters. When required to ensure good germination and healthy plants, a fungicide treatment and/or other chemical or physical treatment was applied.

A weighed amount, determined by the highest rate to be tested, of each test compound was placed in a 20 mL glass vial and was dissolved in 8 mL of a 97:3 v/v (volume/volume) mixture of acetone and dimethyl sulfoxide to obtain concentrated stock solutions. If the test compound did not dissolve readily, the mixture was warmed and/or sonicated. The stock solutions obtained were diluted with a 99.9:0.1 mixture of water and Tween® 155 surfactant to obtain application solutions of known concentration. The solutions containing the highest concentration to be tested were prepared by diluting 4 mL aliquots of the stock solution with 8.5 mL of the mixture and lower concentrations were prepared by dilution of appropriate smaller portions of the stock solution. A 2.5 mL aliquot of each solution of known concentration was sprayed evenly onto the soil of each seeded pot using a Cornwall 5.0 mL glass syringe fitted with a TeeJet TN-3 hollow cone nozzle to obtain thorough coverage of the soil in each pot. Control pots were sprayed in the same manner with the aqueous mixture. A highest application rate of 4.48 Kg/Ha is achieved when 50 mg of test compound is employed.

The treated pots and control pots were placed in a greenhouse with an approximately 15 hr photoperiod which was maintained at about 23°–29° C. during the day and 22°–28° C. during the night. Nutrients and water were added on a regular basis and supplemental lighting was provided with overhead metal halide 1000 Watt lamps as necessary. The water was added by top-irrigation. After 3 weeks the condition of the test plants that germinated and grew as compared with that of the untreated plants that germinated and grew was determined visually and scored on a scale of 0 to 100 percent where 0 corresponds to no injury and 100 corresponds no complete kill or no germination. Some of the compounds nested, application rates employed, plant species tested, and results are given in Table 3.

TABLE 3

PREEMERGENCE HERBICIDAL ACTIVITY

| Cpd. No. | Rate, Kg/Ha | Morning-glory | Pigweed | Velvet-leaf | Wild Buck-wheat | Black-grass | Barn-yard Grass | Giant fox-tail | Johnson-grass | Wild oats |
|---|---|---|---|---|---|---|---|---|---|---|
| 1 | 0.56 | 85 | 95 | 90 | 90 | 40 | 50 | 40 | 70 | 40 |
| 2 | 0.28 | 80 | 99 | 95 | 95 | 40 | 20 | 70 | 70 | 30 |
| 3 | 0.56 | 40 | 100 | 90 | — | 0 | — | 30 | 0 | 50 |
| 4 | 0.28 | 80 | 100 | 95 | 75 | 75 | 80 | 75 | 65 | 60 |
| 5 | 0.14 | 80 | 90 | 95 | 40 | 70 | 60 | 60 | 75 | 30 |
| 6 | 0.56 | 60 | 0 | 65 | 10 | 40 | 80 | 0 | 30 | 30 |
| 7 | 1.12 | 80 | 100 | 90 | 50 | 95 | 98 | 60 | 80 | 0 |
| 8 | 0.018 | 75 | 98 | 80 | 80 | 100 | 100 | 80 | 90 | 80 |
| 9 | 0.035 | 80 | 98 | 80 | 85 | 100 | 98 | 70 | 80 | 60 |
| 10 | 0.28 | 90 | 95 | 60 | 50 | 98 | 90 | 75 | 80 | 55 |
| 11 | 0.14 | 90 | 85 | 75 | 50 | 95 | 98 | 50 | 40 | 0 |
| 12 | 0.14 | 80 | 100 | 85 | 60 | 90 | 80 | 65 | 50 | 50 |
| 13 | 0.035 | 60 | 100 | 85 | 85 | 100 | 98 | 95 | 80 | 75 |
| 14 | 0.28 | 85 | 98 | 85 | 60 | 95 | 98 | 55 | 60 | 45 |
| 16 | 0.28 | 70 | 80 | 70 | — | 70 | 80 | 60 | 40 | 70 |
| 17 | 0.28 | 90 | 100 | 75 | — | 70 | 70 | 50 | 40 | 50 |
| 18 | 0.28 | 80 | 95 | 60 | — | 50 | 50 | 80 | 40 | 75 |
| 19 | 0.14 | 95 | 98 | 95 | 98 | 85 | 95 | 97 | 98 | 88 |
| 20 | 0.070 | 95 | 95 | 90 | 92 | 60 | 80 | 75 | 85 | 70 |
| 21 | 0.14 | 90 | 98 | 85 | 95 | 85 | 75 | 75 | 70 | 75 |
| 22 | 2.24 | 85 | 95 | 85 | 60 | 60 | 65 | 70 | 65 | 10 |
| 23 | 0.070 | 90 | 98 | 95 | 92 | 85 | 90 | 92 | 99 | 90 |
| 24 | 0.070 | 90 | 95 | 90 | 92 | 70 | 78 | 80 | 90 | 50 |
| 25 | 0.035 | 90 | 98 | 80 | 50 | 70 | 95 | 40 | 60 | 50 |
| 26 | 0.56 | 90 | 100 | 85 | 60 | 50 | 65 | 40 | 70 | 20 |
| 27 | 0.28 | 60 | 100 | 85 | 50 | 98 | 70 | 60 | 30 | 0 |
| 28 | 0.018 | 50 | 90 | 75 | 85 | 90 | 90 | 50 | 75 | 20 |
| 29 | 1.12 | 60 | 98 | 60 | 70 | 90 | 100 | 75 | 85 | 50 |
| 30 | 0.035 | 90 | 100 | 65 | 95 | 90 | 98 | 90 | 85 | 40 |
| 31 | 0.14 | 90 | 100 | 90 | 100 | 40 | 90 | 70 | 90 | 20 |
| 32 | 0.070 | 85 | 100 | 85 | 90 | 98 | 98 | 90 | 98 | 40 |
| 33 | 0.035 | 50 | 100 | 25 | 100 | 70 | 98 | 90 | 85 | 20 |
| 34 | 0.070 | 90 | 100 | 90 | 90 | 98 | 95 | 40 | 85 | 50 |
| 35 | 0.070 | 90 | 100 | 80 | 90 | 15 | 10 | 20 | 10 | 0 |
| 36 | 0.070 | 60 | 98 | 70 | 85 | 60 | 85 | 60 | 80 | 60 |
| 37 | 0.035 | 95 | 100 | 75 | 100 | 20 | 65 | 60 | 0 | 0 |
| 38 | 0.070 | 85 | 100 | 60 | 100 | 0 | 50 | 20 | 0 | 10 |
| 40 | 0.035 | 40 | 99 | 65 | 95 | 95 | 90 | 40 | 80 | 20 |
| 41 | 0.070 | 90 | 100 | 60 | 100 | 20 | 99 | 80 | 85 | 10 |
| 42 | 0.070 | 90 | 100 | 90 | 90 | 98 | 80 | 70 | 80 | 50 |
| 43 | 0.070 | 50 | 98 | 60 | 85 | 30 | 60 | 60 | 20 | 0 |
| 44 | 0.070 | 90 | 100 | 60 | 90 | 98 | 95 | 98 | 90 | 60 |
| 45 | 0.070 | 85 | 100 | 80 | 90 | 100 | 95 | 60 | 85 | 20 |
| 46 | 0.56 | 50 | 100 | 50 | 60 | 80 | 60 | 50 | 60 | 0 |
| 47 | 0.070 | 80 | 0 | 60 | 90 | 99 | 85 | 90 | 85 | 50 |
| 49 | 0.035 | 80 | 100 | 40 | 99 | 0 | 0 | 50 | 10 | 0 |
| 50 | 0.070 | 90 | 100 | 90 | 40 | 98 | 98 | 80 | 90 | 80 |

TABLE 3-continued

PREEMERGENCE HERBICIDAL ACTIVITY

| Cpd. No. | Rate, Kg/Ha | Morning-glory | Pigweed | Velvet-leaf | Wild Buck-wheat | Black-grass | Barn-yard Grass | Giant fox-tail | Johnson-grass | Wild oats |
|---|---|---|---|---|---|---|---|---|---|---|
| 51 | 0.035 | 60 | 98 | 100 | 90 | 60 | 95 | 60 | 80 | 50 |
| 52 | 0.56 | 85 | 98 | 85 | 80 | 40 | 50 | 40 | 50 | 20 |
| 53 | 0.035 | 10 | 90 | 90 | 95 | 98 | 80 | 90 | 80 | 80 |
| 54 | 0.56 | 90 | 100 | 90 | 80 | 60 | 40 | 30 | 20 | 20 |
| 55 | 0.56 | 90 | 90 | 90 | 88 | 90 | 87 | 70 | 90 | 78 |
| 56 | 0.28 | 90 | 90 | 85 | 90 | 85 | 85 | 80 | 85 | 75 |
| 57 | 0.14 | 90 | 88 | 90 | 90 | 80 | 90 | 80 | 85 | 65 |
| 58 | 0.018 | 90 | 98 | 85 | 85 | 90 | 65 | 40 | 75 | 40 |
| 59 | 0.035 | 80 | 95 | 88 | 90 | 95 | 70 | 50 | 80 | 50 |
| 60 | 0.070 | 85 | 98 | 80 | 95 | 90 | 70 | 60 | 85 | 50 |
| 61 | 0.035 | 90 | 98 | 80 | 85 | 90 | 80 | 80 | 90 | 65 |
| 62 | 0.14 | 90 | 100 | 95 | 90 | 100 | 85 | 78 | 80 | 50 |
| 63 | 0.070 | 95 | 90 | 80 | 80 | 60 | 70 | 70 | — | 60 |
| 64 | 1.12 | 55 | 45 | 0 | 0 | 0 | 0 | 0 | 90 | 0 |
| 65 | 2.24 | 75 | 80 | 55 | 45 | 20 | 45 | 45 | 10 | 25 |
| 66 | 0.070 | 90 | 98 | 95 | 98 | 98 | 85 | 80 | 98 | 90 |
| 67 | 0.035 | 85 | 90 | 88 | 90 | 70 | 60 | 75 | 75 | 50 |
| 68 | 0.15 | 85 | 95 | 92 | 50 | 40 | 60 | 60 | 75 | 20 |
| 69 | 0.070 | 95 | 95 | 90 | 95 | 80 | 85 | 90 | 100 | 88 |
| 70 | 0.28 | 90 | 90 | 85 | 90 | 85 | 75 | 70 | 75 | 50 |
| 71 | 0.070 | 90 | 60 | 80 | 92 | 70 | 65 | 50 | 95 | 25 |
| 72 | 0.14 | 90 | 90 | 85 | 90 | 95 | 75 | 70 | 88 | 65 |
| 73 | 0.070 | 90 | 85 | 80 | 88 | 90 | 80 | 75 | 85 | 40 |
| 74 | 0.56 | 80 | 100 | 90 | 80 | 80 | 98 | 80 | 60 | 50 |
| 75 | 0.56 | 80 | 98 | 80 | 80 | 20 | 50 | 30 | 40 | 0 |
| 76 | 0.28 | 75 | 100 | 70 | 60 | 50 | 95 | 60 | 60 | 50 |
| 77 | 0.56 | 80 | 100 | 70 | 60 | 50 | 30 | 30 | 40 | 20 |
| 78 | 0.28 | 90 | 100 | 85 | 40 | 65 | 90 | 60 | — | 0 |
| 79 | 0.28 | 85 | 100 | 60 | 40 | 80 | 95 | 50 | — | 50 |
| 80 | 0.018 | 95 | 95 | 80 | 60 | 90 | 60 | 80 | — | 0 |
| 81 | 0.009 | 30 | 98 | 30 | 80 | 85 | 95 | 85 | — | 0 |
|  | 0.070 | 100 | 100 | 98 | 95 | 90 | 100 | 95 | — | 90 |
| 82 | 0.035 | 80 | 100 | 80 | 95 | 98 | 90 | 90 | 80 | 60 |
| 83 | 0.035 | 30 | 98 | 60 | 85 | 90 | 90 | 60 | 80 | 65 |
| 84 | 0.070 | 85 | 100 | 75 | 85 | 100 | 98 | 50 | 50 | 70 |
| 85 | 0.070 | 75 | 100 | 50 | 80 | 80 | 90 | 75 | 98 | 70 |
| 86 | 0.28 | 100 | 100 | 70 | 90 | 98 | 98 | 90 | 90 | 75 |
| 87 | 0.56 | 85 | 100 | 85 | 40 | 100 | 98 | 75 | 85 | 50 |
| 88 | 0.070 | 90 | 95 | 85 | 90 | 75 | 85 | 78 | 98 | 80 |
| 89 | 0.28 | 90 | 90 | 80 | 20 | 60 | 90 | 85 | — | 30 |
| 90 | 0.28 | 80 | 85 | 90 | 70 | 98 | 95 | 90 | 90 | 85 |
| 91 | 0.14 | 95 | 90 | 90 | 75 | 90 | 95 | 80 | — | 80 |
| 92 | 0.28 | 95 | 95 | 90 | 40 | 95 | 90 | 90 | — | 70 |
| 93 | 1.12 | 80 | 50 | 50 | 40 | 0 | 50 | 0 | 30 | 20 |
| 94 | 1.12 | 90 | 80 | 80 | 90 | 99 | 90 | 90 | 95 | 90 |
| 95 | 1.12 | 90 | 90 | 80 | 80 | 25 | 65 | 60 | 30 | 10 |
| 96 | 0.14 | 90 | 98 | 95 | 95 | 88 | 70 | 60 | 65 | 65 |
| 97 | 0.035 | 85 | 90 | 90 | 95 | 80 | 70 | 80 | 90 | 65 |
| 98 | 0.009 | 85 | 95 | 80 | 85 | 85 | 45 | 60 | 90 | 20 |
|  | 0.070 | 90 | 98 | 85 | 98 | 95 | 95 | 98 | 98 | 85 |
| 99 | 0.14 | 90 | 90 | 70 | 80 | 70 | 65 | 85 | 70 | 50 |
| 100 | 0.56 | 70 | 75 | 80 | 100 | 80 | 60 | 70 | 70 | 40 |
| 101 | 0.070 | 85 | 98 | 80 | 90 | 80 | 90 | 80 | 95 | 80 |
| 103 | 0.035 | 90 | 95 | 80 | 95 | 80 | 98 | 85 | 98 | 70 |
| 104 | 0.035 | 90 | 90 | 80 | 90 | 98 | 98 | 80 | 98 | 75 |
| 105 | 0.070 | 60 | 70 | 40 | 30 | 50 | 50 | 50 | 75 | 10 |
| 106 | 0.070 | 90 | 95 | 60 | 95 | 100 | 95 | 95 | 95 | 75 |
| 107 | 0.070 | 40 | 80 | 20 | 60 | 0 | 0 | 0 | 0 | 0 |
| 108 | 0.018 | 90 | 98 | 85 | 95 | 98 | 90 | 80 | 98 | 50 |
| 109 | 0.28 | 90 | 98 | 80 | 90 | 95 | 75 | 45 | 90 | 50 |
| 110 | 0.14 | 90 | 95 | 75 | 85 | 95 | 85 | 80 | 95 | 85 |
| 111 | 0.070 | 85 | 90 | 90 | 95 | 90 | 95 | 90 | 90 | 85 |
| 112 | 1.12 | 60 | 100 | 85 | 30 | 30 | 40 | 50 | 60 | 30 |
| 113 | 1.12 | 80 | 100 | 90 | 60 | 30 | 80 | 30 | 70 | 0 |
| 114 | 1.12 | 30 | 80 | 50 | 30 | 0 | 20 | 20 | 0 | 0 |
| 115 | 0.070 | 90 | 95 | 95 | 80 | 95 | 85 | 70 | 100 | 70 |
| 116 | 0.009 | 80 | 90 | 90 | 60 | 60 | 40 | 50 | 80 | 60 |
| 117 | 0.035 | 80 | 100 | 85 | 100 | 99 | 90 | 90 | 90 | 90 |
| 118 | 0.56 | 80 | 90 | 50 | 70 | 95 | 50 | 80 | 90 | 60 |
| 121 | 0.56 | 85 | 95 | 80 | 90 | 95 | 60 | 90 | 90 | 80 |
| 122 | 0.14 | 85 | 95 | 90 | 95 | 30 | 95 | 90 | 90 | 50 |
| 123 | 0.070 | 80 | 99 | 80 | 90 | 70 | 90 | 90 | 90 | 85 |
| 125 | 1.12 | 90 | 70 | 50 | 30 | 85 | 90 | 95 | 95 | 80 |

TABLE 3-continued

PREEMERGENCE HERBICIDAL ACTIVITY

| Cpd. No. | Rate, Kg/Ha | Morning-glory | Pigweed | Velvet-leaf | Wild Buck-wheat | Black-grass | Barn-yard Grass | Giant fox-tail | Johnson-grass | Wild oats |
|---|---|---|---|---|---|---|---|---|---|---|
| 126 | 0.28 | 95 | 85 | 98 | 90 | 95 | 85 | 70 | 95 | 90 |
| 127 | 0.28 | 50 | 75 | 80 | 70 | 25 | 10 | 0 | 85 | 80 |
| 128 | 0.14 | 90 | 85 | 80 | 60 | 95 | 75 | 20 | 85 | 90 |
| 129 | 0.018 | 98 | 70 | 90 | 85 | 98 | 80 | 80 | 80 | 90 |
| 130 | 0.070 | 90 | 95 | 88 | — | 98 | 85 | 85 | — | 85 |
| 131 | 0.56 | 90 | 95 | 85 | — | 60 | 65 | 65 | — | 35 |
| 132 | 0.035 | 90 | 95 | 95 | — | — | 95 | 75 | — | 60 |
| 133 | 0.14 | 90 | 100 | 90 | — | 95 | 80 | 75 | — | 70 |
| 134 | 0.035 | 90 | 85 | 80 | — | 65 | 90 | 60 | — | 70 |
| 135 | 0.018 | 95 | 90 | 95 | — | 99 | 98 | 95 | — | 85 |
| 136 | 0.14 | 80 | 95 | 80 | — | 90 | 90 | 50 | — | 40 |
| 138 | 0.035 | 85 | 95 | 80 | — | 98 | 90 | 90 | — | 80 |
| 139 | 0.018 | 90 | 90 | 80 | — | 90 | 85 | 80 | — | 90 |
| 140 | 0.070 | 85 | 95 | 95 | — | 70 | 90 | 70 | — | 95 |
| 145 | 0.14 | 90 | 70 | 70 | — | 50 | 50 | 50 | — | 30 |
| 146 | 0.14 | 90 | 90 | 80 | — | 60 | 60 | 50 | — | 60 |
| 147 | 0.14 | 70 | 90 | 85 | — | 80 | 50 | 95 | — | 85 |
| 148 | 0.14 | 85 | 80 | 98 | — | 90 | 95 | 90 | — | 90 |
| 151 | 0.14 | 90 | 90 | 80 | — | 80 | 95 | 80 | — | 50 |
| 152 | 0.14 | 0 | 30 | 40 | — | 80 | 30 | 0 | — | 0 |
| 153 | 0.070 | 90 | 85 | 90 | — | 40 | 60 | 60 | — | 20 |
| 154 | 0.035 | 90 | 90 | 50 | — | 90 | 70 | 80 | — | 80 |
| 155 | 0.035 | 90 | 90 | 80 | — | 90 | 85 | 70 | — | 90 |
| 156 | 0.070 | 40 | 60 | 0 | — | 40 | 60 | 80 | — | 80 |
| 157 | 0.035 | 90 | 70 | 80 | — | 75 | 70 | 50 | — | 70 |
| 158 | 0.070 | 90 | 99 | 90 | — | 70 | 75 | 70 | — | 60 |
| 159 | 0.56 | 85 | 95 | 90 | — | 95 | 90 | 95 | — | 90 |
| 160 | 0.035 | 80 | 90 | 95 | — | 99 | 40 | 85 | — | 85 |
| 161 | 0.14 | 85 | 70 | 90 | — | 98 | 90 | 90 | — | 80 |
| 162 | 0.14 | 90 | 95 | 90 | — | 40 | 60 | 60 | — | 40 |
| 163 | 0.28 | 90 | 85 | 85 | — | 70 | 50 | 30 | — | 60 |
| 164 | 0.56 | 80 | 80 | 80 | — | 50 | 40 | 30 | — | 50 |
| 165 | 0.035 | 95 | 90 | 95 | — | 85 | 90 | 95 | — | 75 |
| 166 | 0.035 | 75 | 90 | 60 | — | 90 | 85 | 80 | — | 85 |
| 167 | 0.14 | 90 | 80 | 90 | — | 60 | 85 | 80 | — | 50 |
| 168 | 0.035 | 90 | 95 | 90 | — | 99 | 98 | 95 | — | 95 |
| 169 | 0.018 | 90 | 90 | 90 | — | 70 | 85 | 70 | — | 70 |
| 170 | 0.035 | 80 | 98 | 90 | — | 98 | 70 | 90 | — | 95 |
| 171 | 0.018 | 80 | 90 | 90 | — | 90 | 30 | 65 | — | 75 |
| 172 | 0.14 | 75 | 98 | 80 | — | 75 | 85 | 75 | — | 80 |
| 173 | 0.28 | 75 | 80 | 80 | — | 70 | 40 | 50 | — | 75 |
| 175 | 0.070 | 85 | 98 | 85 | — | 95 | 95 | 95 | — | 80 |
| 176 | 0.070 | 90 | 98 | 95 | — | 85 | 90 | 70 | — | 70 |
| 177 | 0.56 | 75 | 100 | 85 | — | 80 | 70 | 50 | — | 65 |
| 178 | 0.035 | 85 | 70 | 85 | — | 85 | 90 | 70 | — | 80 |
| 179 | 0.28 | 80 | 90 | 85 | — | 75 | 70 | 70 | — | 70 |
| 180 | 0.28 | 85 | 80 | 80 | — | 85 | 50 | — | — | 75 |
| 181 | 0.070 | 80 | 95 | 75 | — | 75 | 90 | 70 | — | 75 |
| 182 | 0.14 | 80 | 85 | 95 | — | 70 | 40 | 75 | — | 60 |
| 183 | 0.28 | 85 | 90 | 95 | — | 75 | 30 | 50 | — | 50 |
| 186 | 0.070 | 90 | 90 | 95 | — | 98 | 75 | 75 | — | 90 |
| 187 | 0.070 | 90 | 85 | 90 | — | 95 | 80 | 85 | — | 85 |
| 188 | 0.14 | 70 | 80 | 30 | — | 65 | 85 | 95 | — | 75 |
| 189 | 0.14 | 85 | 95 | 80 | — | 75 | 85 | 75 | — | 60 |
| 190 | 0.070 | 90 | 85 | 98 | — | 85 | 80 | 70 | — | 50 |
| 191 | 0.018 | 85 | 80 | 90 | — | 75 | 98 | 70 | — | 70 |
| 192 | 0.14 | 80 | 90 | 80 | — | 85 | 95 | 95 | — | 85 |
| 193 | 0.14 | 90 | 90 | 75 | — | 85 | 95 | 85 | — | 80 |
| 194 | 0.035 | 80 | 95 | 85 | — | 90 | 90 | 95 | — | 80 |
| 195 | 0.28 | 70 | 80 | 50 | — | 80 | 78 | 60 | — | 85 |
| 198 | 0.070 | 85 | 98 | 95 | — | 85 | 85 | 80 | — | 80 |
| 199 | 0.070 | 85 | 95 | 95 | — | 80 | 90 | 35 | — | 80 |
| 200 | 0.070 | 85 | 95 | 75 | — | 90 | 95 | 85 | — | 85 |
| 201 | 0.035 | 90 | 95 | 90 | — | 80 | 98 | 78 | — | 75 |
| 202 | 0.070 | 80 | 98 | 70 | — | 80 | 90 | 80 | — | 78 |
| 203 | 0.14 | 75 | 98 | 75 | — | 99 | 98 | 98 | — | 80 |
| 204 | 0.56 | 90 | 90 | 85 | — | 85 | 80 | 75 | — | 60 |
| 205 | 0.070 | 95 | 98 | 90 | — | 95 | 85 | 95 | — | 85 |
| 208 | 0.28 | 88 | 95 | 90 | — | 95 | 75 | 90 | — | 90 |
| 213 | 0.035 | 85 | 80 | 90 | — | 80 | 60 | 50 | — | 70 |
| 214 | 0.14 | 85 | 95 | 95 | — | 100 | 95 | 95 | — | 100 |
| 215 | 0.070 | 70 | 50 | 85 | — | 100 | 90 | 45 | — | 90 |
| 216 | 0.070 | 75 | 85 | 95 | — | 100 | 100 | 60 | — | 80 |

TABLE 3-continued

PREEMERGENCE HERBICIDAL ACTIVITY

| Cpd. No. | Rate, Kg/Ha | Morning-glory | Pigweed | Velvet-leaf | Wild Buck-wheat | Black-grass | Barn-yard Grass | Giant fox-tail | Johnson-grass | Wild oats |
|---|---|---|---|---|---|---|---|---|---|---|
| 217 | 0.035 | 70 | 75 | 60 | — | 90 | 95 | 70 | — | 75 |
| 218 | 0.28 | 90 | 100 | 100 | — | –90 | 78 | 60 | — | 90 |
| 219 | 0.28 | 90 | 70 | 95 | — | 100 | 100 | 60 | — | 98 |
| 220 | 0.56 | 30 | 60 | 75 | — | 75 | 25 | 65 | — | 90 |
| 221 | 0.28 | 40 | 90 | 75 | — | 100 | 75 | 95 | — | 85 |
| 223 | 0.28 | 80 | 95 | 95 | — | — | 73 | 95 | — | 80 |
| 224 | 0.28 | 50 | 60 | 75 | — | — | 0 | 40 | — | 40 |
| 225 | 0.28 | 80 | 80 | 90 | — | — | 70 | 78 | — | 90 |
| 226 | 0.070 | 80 | 95 | 90 | — | — | 98 | 95 | — | 95 |
| 227 | 0.035 | 70 | 80 | 78 | — | — | 85 | 90 | — | 90 |
| 228 | 0.14 | 80 | 90 | 80 | — | — | 95 | 90 | — | 80 |
| 229 | 0.56 | 80 | 85 | 80 | — | — | 95 | 85 | — | 80 |
| 230 | 0.28 | 90 | 100 | 95 | — | — | 70 | 70 | — | 90 |
| 231 | 0.14 | 85 | 90 | 90 | — | — | 75 | 70 | — | 90 |
| 232 | 0.14 | 90 | 90 | 90 | — | — | 95 | 80 | — | 90 |
| 233 | 0.035 | 70 | 98 | 80 | — | 90 | 85 | 90 | — | 80 |
| 234 | 0.14 | 90 | 95 | 90 | — | 90 | 95 | 95 | — | 95 |
| 235 | 0.14 | 90 | 98 | 95 | — | 90 | 90 | 90 | — | 85 |
| 236 | 0.14 | 90 | 80 | 85 | — | 100 | 90 | 90 | — | 85 |
| 238 | 0.28 | 85 | 95 | 85 | — | 90 | 90 | 80 | — | 85 |
| 239 | 0.14 | 80 | 95 | 90 | — | 90 | 90 | 95 | — | 80 |
| 240 | 0.070 | 85 | 95 | 80 | — | 95 | 90 | 80 | — | 80 |
| 241 | 0.28 | 90 | 90 | 95 | — | — | 78 | 70 | — | 80 |
| 242 | 0.14 | 95 | 100 | 90 | — | — | 80 | 75 | — | 100 |
| 243 | 0.070 | 90 | 98 | 80 | — | 100 | 100 | 95 | — | 90 |
| 244 | 0.14 | 90 | 95 | 80 | — | 90 | 90 | 95 | — | 90 |
| 245 | 0.28 | 85 | 85 | 80 | — | — | 90 | 70 | — | 70 |
| 246 | 0.070 | 90 | 95 | 78 | — | — | 80 | 90 | — | 85 |
| 247 | 0.28 | 85 | 100 | 85 | — | — | 95 | 95 | — | 95 |
| 248 | 0.28 | 75 | 98 | 75 | — | — | 90 | 90 | — | 90 |
| 249 | 0.56 | 80 | 98 | 70 | — | — | 90 | 95 | — | 90 |
| 250 | 0.070 | 80 | 95 | 90 | — | 85 | 95 | 90 | — | 80 |
| 251 | 0.070 | 78 | 95 | 90 | — | 80 | 95 | 78 | — | 80 |

What is claimed is:

1. A halosulfonyl compound of the formula:

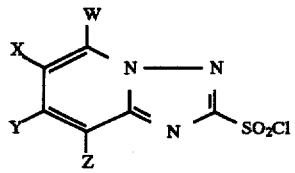

wherein W, X, Y, and Z each independently represents H, $CH_3$, $CH_2CH_3$, $CH_2OCH_3$, $CF_3$, F, Cl, Br, I, $OCH_2CF_3$, or $O(C_1-C_3)$alkyl optionally monosubstituted with F, Cl, or $OCH_3$ with the proviso that at least one of W, X, Y, and Z represents H.

2. A compound according to claim 1 wherein two of W, X, Y, and Z represent H.

3. A compound according to claim 2 wherein one or both of W and Z represents Cl or $OCH_3$ or wherein W represents $OCH_2CH_3$ or $OC_3H_7(i)$.

4. A compound according to claim 3 wherein W represents chloro, methoxy, ethoxy, or isopropoxy, X and Z each represent hydrogen, and Y represents methyl or a halogen; or wherein W represents chloro, methoxy or ethoxy, X and Y each represent hydrogen, and Z represents methyl, methoxy, or a halogen; or wherein Z represents chloro, methoxy or ethoxy, W and Y each represent hydrogen, and X represents methyl, trifluoromethyl, or a halogen.

5. A benzylthio compound of the formula:

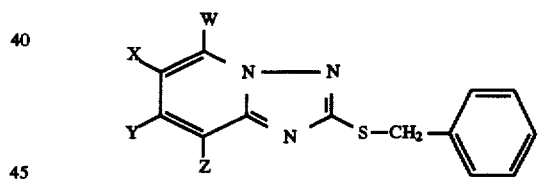

wherein W, X, Y, and Z each independently represents H, $CH_3$, $CH_2CH_3$, $CH_2OCH_3$, $CF_3$, F, Cl, Br, I, $OCH_2CF_3$, or $O(C_1-C_3)$alkyl optionally monosubstituted with F, Cl, or $OCH_3$ with the proviso that at least one of W, X, Y, and Z represents H.

6. A compound according to claim 5 wherein two of W, X, Y, and Z represent H.

7. A compound according to claim 6 wherein one or both of W and Z represents Cl or $OCH_3$ or wherein W represents $OCH_2CH_3$ or $OC_3H_7(i)$.

8. A compound according to claim 7 wherein W represents chloro, methoxy, ethoxy, or isopropoxy, X and Z each represent hydrogen, and Y represents methyl or a halogen; or wherein W represents chloro, methoxy or ethoxy, X and Y each represent hydrogen, and Z represents methyl, methoxy, or a halogen; or wherein Z represents chloro, methoxy or ethoxy, W and Y each represent hydrogen, and X represents methyl, trifluoromethyl, or a halogen.

9. A process for the preparation of an amino compound of the formula:

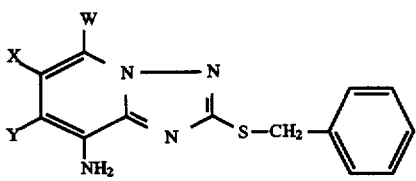

wherein

W represents Cl or (C$_1$–C$_3$)alkoxy;

X represents H; and

Y represents H, F, Cl, Br, I, or CH$_3$ which process comprises reducing the corresponding nitro compound of the formula:

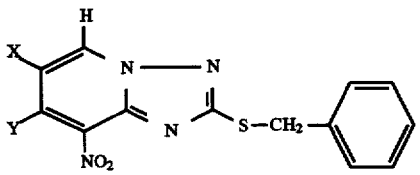

wherein

X represents H and

Y represents H, F, Cl, Br, I, or CH$_3$ with stannous chloride at a temperature of about 50° C. to about 120° C. with good agitation in the presence of a reactive medium comprising stannic chloride and either hydrogen chloride or a C$_1$–C$_3$ alcohol and, thereafter, basifying the product obtained to obtain said amino compound wherein W represents Cl or (C$_1$–C$_3$)alkoxy, respectively.

10. A process according to claim 9 wherein Y represents H and the reactive medium comprises stannic chloride and concentrated aqueous hydrogen chloride.

11. A process according to claim 9 wherein Y represents H and the reactive medium comprises methanol or ethanol.

12. A 2-amino[1,2,4]triazolo[1,5-a]pyridine compound of the formula:

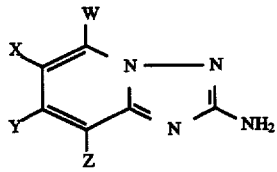

wherein W, X, Y, and Z each independently represents H, CH$_3$, CH$_2$CH$_3$, CH$_2$OCH$_3$, CF$_3$, halogen, OCH$_2$CF$_3$, or O(C$_1$–C$_3$)alkyl optionally monosubstituted with F, Cl, or OCH$_3$ with the proviso that two of W, X, Y, and Z represent H and two represent other than H.

13. A compound according to claim 12 wherein one or both of W and Z represents Cl or OCH$_3$ or wherein W represents OCH$_2$CH$_3$ or OC$_3$H$_7$(i).

14. A compound according to claim 13 wherein W represents chloro, methoxy, ethoxy, or isopropoxy, X and Z each represent hydrogen, and Y represents methyl or a halogen; or wherein w represents chloro, methoxy or ethoxy, X and Y each represent hydrogen, and Z represents methyl, methoxy, or a halogen; or wherein Z represents chloro, methoxy or ethoxy, W and Y each represent hydrogen, and X represents methyl, trifluoromethyl, or a halogen.

15. A compound according to claim 14 which is 2-amino-5-chloro-8-methoxy[1,2,4]triazolo[1,5-a]pyridine.

* * * * *